(12) United States Patent
Briggs et al.

(10) Patent No.: US 7,850,621 B2
(45) Date of Patent: Dec. 14, 2010

(54) METHOD AND APPARATUS FOR BODY FLUID SAMPLING AND ANALYTE SENSING

(75) Inventors: Barry Dean Briggs, Campbell, CA (US); Travis Marsot, Mountain View, CA (US); Jason Hegener, San Francisco, CA (US); Dominique M. Freeman, La Honda, CA (US); Dirk Boecker, Palo Alto, CA (US); Don Alden, Sunnyvale, CA (US); Matt Schumann, Cambridge (GB); Mike Beadman, Cambridge (GB)

(73) Assignee: Pelikan Technologies, Inc., Palo Alto, CA (US)

( * ) Notice: Subject to any disclaimer, the term of this patent is extended or adjusted under 35 U.S.C. 154(b) by 1175 days.

(21) Appl. No.: 10/559,223

(22) PCT Filed: Jun. 7, 2004

(86) PCT No.: PCT/US2004/018132

§ 371 (c)(1),
(2), (4) Date: May 5, 2006

(87) PCT Pub. No.: WO2004/107964

PCT Pub. Date: Dec. 16, 2004

(65) Prior Publication Data

US 2008/0021490 A1    Jan. 24, 2008

(51) Int. Cl.
*A61B 5/00* (2006.01)
*A61B 17/32* (2006.01)
*A61B 17/14* (2006.01)
*B65D 81/00* (2006.01)

(52) U.S. Cl. .......... 600/583; 600/573; 600/576; 600/578; 600/579; 606/167; 606/181

(58) Field of Classification Search .......... 600/573, 600/576, 577, 578, 579, 583, 584; 606/171, 606/172, 180, 181, 182, 183, 184, 185, 186
See application file for complete search history.

(56) References Cited

U.S. PATENT DOCUMENTS

| 1,733,847 A | 10/1929 | Wilmot |
| 2,801,633 A | 8/1957 | Mauze et al. |
| 3,358,689 A | 12/1967 | Higgins ............ 128/329 |
| 3,494,358 A | 2/1970 | Grossenbacher ...... 128/218 |
| 3,626,929 A | 12/1971 | Sanz ............... 128/2 R |

(Continued)

FOREIGN PATENT DOCUMENTS

DE    4420232    12/1995

(Continued)

*Primary Examiner*—Max Hindenburg
*Assistant Examiner*—Jeffrey G Hoekstra
(74) *Attorney, Agent, or Firm*—Paul Davis; Goodwin Procter LLP

(57) ABSTRACT

A method of controlling a penetrating member is provided. The method comprises providing a lancing device comprising a penetrating member driver having a position sensor and a processor that can determine the relative position and velocity of the penetrating member based on measuring relative position of the penetrating member with respect to time; providing a predetermined velocity control trajectory based on a model of the driver and a model of tissue to be contacted. In some embodiments, a feedforward control to maintain penetrating member velocity along said trajectory.

6 Claims, 45 Drawing Sheets

U.S. PATENT DOCUMENTS

| | | | |
|---|---|---|---|
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,224,125 A | 9/1980 | Nakamura | 204/195 B |
| 4,230,118 A | 10/1980 | Holman et al. | 128/314 |
| 4,338,174 A | 7/1982 | Tamura | 204/195 |
| 4,340,669 A | 7/1982 | Bauer | 435/14 |
| 4,353,984 A | 10/1982 | Yamada | 435/14 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,420,564 A | 12/1983 | Tsuji | 435/288 |
| 4,426,451 A | 1/1984 | Columbus | 436/518 |
| 4,426,884 A | 1/1984 | Polchaninoff | 73/172 |
| 4,469,110 A | 9/1984 | Slama | 128/770 |
| 4,517,978 A | 5/1985 | Levin | 128/314 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,637,393 A | 1/1987 | Ray | 128/305 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,661,768 A | 4/1987 | Carusillo | |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,757,022 A | 7/1988 | Shults et al. | 435/291 |
| 4,758,323 A | 7/1988 | Davis | 204/403 |
| 4,794,926 A | 1/1989 | Munsch et al. | 606/183 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,824,639 A | 4/1989 | Hildenbrand | 422/56 |
| RE32,922 E | 5/1989 | Levin et al. | 128/314 |
| 4,827,763 A | 5/1989 | Bourland | 73/172 |
| 4,830,959 A | 5/1989 | McNeill | 435/53 |
| 4,836,904 A | 6/1989 | Armstrong | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birth | 204/409 |
| 4,911,794 A | 3/1990 | Parce | 204/1 T |
| 4,920,977 A | 5/1990 | Haynes | 128/770 |
| 4,924,879 A | 5/1990 | O'Brien | |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| 5,029,583 A | 7/1991 | Meserol | |
| 5,047,044 A | 9/1991 | Smith et al. | |
| 5,054,499 A | 10/1991 | Swierczek | 128/770 |
| 5,059,789 A | 10/1991 | Salcudean | 250/206.1 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,108,889 A | 4/1992 | Smith et al. | |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,216,597 A | 6/1993 | Beckers | 364/413.02 |
| 5,217,480 A | 6/1993 | Haber | 606/182 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,573 S | 12/1993 | Cerola | D24/147 |
| 5,272,087 A | 12/1993 | El Murr | 435/291 |
| 5,277,181 A | 1/1994 | Mendelson | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |

| Patent No. | Date | Inventor | Class |
|---|---|---|---|
| 5,288,636 A | 2/1994 | Pollman | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,316,012 A | 5/1994 | Siegal | 128/744 |
| 5,318,583 A | 6/1994 | Rabenau | 606/182 |
| 5,320,607 A | 6/1994 | Ishibashi | 604/115 |
| 5,324,302 A | 6/1994 | Crouse | 606/181 |
| 5,324,303 A | 6/1994 | Strong | 606/181 |
| 5,332,479 A | 7/1994 | Uenoyama | 204/153.12 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,371,687 A | 12/1994 | Holmes | 364/514 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentzkow | 435/180 |
| 5,393,903 A | 2/1995 | Gratzel | 556/137 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,511 A | 4/1995 | White | 204/153.1 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,409,664 A | 4/1995 | Allen | |
| 5,410,059 A | 4/1995 | Fraser | 546/10 |
| 5,423,847 A | 6/1995 | Strong et al. | 606/182 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,454,828 A | 10/1995 | Schraga | 606/181 |
| 5,456,875 A | 10/1995 | Lambert | 264/328.1 |
| 5,464,418 A | 11/1995 | Schraga | 606/182 |
| 5,471,102 A | 11/1995 | Becker | 310/50 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| 5,496,453 A | 3/1996 | Uenoyama | 205/777.5 |
| 5,498,542 A | 3/1996 | Corey | 435/283.1 |
| 5,507,288 A | 4/1996 | Bocker | 128/633 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith et al. | |
| 5,518,006 A | 5/1996 | Mawhirt | 128/770 |
| 5,524,636 A | 6/1996 | Sarvazyan | 128/774 |
| 5,525,511 A | 6/1996 | D'Costa | 435/287.9 |
| 5,527,333 A | 6/1996 | Nikkels | 606/182 |
| 5,527,334 A | 6/1996 | Kanner | 606/182 |
| 5,540,676 A | 7/1996 | Freiberg | |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,547,702 A | 8/1996 | Gleisner | 427/2.13 |
| 5,554,166 A | 9/1996 | Lange | 606/182 |
| 5,558,834 A | 9/1996 | Chu | 422/55 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,593,852 A | 1/1997 | Heller | 435/14 |
| 5,609,749 A | 3/1997 | Yamauchi | 205/777.5 |
| 5,613,978 A | 3/1997 | Harding | 606/181 |
| 5,620,579 A | 4/1997 | Genshaw et al. | 204/402 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403 |
| 5,640,954 A | 6/1997 | Pfeiffer | 128/635 |
| 5,643,306 A | 7/1997 | Schraga | 606/182 |
| 5,645,555 A | 7/1997 | Davis | 606/182 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,662,127 A | 9/1997 | De Vaughn | 128/765 |
| 5,662,672 A | 9/1997 | Pambianchi | 606/181 |
| 5,676,143 A | 10/1997 | Simonsen | 128/633 |
| 5,680,858 A | 10/1997 | Hansen et al. | 128/635 |
| 5,680,872 A | 10/1997 | Sesekura | 128/760 |
| 5,682,884 A | 11/1997 | Hill | 128/637 |
| 5,683,562 A | 11/1997 | Schaffar | 204/403 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| 5,723,284 A | 3/1998 | Ye | 435/4 |
| 5,727,548 A | 3/1998 | Hill | 128/637 |
| 5,730,753 A | 3/1998 | Morita | 606/181 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,738,244 A | 4/1998 | Charlton et al. | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,898 A | 5/1998 | Preidel | 204/403 |
| 5,755,733 A | 5/1998 | Morita | 606/182 |
| 5,759,364 A | 6/1998 | Charlton | 204/403 |
| 5,762,770 A | 6/1998 | Pritchard | 204/403 |
| 5,770,086 A | 6/1998 | Indriksons et al. | |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,719 A | 7/1998 | Douglas | 435/28 |
| 5,782,770 A | 7/1998 | Mooradian | 600/476 |
| 5,782,852 A | 7/1998 | Foggia | 606/476 |
| 5,788,652 A | 8/1998 | Rahn | 600/577 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |

| Patent No. | Date | Inventor | Class |
|---|---|---|---|
| 5,820,551 A | 10/1998 | Hill | 600/347 |
| 5,822,715 A | 10/1998 | Worthington | 702/19 |
| 5,824,491 A | 10/1998 | Priest | 435/28 |
| 5,828,943 A | 10/1998 | Brown | 434/258 |
| 5,830,219 A | 11/1998 | Bird et al. | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,849,174 A | 12/1998 | Sanghera | 205/775 |
| 5,853,373 A | 12/1998 | Griffith | 600/554 |
| D403,975 S | 1/1999 | Douglas et al. | D10/81 |
| 5,857,983 A | 1/1999 | Douglas | 600/538 |
| 5,860,922 A | 1/1999 | Gordon et al. | 600/431 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons et al. | |
| 5,872,713 A | 2/1999 | Douglas | 702/85 |
| 5,873,887 A | 2/1999 | King | 606/182 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,373 A | 3/1999 | Roper | 606/344 |
| 5,882,494 A | 3/1999 | Van Antwerp | 204/403 |
| 5,885,211 A | 3/1999 | Eppstein | 600/309 |
| 5,887,133 A | 3/1999 | Brown | 395/200.3 |
| RE36,191 E | 4/1999 | Solomon | 395/308 |
| 5,893,870 A | 4/1999 | Talen | 606/201 |
| 5,897,493 A | 4/1999 | Brown | 600/300 |
| 5,899,855 A | 5/1999 | Brown | 600/301 |
| 5,899,915 A | 5/1999 | Saadat et al. | |
| 5,900,130 A | 5/1999 | Benvegnu | 204/453 |
| 5,906,921 A | 5/1999 | Ikeda | 435/25 |
| D411,619 S | 6/1999 | Duchon | D24/146 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,921,963 A | 7/1999 | Erez | 604/192 |
| 5,922,188 A | 7/1999 | Ikeda | 204/777.5 |
| RE36,268 E | 8/1999 | Szuminsky | 205/777.5 |
| 5,933,136 A | 8/1999 | Brown | 345/327 |
| 5,935,075 A | 8/1999 | Casscells et al. | 600/474 |
| 5,940,153 A | 8/1999 | Castaneda | |
| 5,942,102 A | 8/1999 | Hodges | 205/775 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,958,199 A | 9/1999 | Miyamoto | 204/403 |
| 5,960,403 A | 9/1999 | Brown | 705/2 |
| 5,964,718 A | 10/1999 | Duchon | 600/583 |
| 5,965,380 A | 10/1999 | Heller | 435/14 |
| 5,972,199 A | 10/1999 | Heller | 205/777.5 |
| 5,972,715 A | 10/1999 | Celentano | 436/164 |
| 5,974,124 A | 10/1999 | Schlueter | 379/106.02 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,993,400 A | 11/1999 | Rincoe | 600/595 |
| 5,997,476 A | 11/1999 | Brown | 600/300 |
| 5,997,561 A | 12/1999 | Bocker | 606/182 |
| 5,997,817 A | 12/1999 | Crismore | 422/58 |
| 5,997,818 A | 12/1999 | Hackner | 422/681 |
| 6,001,067 A | 12/1999 | Shults | 600/584 |
| 6,015,392 A | 1/2000 | Douglas | 600/583 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,023,686 A | 2/2000 | Brown | 705/37 |
| 6,027,459 A | 2/2000 | Shain et al. | |
| 6,030,399 A | 2/2000 | Ignotz | 606/167 |
| 6,030,827 A | 2/2000 | Davis | 435/287 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons et al. | 422/100 |
| 6,041,253 A | 3/2000 | Kost | 604/20 |
| 6,048,352 A | 4/2000 | Douglas | 606/181 |
| D424,696 S | 5/2000 | Ray | D24/169 |
| 6,056,701 A | 5/2000 | Duchon | 600/583 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,074,360 A | 6/2000 | Haar et al. | 604/57 |
| 6,077,408 A | 6/2000 | Miyamoto | 204/403 |
| 6,080,172 A | 6/2000 | Fujiwara | 606/166 |
| 6,083,710 A | 7/2000 | Heller | 435/14 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,093,146 A | 7/2000 | Filangeri | 600/300 |
| 6,093,156 A | 7/2000 | Cunningham et al. | 600/573 |
| 6,101,478 A | 8/2000 | Brown | 705/2 |
| 6,103,033 A | 8/2000 | Say | 156/73.1 |
| 6,107,083 A | 8/2000 | Collins | 435/288 |
| 6,113,578 A | 9/2000 | Brown | 604/207 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,129,823 A | 10/2000 | Hughes | 204/403.01 |
| 6,133,837 A | 10/2000 | Riley | 340/573.1 |
| 6,134,461 A | 10/2000 | Say | 600/345 |
| 6,144,837 A | 11/2000 | Quy | 434/307 R |
| 6,151,586 A | 11/2000 | Brown | 705/14 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,157,442 A | 12/2000 | Raskas | 356/39 |
| 6,161,095 A | 12/2000 | Brown | 705/2 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,171,325 B1 | 1/2001 | Mauze et al. | 606/171 |
| 6,175,752 B1 | 1/2001 | Say | 600/345 |
| 6,177,000 B1 | 1/2001 | Peterson | 205/777.5 |
| 6,177,931 B1 | 1/2001 | Alexander et al. | |
| 6,186,145 B1 | 2/2001 | Brown | 128/897 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |
| 6,194,900 B1 | 2/2001 | Freeman | 324/321 |
| 6,197,257 B1 | 3/2001 | Raskas | 422/82.05 |
| 6,206,841 B1 | 3/2001 | Cunningham et al. | 600/584 |
| 6,210,272 B1 | 4/2001 | Brown | 463/1 |
| 6,210,421 B1 | 4/2001 | Bocker et al. | 606/182 |
| 6,212,417 B1 | 4/2001 | Ikeda | 204/403.14 |
| 6,214,804 B1 | 4/2001 | Felgner | 514/44 |
| 6,221,238 B1 | 4/2001 | Grundig | 205/777.5 |
| 6,225,078 B1 | 5/2001 | Ikeda | 435/25 |
| 6,228,100 B1 | 5/2001 | Schraga | |
| 6,230,501 B1 | 5/2001 | Bailey | 62/51.1 |

| | | | | | | | |
|---|---|---|---|---|---|---|---|
| 6,233,471 | B1 | 5/2001 | Berner ... 600/345 | 6,501,404 | B2 | 12/2002 | Walker ... 341/143 |
| 6,233,539 | B1 | 5/2001 | Brown ... 703/11 | 6,503,209 | B2 | 1/2003 | Hakky et al. |
| 6,240,393 | B1 | 5/2001 | Brown ... 705/1 | 6,503,231 | B1 | 1/2003 | Prausnitz ... 604/272 |
| 6,241,862 | B1 | 6/2001 | McAleer ... 204/403 | 6,503,381 | B1 | 1/2003 | Gotoh ... 204/403.14 |
| 6,245,060 | B1 | 6/2001 | Loomis ... 606/9 | 6,506,168 | B1 | 1/2003 | Fathallah ... 600/578 |
| 6,246,992 | B1 | 6/2001 | Brown ... 705/2 | 6,508,785 | B1 | 1/2003 | Eppstein ... 604/113 |
| 6,248,065 | B1 | 6/2001 | Brown ... 600/300 | 6,514,270 | B1 | 2/2003 | Schraga ... 606/182 |
| 6,251,260 | B1 | 6/2001 | Heller ... 205/777.5 | 6,514,460 | B1 | 2/2003 | Fendrock ... 422/55 |
| 6,254,831 | B1 | 7/2001 | Barnard ... 422/82.08 | 6,519,241 | B1 | 2/2003 | Theimer ... 370/338 |
| 6,256,533 | B1 | 7/2001 | Vuzhakov ... 604/21 | 6,520,326 | B2 | 2/2003 | McIvor ... 206/305 |
| 6,258,229 | B1 | 7/2001 | Winarta ... 204/403 | 6,527,778 | B2 | 3/2003 | Athanasiou ... 606/80 |
| 6,258,254 | B1 | 7/2001 | Miyamoto ... 205/777.5 | 6,530,892 | B1 | 3/2003 | Kelly ... 600/583 |
| 6,261,519 | B1 | 7/2001 | Harding | 6,530,937 | B1 | 3/2003 | Schraga ... 606/182 |
| 6,268,161 | B1 | 7/2001 | Han ... 435/14 | 6,533,949 | B1 | 3/2003 | Yeshurun ... 216/11 |
| 6,270,455 | B1 | 8/2001 | Brown ... 600/300 | 6,537,207 | B1 | 3/2003 | Rice ... 600/121 |
| 6,270,637 | B1 | 8/2001 | Crismore ... 204/403 | 6,537,242 | B1 | 3/2003 | Palmer ... 604/22 |
| 6,272,359 | B1 | 8/2001 | Kivela ... 455/567 | 6,537,292 | B1 | 3/2003 | Lee ... 606/182 |
| 6,281,006 | B1 | 8/2001 | Heller ... 435/287.9 | 6,540,672 | B1 | 4/2003 | Simonsen ... 600/300 |
| 6,283,982 | B1 | 9/2001 | Levaughn ... 606/172 | 6,540,675 | B2 | 4/2003 | Aceti ... 600/309 |
| 6,284,478 | B1 | 9/2001 | Heller ... 435/14 | 6,540,762 | B1 | 4/2003 | Bertling ... 606/182 |
| 6,285,448 | B1 | 9/2001 | Kuenstner ... 356/39 | 6,540,891 | B1 | 4/2003 | Stewart ... 204/403.14 |
| 6,290,683 | B1 | 9/2001 | Erez ... 604/273 | 6,541,266 | B2 | 4/2003 | Modzelewski ... 436/95 |
| 6,294,897 | B1 | 9/2001 | Champlin ... 320/153 | 6,547,954 | B2 | 4/2003 | Ikeda ... 205/777.5 |
| 6,295,506 | B1 | 9/2001 | Heinonen ... 702/104 | 6,549,796 | B2 | 4/2003 | Sohrab ... 600/345 |
| 6,299,757 | B1 | 10/2001 | Feldman ... 205/775 | 6,551,494 | B1 | 4/2003 | Heller et al. ... 205/777.5 |
| 6,302,844 | B1 | 10/2001 | Walker ... 600/300 | 6,553,244 | B2 | 4/2003 | Lesho ... 600/347 |
| 6,302,855 | B1 | 10/2001 | Lav ... 600/584 | 6,554,381 | B2 | 4/2003 | Locher ... 347/7 |
| 6,305,804 | B1 | 10/2001 | Rice ... 351/221 | 6,555,061 | B1 | 4/2003 | Leong ... 422/58 |
| 6,306,347 | B1 | 10/2001 | Mason ... 422/58 | 6,558,320 | B1 | 5/2003 | Causey ... 600/300 |
| 6,309,535 | B1 | 10/2001 | Williams ... 205/777.5 | 6,558,361 | B1 | 5/2003 | Yeshurun ... 604/272 |
| 6,312,612 | B1 | 11/2001 | Sherman ... 216/2 | 6,558,402 | B1 | 5/2003 | Chelak ... 606/182 |
| 6,315,738 | B1 | 11/2001 | Nishikawa | 6,558,528 | B1 | 5/2003 | Matzinger ... 205/777.5 |
| 6,322,574 | B1 | 11/2001 | Lloyd ... 606/181 | 6,560,471 | B1 | 5/2003 | Heller ... 600/347 |
| 6,329,161 | B1 | 12/2001 | Heller ... 435/14 | 6,561,978 | B1 | 5/2003 | Conn ... 600/309 |
| 6,330,426 | B2 | 12/2001 | Brown ... 434/307 R | 6,561,989 | B2 | 5/2003 | Whitson ... 600/573 |
| 6,331,163 | B1 | 12/2001 | Kaplan ... 600/486 | 6,562,210 | B1 | 5/2003 | Bhullar ... 204/403.3 |
| 6,334,363 | B1 | 1/2002 | Testud ... 73/862 | 6,565,509 | B1 | 5/2003 | Say et al. ... 600/365 |
| 6,334,778 | B1 | 1/2002 | Brown ... 434/258 | 6,565,808 | B2 | 5/2003 | Hudak ... 422/58 |
| 6,334,856 | B1 | 1/2002 | Allen ... 604/191 | 6,569,157 | B1 | 5/2003 | Shain ... 606/12 |
| 6,338,790 | B1 | 1/2002 | Feldman ... 205/777.5 | 6,571,651 | B1 | 6/2003 | Hodges ... 73/864.72 |
| 6,349,229 | B1 | 2/2002 | Watanabe ... 600/345 | 6,572,566 | B2 | 6/2003 | Effenhauser ... 600/584 |
| 6,350,273 | B1 | 2/2002 | Minagawa ... 606/186 | 6,574,490 | B2 | 6/2003 | Abbink ... 600/316 |
| 6,350,451 | B1 | 2/2002 | Horn ... 424/184.1 | 6,575,905 | B2 | 6/2003 | Knobbe ... 600/365 |
| 6,352,523 | B1 | 3/2002 | Brown ... 604/207 | 6,576,101 | B1 | 6/2003 | Heller ... 204/403.14 |
| 6,353,753 | B1 | 3/2002 | Flock ... 600/473 | 6,576,117 | B1 | 6/2003 | Iketaki et al. ... 205/777.5 |
| 6,364,889 | B1 | 4/2002 | Kheiri et al. ... 606/181 | 6,576,416 | B2 | 6/2003 | Haviland ... 435/4 |
| 6,368,273 | B1 | 4/2002 | Brown ... 600/300 | 6,579,690 | B1 | 6/2003 | Bonnecaze et al. ... 435/14 |
| 6,375,469 | B1 | 4/2002 | Brown ... 434/236 | 6,582,573 | B2 | 6/2003 | Douglas ... 204/403.1 |
| 6,379,301 | B1 | 4/2002 | Worthington ... 600/309 | 6,587,705 | B1 | 7/2003 | Kim et al. ... 600/347 |
| 6,379,324 | B1 | 4/2002 | Gartstein ... 604/22 | 6,589,260 | B1 | 7/2003 | Schmelzeisen-R ... 606/181 |
| 6,379,969 | B1 | 4/2002 | Mauze et al. | 6,589,261 | B1 | 7/2003 | Abulhaj ... 606/181 |
| 6,381,577 | B1 | 4/2002 | Brown ... 705/2 | 6,591,125 | B1 | 7/2003 | Buse ... 600/347 |
| 6,387,709 | B1 | 5/2002 | Mason ... 436/164 | 6,592,745 | B1 | 7/2003 | Feldman ... 205/777.5 |
| 6,399,394 | B1 | 6/2002 | Dahm ... 436/180 | 6,595,919 | B2 | 7/2003 | Berner ... 600/365 |
| 6,413,410 | B1 | 7/2002 | Hodges ... 205/775 | 6,599,407 | B2 | 7/2003 | Taniike ... 204/403.1 |
| 6,413,411 | B1 | 7/2002 | Pottgen ... 205/777.5 | 6,599,693 | B1 | 7/2003 | Webb ... 435/4 |
| 6,421,633 | B1 | 7/2002 | Heinonen ... 703/11 | 6,602,205 | B1 | 8/2003 | Erickson ... 600/573 |
| 6,423,014 | B1 | 7/2002 | Churchill et al. | 6,602,268 | B2 | 8/2003 | Kuhr ... 606/181 |
| 6,428,664 | B1 | 8/2002 | Bhullar ... 204/403.03 | 6,602,678 | B2 | 8/2003 | Kwon ... 435/14 |
| 6,436,256 | B1 | 8/2002 | Williams ... 204/403.06 | 6,604,050 | B2 | 8/2003 | Trippel ... 702/19 |
| 6,436,721 | B1 | 8/2002 | Kuo ... 436/514 | 6,607,494 | B1 | 8/2003 | Fowler ... 600/570 |
| 6,440,645 | B1 | 8/2002 | Yon-Hin ... 430/322 | 6,607,658 | B1 | 8/2003 | Heller ... 205/777.5 |
| 6,451,040 | B1 | 9/2002 | Purcell ... 606/181 | 6,616,616 | B2 | 9/2003 | Fritz ... 600/583 |
| 6,458,258 | B2 | 10/2002 | Taniike ... 204/403 | 6,616,819 | B1 | 9/2003 | Liamos ... 204/403.02 |
| 6,462,162 | B2 | 10/2002 | van Antwerp ... 528/77 | 6,618,934 | B1 | 9/2003 | Feldman ... 29/830 |
| 6,464,649 | B1 | 10/2002 | Duchon ... 600/583 | 6,620,112 | B2 | 9/2003 | Klitmose ... 600/583 |
| 6,471,903 | B2 | 10/2002 | Sherman ... 264/328.1 | 6,623,501 | B2 | 9/2003 | Heller ... 606/181 |
| 6,475,436 | B1 | 11/2002 | Schabbach ... 422/64 | 6,626,851 | B2 | 9/2003 | Hirao ... 600/576 |
| 6,475,750 | B1 | 11/2002 | Han et al. ... 435/14 | 6,635,222 | B2 | 10/2003 | Kent ... 422/22 |
| 6,477,394 | B2 | 11/2002 | Rice ... 600/318 | 6,638,772 | B1 | 10/2003 | Douglas ... 436/518 |
| 6,477,424 | B1 | 11/2002 | Thompson ... 607/60 | 6,641,533 | B2 | 11/2003 | Causey ... 600/300 |
| 6,484,046 | B1 | 11/2002 | Say ... 600/345 | 6,645,142 | B2 | 11/2003 | Braig ... 600/300 |
| 6,494,830 | B1 | 12/2002 | Wessel ... 600/300 | 6,645,219 | B2 | 11/2003 | Roe ... 606/182 |

| Patent | Date | Name | Class |
|---|---|---|---|
| 6,645,368 B1 | 11/2003 | Beaty | 205/792 |
| 6,650,915 B2 | 11/2003 | Routt | 600/319 |
| 6,652,720 B2 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Petersson | 600/316 |
| 6,679,841 B2 | 1/2004 | Bojan | 600/309 |
| 6,679,852 B1 | 1/2004 | Schmelzeisen-R et al. | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa et al. | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami et al. | 204/403.14 |
| 6,743,211 B1 | 6/2004 | Prausnitz | 604/239 |
| 6,743,635 B2 | 6/2004 | Neel | 436/95 |
| 6,749,618 B2 | 6/2004 | Levaughn | 606/182 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda et al. | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grubge | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips et al. | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,844,149 B2 | 1/2005 | Goldman | 435/4 |
| 6,847,451 B2 | 1/2005 | Pugh | 356/436 |
| 6,849,052 B2 | 2/2005 | Uchigaki et al. | 600/584 |
| 6,849,168 B2 | 2/2005 | Crumly et al. | 204/416 |
| 6,849,216 B2 | 2/2005 | Rappin | 264/134 |
| 6,850,790 B2 | 2/2005 | Berner | 600/347 |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,875,216 B2 | 4/2005 | Roe | 600/583 |
| 6,878,120 B2 | 4/2005 | Hodges | 204/403.14 |
| 6,878,251 B2 | 4/2005 | Wang | 204/452 |
| 6,878,255 B1 | 4/2005 | Taniike | 205/777.5 |
| 6,878,262 B2 | 4/2005 | Haar | 374/131 |
| 6,880,968 B1 | 4/2005 | Delmore | 604/272 |
| 6,881,203 B2 | 4/2005 | Tokunaga | 205/775 |
| 6,881,322 B2 | 4/2005 | Zimmer | 422/58 |
| 6,881,378 B1 | 4/2005 | Petersen et al. | |
| 6,881,541 B2 | 4/2005 | Phillips | 435/14 |
| 6,881,550 B2 | 4/2005 | Heller | 435/14 |
| 6,881,551 B2 | 4/2005 | Otake | 436/44 |
| 6,881,578 B2 | 4/2005 | Potts | 702/23 |
| 6,882,940 B2 | 4/2005 | Matzinger | 435/7.1 |
| 6,884,592 B2 | 4/2005 | Taniike | 324/444 |
| 6,885,196 B2 | 4/2005 | Parris | 600/347 |
| 6,885,883 B2 | 4/2005 | Elstrom | 606/41 |
| 6,887,239 B2 | 5/2005 | Schraga | 606/181 |
| 6,887,253 B2 | 5/2005 | Curie | 606/181 |
| 6,887,254 B1 | 5/2005 | Phillips | 422/56 |
| 6,887,426 B2 | 5/2005 | Leong | 436/8 |
| 6,887,709 B2 | 5/2005 | Routt | 600/319 |
| 6,889,069 B2 | 5/2005 | Crocker | 604/131 |
| 6,890,319 B1 | 5/2005 | Ohara | 205/777.5 |
| 6,890,421 B2 | 5/2005 | Bautista | 422/58 |
| 6,890,484 B2 | 5/2005 | Kai | 379/106.02 |
| 6,891,936 B2 | 5/2005 | McIvor | 600/347 |
| 6,892,085 B2 | 5/2005 | Schulze | 600/300 |
| 6,893,396 B2 | 5/2005 | Gotoh | 204/403.5 |
| 6,893,545 B2 | 5/2005 | Wang | 205/777.5 |
| 6,893,552 B1 | 5/2005 | Shin | 600/316 |
| 6,895,263 B2 | 5/2005 | Rice | 600/319 |
| 6,895,264 B2 | 5/2005 | Silver | 600/345 |
| 6,895,265 B2 | 5/2005 | Erdosy | 205/775 |
| 6,896,793 B2 | 5/2005 | Khair | 340/870.16 |
| 6,897,788 B2 | 6/2005 | Burson | 435/14 |
| 6,902,905 B2 | 6/2005 | Raskas | 600/310 |
| 6,904,301 B2 | 6/2005 | Russell | 427/393.5 |
| 6,905,733 B2 | 6/2005 | Pugh | 221/135 |
| 6,908,008 B2 | 6/2005 | Rankin | 204/406 |
| 6,908,535 B2 | 6/2005 | MacPhee | 422/22 |
| 6,908,591 B2 | 6/2005 | Shartle | 422/58 |
| 6,908,593 B1 | 6/2005 | Brenneman | 204/400 |
| 6,911,130 B2 | 6/2005 | | |

| | | | | | | | |
|---|---|---|---|---|---|---|---|
| 6,911,131 B2 | 6/2005 | Miyazaki | 204/403.14 | 6,991,918 B2 | 1/2006 | Keith | 435/31 |
| 6,911,621 B2 | 6/2005 | Bhullar | 219/121.69 | 6,991,940 B2 | 1/2006 | Carroll | 436/514 |
| 6,916,410 B2 | 7/2005 | Katsuki | 204/403 | 6,994,825 B2 | 2/2006 | Haviland | 422/58 |
| 6,918,874 B1 | 7/2005 | Hatch et al. | 600/365 | 6,997,317 B2 | 2/2006 | Catelli | 206/438 |
| 6,918,901 B1 | 7/2005 | Theeuwes et al. | | 6,997,343 B2 | 2/2006 | May | 221/232 |
| 6,918,918 B1 | 7/2005 | Schraga | 606/182 | 6,997,344 B2 | 2/2006 | Brown | 221/258 |
| 6,922,576 B2 | 7/2005 | Raskas | 600/316 | 6,997,936 B2 | 2/2006 | Marshall | 606/181 |
| 6,922,578 B2 | 7/2005 | Eppstein | 600/347 | 6,998,247 B2 | 2/2006 | Monfre | 435/14 |
| 6,923,764 B2 | 8/2005 | Aceti | 600/309 | 6,998,248 B2 | 2/2006 | Yani | 435/14 |
| 6,923,894 B2 | 8/2005 | Huang | 204/403.06 | 6,999,810 B2 | 2/2006 | Berner | 600/345 |
| 6,923,936 B2 | 8/2005 | Swanson | 422/22 | 7,001,343 B2 | 2/2006 | Erickson | 600/573 |
| 6,924,093 B2 | 8/2005 | Haviland | 435/4 | 7,001,344 B2 | 2/2006 | Freeman | 600/583 |
| 6,925,317 B1 | 8/2005 | Samuels | 600/344 | 7,003,337 B2 | 2/2006 | Harjunmaa | 600/316 |
| 6,925,393 B1 | 8/2005 | Kalatz | 702/27 | 7,003,340 B2 | 2/2006 | Say | 600/345 |
| 6,929,649 B2 | 8/2005 | Pugh | 606/182 | 7,003,341 B2 | 2/2006 | Say | 600/345 |
| 6,929,650 B2 | 8/2005 | Fukuzawa | 606/182 | 7,004,928 B2 | 2/2006 | Aceti | 604/191 |
| 6,931,327 B2 | 8/2005 | Goode | 702/22 | 7,005,048 B1 | 2/2006 | Watanabe | 204/403.04 |
| 6,931,328 B2 | 8/2005 | Braig | 702/23 | 7,005,273 B2 | 2/2006 | Heller | 435/25 |
| 6,939,310 B2 | 9/2005 | Matzinger | 600/573 | 7,005,459 B2 | 2/2006 | Hekal | 523/102 |
| 6,939,312 B2 | 9/2005 | Hodges | 600/583 | 7,005,857 B2 | 2/2006 | Stiene | 324/449 |
| 6,939,450 B2 | 9/2005 | Karinka | 204/409 | 7,006,857 B2 | 2/2006 | Braig | 600/310 |
| 6,940,591 B2 | 9/2005 | Sopp | 356/244 | 7,006,858 B2 | 2/2006 | Silver | 600/345 |
| 6,942,518 B2 | 9/2005 | Liamos | 439/495 | 7,008,384 B2 | 3/2006 | Tapper | 600/573 |
| 6,942,769 B2 | 9/2005 | Cheng | 204/400 | 7,010,432 B2 | 3/2006 | Kermani | 702/19 |
| 6,942,770 B2 | 9/2005 | Cai | 204/403.04 | 7,011,630 B2 | 3/2006 | Desai | 600/309 |
| 6,944,486 B2 | 9/2005 | Braig | 600/310 | 7,011,954 B2 | 3/2006 | Ouyang | 435/7.9 |
| 6,945,943 B2 | 9/2005 | Pugh | 600/584 | 7,014,615 B2 | 3/2006 | Erickson | 600/573 |
| 6,946,067 B2 | 9/2005 | Hodges | 205/792 | 7,015,262 B2 | 3/2006 | Leong | 523/205 |
| 6,946,098 B2 | 9/2005 | Miekka | 422/22 | 7,016,713 B2 | 3/2006 | Gardner | 600/310 |
| 6,946,299 B2 | 9/2005 | Neel | 436/95 | 7,018,568 B2 | 3/2006 | Tierney | 252/511 |
| 6,949,111 B2 | 9/2005 | Schraga | 606/182 | 7,018,848 B2 | 3/2006 | Douglas | 436/524 |
| 6,949,221 B2 | 9/2005 | Kiser | 422/56 | 7,022,217 B2 | 4/2006 | Hodges | 205/777.5 |
| 6,951,631 B1 | 10/2005 | Catt | 422/56 | 7,022,218 B2 | 4/2006 | Taniike | 205/777.5 |
| 6,951,728 B2 | 10/2005 | Qian | 435/14 | 7,022,286 B2 | 4/2006 | Lemke | 422/67 |
| 6,952,603 B2 | 10/2005 | Gerber | 600/310 | 7,024,236 B2 | 4/2006 | Ford | 600/345 |
| 6,952,604 B2 | 10/2005 | DeNuzzio | 600/345 | 7,024,248 B2 | 4/2006 | Penner | 607/60 |
| 6,953,693 B2 | 10/2005 | Neel | 436/149 | 7,024,399 B2 | 4/2006 | Sumner | 706/45 |
| 6,954,662 B2 | 10/2005 | Freger | 600/316 | 7,025,425 B2 | 4/2006 | Kovatchev | 300/365 |
| 6,958,072 B2 | 10/2005 | Schraga | 606/182 | 7,025,774 B2 | 4/2006 | Freeman | 606/181 |
| 6,958,129 B2 | 10/2005 | Galen | 422/57 | 7,027,848 B2 | 4/2006 | Robinson | 600/310 |
| 6,958,809 B2 | 10/2005 | Sterling | 356/39 | 7,029,444 B2 | 4/2006 | Shin | 600/365 |
| 6,959,211 B2 | 10/2005 | Rule | 600/310 | 7,033,322 B2 | 4/2006 | Silver | 600/486 |
| 6,959,247 B2 | 10/2005 | Neel | 702/19 | 7,033,371 B2 | 4/2006 | Alden | 606/181 |
| 6,960,287 B2 | 11/2005 | Charlton | 205/775 | 7,039,560 B2 | 5/2006 | Kawatahara | 702/187 |
| 6,960,289 B2 | 11/2005 | Hodges | 205/778 | 7,041,057 B1 | 5/2006 | Faupel | 600/365 |
| 6,964,871 B2 | 11/2005 | Bell | 436/95 | 7,041,063 B2 | 5/2006 | Abreu | 600/549 |
| 6,965,791 B1 | 11/2005 | Hitchcock | 600/345 | 7,041,068 B2 | 5/2006 | Freeman | 600/583 |
| 6,966,880 B2 | 11/2005 | Boecker | 600/583 | 7,041,254 B2 | 5/2006 | Haviland | 422/58 |
| 6,966,977 B2 | 11/2005 | Hasegawa | 204/403.07 | 7,041,468 B2 | 5/2006 | Drucker | 435/14 |
| 6,967,105 B2 | 11/2005 | Nomura | 436/169 | 7,043,287 B1 | 5/2006 | Khalil | 600/310 |
| 6,968,375 B1 | 11/2005 | Brown | 709/224 | 7,044,911 B2 | 5/2006 | Drinan | 600/300 |
| 6,969,359 B2 | 11/2005 | Duchon | 600/583 | 7,045,054 B1 | 5/2006 | Buck | 205/778 |
| 6,969,450 B2 | 11/2005 | Taniike | 204/403.01 | 7,045,097 B2 | 5/2006 | Kovacs | 422/82.08 |
| 6,969,451 B2 | 11/2005 | Shin | 204/412 | 7,045,310 B2 | 5/2006 | Buck | 435/7.93 |
| 6,973,706 B2 | 12/2005 | Say | 29/595 | 7,045,361 B2 | 5/2006 | Heiss | 436/172 |
| 6,975,893 B2 | 12/2005 | Say | 600/347 | 7,047,070 B2 | 5/2006 | Wilkinson | 604/20 |
| 6,977,032 B2 | 12/2005 | Hasegawa | 204/403.05 | 7,047,795 B2 | 5/2006 | Sato | 73/64.56 |
| 6,979,544 B2 | 12/2005 | Keen | 435/6 | 7,049,130 B2 | 5/2006 | Carroll | 435/287.2 |
| 6,979,571 B2 | 12/2005 | Modzelewski | 436/164 | 7,050,843 B2 | 5/2006 | Shartle | 600/345 |
| 6,982,027 B2 | 1/2006 | Yagi | 204/403.06 | 7,051,495 B2 | 5/2006 | Lang | 53/475 |
| 6,982,431 B2 | 1/2006 | Modlin et al. | | 7,052,268 B2 | 5/2006 | Powell | 425/542 |
| 6,983,176 B2 | 1/2006 | Gardner | 600/310 | 7,052,591 B2 | 5/2006 | Gao | 204/490 |
| 6,983,177 B2 | 1/2006 | Rule | 600/310 | 7,052,652 B2 | 5/2006 | Zanzucchi | 422/82.05 |
| 6,984,307 B2 | 1/2006 | Zweig | 205/777.5 | 7,052,864 B2 | 5/2006 | Durkop | 435/25 |
| 6,986,777 B2 | 1/2006 | Kim | 606/182 | 7,054,682 B2 | 5/2006 | Young | 604/20 |
| 6,986,869 B2 | 1/2006 | Tuohy | 422/56 | 7,054,759 B2 | 5/2006 | Fukunaga | 702/23 |
| 6,988,996 B2 | 1/2006 | Roe | 600/584 | D523,555 S | 6/2006 | Loerwald | D24/146 |
| 6,989,243 B2 | 1/2006 | Yani | 435/14 | 7,056,425 B2 | 6/2006 | Hasegawa | 204/403.04 |
| 6,989,891 B2 | 1/2006 | Braig | 356/39 | 7,056,495 B2 | 6/2006 | Roser | 424/45 |
| 6,990,365 B1 | 1/2006 | Parker | 600/328 | 7,058,437 B2 | 6/2006 | Buse | 600/347 |
| 6,990,366 B2 | 1/2006 | Say | 600/345 | 7,060,059 B2 | 6/2006 | Keith | 604/504 |
| 6,990,367 B2 | 1/2006 | Kiser | 600/345 | 7,060,192 B2 | 6/2006 | Yuzhakov | 216/11 |
| 6,990,849 B2 | 1/2006 | Bohm | 73/53.01 | 7,061,593 B2 | 6/2006 | Braig | 356/39 |

| Patent/Pub No. | Date | Name | Class |
|---|---|---|---|
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Jeong | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/300 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorczyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 7,225,535 B2 | 6/2007 | Feldman et al. | |
| 7,226,461 B2 | 6/2007 | Boecker et al. | |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0042004 A1 | 11/2001 | Taub et al. | 705/11 |
| 2001/0054319 A1 | 12/2001 | Heller | 73/849 |
| 2002/0016606 A1 | 2/2002 | Moerman | 606/181 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum et al. | |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan et al. | |
| 2002/0120216 A1 | 8/2002 | Fritz | 600/583 |
| 2002/0120261 A1 | 8/2002 | Morris | 606/41 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0136189 A1 | 7/2003 | Lauman et al. | |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |

| | | | |
|---|---|---|---|
| 2003/0144609 A1 | 7/2003 | Kennedy ........... 600/583 |
| 2003/0146110 A1 | 8/2003 | Karinka ........... 205/777.5 |
| 2003/0149348 A1 | 8/2003 | Raskas ........... 600/310 |
| 2003/0149377 A1 | 8/2003 | Erickson ........... 600/573 |
| 2003/0153900 A1 | 8/2003 | Aceti ........... 604/890.1 |
| 2003/0159944 A1 | 8/2003 | Pottgen ........... 205/777.5 |
| 2003/0163351 A1 | 8/2003 | Brown ........... 705/2 |
| 2003/0178322 A1 | 9/2003 | Iyengar ........... 205/775 |
| 2003/0191415 A1 | 10/2003 | Moerman ........... 600/584 |
| 2003/0195435 A1 | 10/2003 | Williams ........... 600/583 |
| 2003/0195540 A1 | 10/2003 | Moerman ........... 606/181 |
| 2003/0199744 A1 | 10/2003 | Buse ........... 600/347 |
| 2003/0199789 A1 | 10/2003 | Boecker ........... 600/575 |
| 2003/0199790 A1 | 10/2003 | Boecker ........... 600/576 |
| 2003/0199791 A1 | 10/2003 | Boecker ........... 600/576 |
| 2003/0199891 A1 | 10/2003 | Argauer ........... 606/181 |
| 2003/0199893 A1 | 10/2003 | Boecker ........... 606/181 |
| 2003/0199894 A1 | 10/2003 | Boecker ........... 606/181 |
| 2003/0199895 A1 | 10/2003 | Boecker ........... 606/181 |
| 2003/0199896 A1 | 10/2003 | Boecker ........... 606/181 |
| 2003/0199897 A1 | 10/2003 | Boecker ........... 606/181 |
| 2003/0199898 A1 | 10/2003 | Boecker ........... 606/181 |
| 2003/0199899 A1 | 10/2003 | Boecker ........... 606/181 |
| 2003/0199900 A1 | 10/2003 | Boecker ........... 606/181 |
| 2003/0199901 A1 | 10/2003 | Boecker ........... 606/181 |
| 2003/0199902 A1 | 10/2003 | Boecker ........... 606/181 |
| 2003/0199903 A1 | 10/2003 | Boecker ........... 606/181 |
| 2003/0199904 A1 | 10/2003 | Boecker ........... 606/181 |
| 2003/0199905 A1 | 10/2003 | Boecker ........... 606/181 |
| 2003/0199906 A1 | 10/2003 | Boecker ........... 606/181 |
| 2003/0199907 A1 | 10/2003 | Boecker ........... 606/181 |
| 2003/0199908 A1 | 10/2003 | Boecker ........... 606/181 |
| 2003/0199909 A1 | 10/2003 | Boecker ........... 606/181 |
| 2003/0199910 A1 | 10/2003 | Boecker ........... 606/181 |
| 2003/0199911 A1 | 10/2003 | Boecker ........... 606/181 |
| 2003/0199912 A1 | 10/2003 | Pugh ........... 606/182 |
| 2003/0201194 A1 | 10/2003 | Heller ........... 205/777.5 |
| 2003/0203352 A1 | 10/2003 | Haviland ........... 435/4 |
| 2003/0206828 A1 | 11/2003 | Bell ........... 422/44 |
| 2003/0208140 A1 | 11/2003 | Pugh ........... 600/584 |
| 2003/0212344 A1 | 11/2003 | Yuzhakov ........... 600/583 |
| 2003/0212345 A1 | 11/2003 | McAllister ........... 600/584 |
| 2003/0212346 A1 | 11/2003 | Yuzhakov ........... 600/584 |
| 2003/0212347 A1 | 11/2003 | Sohrab ........... 600/584 |
| 2003/0212423 A1 | 11/2003 | Pugh ........... 606/181 |
| 2003/0212424 A1 | 11/2003 | Briggs ........... 606/181 |
| 2003/0212579 A1 | 11/2003 | Brown ........... 705/2 |
| 2003/0216767 A1 | 11/2003 | List ........... 606/181 |
| 2003/0217918 A1 | 11/2003 | Davies ........... 204/403.14 |
| 2003/0220552 A1 | 11/2003 | Reghabi ........... 600/365 |
| 2003/0220663 A1 | 11/2003 | Fletcher ........... 606/182 |
| 2003/0223906 A1 | 12/2003 | McAllister ........... 422/58 |
| 2003/0225317 A1 | 12/2003 | Schell ........... 600/300 |
| 2003/0225429 A1 | 12/2003 | Garthe ........... 606/182 |
| 2003/0225430 A1 | 12/2003 | Schraga ........... 606/182 |
| 2003/0228637 A1 | 12/2003 | Wang ........... 435/7.9 |
| 2003/0229514 A2 | 12/2003 | Brown ........... 705/2 |
| 2003/0232370 A1 | 12/2003 | Trifiro ........... 435/6 |
| 2003/0233055 A1 | 12/2003 | Erickson ........... 600/573 |
| 2003/0233112 A1 | 12/2003 | Alden et al. ........... 606/181 |
| 2003/0233113 A1 | 12/2003 | Alden et al. ........... 606/182 |
| 2004/0006285 A1 | 1/2004 | Douglas ........... 600/583 |
| 2004/0007585 A1 | 1/2004 | Griffith ........... 221/232 |
| 2004/0009100 A1 | 1/2004 | Simons ........... 422/102 |
| 2004/0010279 A1 | 1/2004 | Freeman ........... 606/182 |
| 2004/0015064 A1 | 1/2004 | Parsons ........... 600/347 |
| 2004/0019250 A1 | 1/2004 | Catelli ........... 600/1 |
| 2004/0019259 A1 | 1/2004 | Brown ........... 600/300 |
| 2004/0026243 A1 | 2/2004 | Davies ........... 204/403.14 |
| 2004/0030353 A1 | 2/2004 | Schmelzeisen-R et al. .. 606/201 |
| 2004/0031682 A1 | 2/2004 | Wilsey ........... 204/403.1 |
| 2004/0034318 A1 | 2/2004 | Fritz ........... 604/19 |
| 2004/0038045 A1 | 2/2004 | Smart ........... 428/446 |
| 2004/0039303 A1 | 2/2004 | Wurster ........... 600/584 |
| 2004/0039342 A1 | 2/2004 | Eppstein ........... 604/200 |
| 2004/0039407 A1 | 2/2004 | Schraga ........... 606/181 |
| 2004/0039408 A1 | 2/2004 | Abulhaj ........... 606/181 |
| 2004/0049219 A1 | 3/2004 | Briggs ........... 606/181 |
| 2004/0049220 A1 | 3/2004 | Boecker ........... 606/181 |
| 2004/0050694 A1 | 3/2004 | Yang ........... 204/403.02 |
| 2004/0054267 A1 | 3/2004 | Feldman ........... 600/316 |
| 2004/0055898 A1 | 3/2004 | Heller et al. ........... 205/777.5 |
| 2004/0059256 A1 | 3/2004 | Perez ........... 600/583 |
| 2004/0060818 A1 | 4/2004 | Feldman ........... 204/403.01 |
| 2004/0061841 A1 | 4/2004 | Black ........... 355/30 |
| 2004/0064068 A1 | 4/2004 | DeNuzzio ........... 600/583 |
| 2004/0087990 A1 | 5/2004 | Boecker ........... 606/181 |
| 2004/0092842 A1 | 5/2004 | Boecker ........... 606/575 |
| 2004/0092994 A1 | 5/2004 | Briggs ........... 606/181 |
| 2004/0092995 A1 | 5/2004 | Boecker ........... 606/181 |
| 2004/0096991 A1 | 5/2004 | Zhang ........... 436/518 |
| 2004/0098009 A1 | 5/2004 | Boecker ........... 606/181 |
| 2004/0098010 A1 | 5/2004 | Davison ........... 606/181 |
| 2004/0102803 A1 | 5/2004 | Boecker ........... 606/183 |
| 2004/0106855 A1 | 6/2004 | Brown ........... 600/301 |
| 2004/0106858 A1 | 6/2004 | Say ........... 600/345 |
| 2004/0106859 A1 | 6/2004 | Say ........... 600/345 |
| 2004/0106860 A1 | 6/2004 | Say ........... 600/345 |
| 2004/0106904 A1 | 6/2004 | Gonnelli ........... 604/173 |
| 2004/0106941 A1 | 6/2004 | Roe ........... 606/181 |
| 2004/0107116 A1 | 6/2004 | Brown ........... 705/2 |
| 2004/0115754 A1 | 6/2004 | Chang ........... 435/14 |
| 2004/0115831 A1 | 6/2004 | Meathrel ........... 436/514 |
| 2004/0116780 A1 | 6/2004 | Brown ........... 600/300 |
| 2004/0116829 A1 | 6/2004 | Raney ........... 600/573 |
| 2004/0117207 A1 | 6/2004 | Brown ........... 705/2 |
| 2004/0117208 A1 | 6/2004 | Brown ........... 705/2 |
| 2004/0117209 A1 | 6/2004 | Brown ........... 705/2 |
| 2004/0117210 A1 | 6/2004 | Brown ........... 705/2 |
| 2004/0122339 A1 | 6/2004 | Roe |
| 2004/0127818 A1 | 7/2004 | Roe ........... 600/583 |
| 2004/0127819 A1 | 7/2004 | Roe ........... 600/583 |
| 2004/0127928 A1 | 7/2004 | Whitson ........... 606/181 |
| 2004/0127929 A1 | 7/2004 | Roe ........... 606/181 |
| 2004/0132167 A1 | 7/2004 | Rule ........... 435/287.1 |
| 2004/0133125 A1 | 7/2004 | Miyashita ........... 600/573 |
| 2004/0133127 A1 | 7/2004 | Roe ........... 600/583 |
| 2004/0137640 A1 | 7/2004 | Hirao ........... 436/514 |
| 2004/0138541 A1 | 7/2004 | Ward ........... 600/345 |
| 2004/0138588 A1 | 7/2004 | Saikley ........... 600/583 |
| 2004/0138688 A1 | 7/2004 | Giraud ........... 606/181 |
| 2004/0146958 A1 | 7/2004 | Bae ........... 435/14 |
| 2004/0154932 A1 | 8/2004 | Deng ........... 205/777.5 |
| 2004/0157017 A1 | 8/2004 | Mauze ........... 428/35.7 |
| 2004/0157149 A1 | 8/2004 | Hofmann ........... 430/131 |
| 2004/0157319 A1 | 8/2004 | Keen ........... 435/287.2 |
| 2004/0157338 A1 | 8/2004 | Burke ........... 436/147 |
| 2004/0157339 A1 | 8/2004 | Burke ........... 436/149 |
| 2004/0158137 A1 | 8/2004 | Eppstein ........... 600/347 |
| 2004/0158271 A1 | 8/2004 | Hamamoto ........... 606/181 |
| 2004/0161737 A1 | 8/2004 | Yang ........... 435/5 |
| 2004/0162473 A1 | 8/2004 | Sohrab ........... 600/345 |
| 2004/0162474 A1 | 8/2004 | Kiser ........... 600/345 |
| 2004/0162506 A1 | 8/2004 | Duchon ........... 600/583 |
| 2004/0162573 A1 | 8/2004 | Kheiri ........... 606/182 |
| 2004/0167383 A1 | 8/2004 | Kim ........... 600/365 |
| 2004/0171057 A1 | 9/2004 | Yang ........... 435/6 |
| 2004/0171968 A1 | 9/2004 | Katsuki ........... 600/583 |
| 2004/0172000 A1 | 9/2004 | Roe ........... 604/361 |
| 2004/0173472 A1 | 9/2004 | Jung ........... 205/777.5 |
| 2004/0173488 A1 | 9/2004 | Griffin ........... 206/363 |
| 2004/0176705 A1 | 9/2004 | Stevens ........... 600/584 |
| 2004/0176732 A1 | 9/2004 | Frazier ........... 604/345 |
| 2004/0178066 A1 | 9/2004 | Miyazaki ........... 204/403.01 |
| 2004/0178067 A1 | 9/2004 | Miyazaki ........... 204/403.1 |
| 2004/0178216 A1 | 9/2004 | Brickwood ........... 221/268 |

| | | | | | | |
|---|---|---|---|---|---|---|
| 2004/0180379 A1 | 9/2004 | van Duyne ............ 435/7.1 | 2004/0260325 A1 | 12/2004 | Kuhr ................ 606/181 |
| 2004/0182703 A1 | 9/2004 | Bell ................ 204/403.11 | 2004/0260326 A1 | 12/2004 | Lipoma ............. 606/182 |
| 2004/0185568 A1 | 9/2004 | Matsumoto ............ 436/8 | 2004/0260511 A1 | 12/2004 | Burke .............. 702/182 |
| 2004/0186359 A1 | 9/2004 | Beaudoin ............ 600/310 | 2004/0267105 A1 | 12/2004 | Monfre ............. 600/344 |
| 2004/0186394 A1 | 9/2004 | Roe .................. 600/598 | 2004/0267160 A9 | 12/2004 | Perez .............. 600/583 |
| 2004/0186500 A1 | 9/2004 | Koike ............... 606/181 | 2004/0267229 A1 | 12/2004 | Moerman ............ 604/500 |
| 2004/0193201 A1 | 9/2004 | Kim ................. 606/181 | 2004/0267299 A1 | 12/2004 | Kuriger ............ 606/181 |
| 2004/0193377 A1 | 9/2004 | Brown ............... 702/19 | 2004/0267300 A1 | 12/2004 | Mace ............... 606/182 |
| 2004/0194302 A1 | 10/2004 | Bhullar ............. 29/847 | 2005/0000806 A1 | 1/2005 | Hsieh .............. 203/403.1 |
| 2004/0197231 A1 | 10/2004 | Katsuki ............. 422/68.1 | 2005/0000807 A1 | 1/2005 | Wang ............... 204/403.81 |
| 2004/0197821 A1 | 10/2004 | Bauer ............... 437/7.1 | 2005/0000808 A1 | 1/2005 | Cui ................ 203/403.14 |
| 2004/0199062 A1 | 10/2004 | Petersson ........... 600/316 | 2005/0003470 A1 | 1/2005 | Nelson ............. 435/14 |
| 2004/0199409 A1 | 10/2004 | Brown ............... 705/3 | 2005/0004437 A1 | 1/2005 | Kaufmann ........... 600/300 |
| 2004/0200720 A1 | 10/2004 | Musho ............... 204/403.01 | 2005/0004494 A1 | 1/2005 | Perez .............. 600/583 |
| 2004/0200721 A1 | 10/2004 | Bhullar ............. 204/403.01 | 2005/0008537 A1 | 1/2005 | Mosolu ............. 422/56 |
| 2004/0202576 A1 | 10/2004 | Aceti ............... 422/82.05 | 2005/0008851 A1 | 1/2005 | Ezoe ............... 428/336 |
| 2004/0204662 A1 | 10/2004 | Perez ............... 600/583 | 2005/0009191 A1 | 1/2005 | Swenson ............ 436/43 |
| 2004/0206625 A1 | 10/2004 | Bhullar ............. 204/403.1 | 2005/0010090 A1 | 1/2005 | Acosta ............. 600/316 |
| 2004/0206636 A1 | 10/2004 | Hodges .............. 205/792 | 2005/0010093 A1 | 1/2005 | Ford ............... 600/345 |
| 2004/0206658 A1 | 10/2004 | Hammerstedt ......... 206/524.1 | 2005/0010134 A1 | 1/2005 | Douglas ............ 600/573 |
| 2004/0209307 A1 | 10/2004 | Valkirs ............. 435/7.1 | 2005/0010137 A1 | 1/2005 | Hodges ............. 600/583 |
| 2004/0209350 A1 | 10/2004 | Sakata .............. 435/287.1 | 2005/0010198 A1 | 1/2005 | Marchitto .......... 606/9 |
| 2004/0209354 A1 | 10/2004 | Mathies ............. 435/287.2 | 2005/0011759 A1 | 1/2005 | Moerman ............ 204/403.03 |
| 2004/0210279 A1 | 10/2004 | Gruzdev ............. 607/89 | 2005/0013731 A1 | 1/2005 | Burke .............. 422/56 |
| 2004/0211666 A1 | 10/2004 | Pamidi .............. 204/403.01 | 2005/0014997 A1 | 1/2005 | Ruchti ............. 600/310 |
| 2004/0214253 A1 | 10/2004 | Paek ................ 435/7.92 | 2005/0015020 A1 | 1/2005 | Levaughn ........... 600/583 |
| 2004/0215224 A1 | 10/2004 | Sakata .............. 606/181 | 2005/0016844 A1 | 1/2005 | Burke .............. 204/403.1 |
| 2004/0215225 A1 | 10/2004 | Nakayama ............ 606/182 | 2005/0019212 A1 | 1/2005 | Bhullar ............ 422/56 |
| 2004/0216516 A1 | 11/2004 | Sato ................ 73/64.56 | 2005/0019219 A1 | 1/2005 | Oshiman ............ 422/82.12 |
| 2004/0217019 A1 | 11/2004 | Cai ................. 205/792 | 2005/0019805 A1 | 1/2005 | Groll .............. 435/6 |
| 2004/0219500 A1 | 11/2004 | Brown ............... 434/307 R | 2005/0019945 A1 | 1/2005 | Groll .............. 436/169 |
| 2004/0219535 A1 | 11/2004 | Bell ................ 435/6 | 2005/0019953 A1 | 1/2005 | Groll .............. 436/514 |
| 2004/0220456 A1 | 11/2004 | Eppstein ............ 600/309 | 2005/0021066 A1 | 1/2005 | Kuhr ............... 606/181 |
| 2004/0220495 A1 | 11/2004 | Cahir ............... 600/562 | 2005/0027181 A1 | 2/2005 | Goode et al. | |
| 2004/0220564 A1 | 11/2004 | Ho .................. 606/47 | 2005/0027211 A1 | 2/2005 | Kuhr ............... 600/583 |
| 2004/0220603 A1 | 11/2004 | Rutynowski .......... 606/181 | 2005/0027562 A1 | 2/2005 | Brown .............. 705/2 |
| 2004/0222092 A1 | 11/2004 | Musho ............... 204/401 | 2005/0033341 A1 | 2/2005 | Vreeke ............. 606/181 |
| 2004/0224369 A1 | 11/2004 | Cai ................. 435/7.7 | 2005/0034983 A1 | 2/2005 | Chambers ........... 204/403.01 |
| 2004/0225230 A1 | 11/2004 | Liamos .............. 600/583 | 2005/0036020 A1 | 2/2005 | Li ................. 347/100 |
| 2004/0225311 A1 | 11/2004 | Levaughn ............ 606/181 | 2005/0036146 A1 | 2/2005 | Braig .............. 356/246 |
| 2004/0225312 A1 | 11/2004 | Orloff .............. 606/182 | 2005/0036906 A1 | 2/2005 | Nakahara et al. ....... 422/58 |
| 2004/0230216 A1 | 11/2004 | Levaughn ............ 606/181 | 2005/0036909 A1 | 2/2005 | Erickson ........... 422/61 |
| 2004/0231984 A1 | 11/2004 | Lauks ............... 204/416 | 2005/0037482 A1 | 2/2005 | Braig .............. 435/287 |
| 2004/0232009 A1 | 11/2004 | Okuda ............... 205/789 | 2005/0038329 A1 | 2/2005 | Morris ............. 600/319 |
| 2004/0236250 A1 | 11/2004 | Hodges .............. 600/583 | 2005/0038330 A1 | 2/2005 | Jansen ............. 600/345 |
| 2004/0236251 A1 | 11/2004 | Roe ................. 600/583 | 2005/0038463 A1 | 2/2005 | Davar .............. 606/181 |
| 2004/0236268 A1 | 11/2004 | Mitragotri .......... 604/20 | 2005/0038464 A1 | 2/2005 | Shraga ............. 606/182 |
| 2004/0236362 A1 | 11/2004 | Schraga ............. 606/181 | 2005/0038465 A1 | 2/2005 | Shraga ............. 606/182 |
| 2004/0238357 A1 | 12/2004 | Bhullar ............. 204/400 | 2005/0038674 A1 | 2/2005 | Braig .............. 705/2 |
| 2004/0238358 A1 | 12/2004 | Forrow et al. ....... 204/403 | 2005/0042766 A1 | 2/2005 | Ohman ............. 436/174 |
| 2004/0238359 A1 | 12/2004 | Ikeda ............... 204/403.1 | 2005/0043894 A1 | 2/2005 | Fernandez .......... 702/19 |
| 2004/0241746 A1 | 12/2004 | Adlassnig ........... 435/7.1 | 2005/0043965 A1 | 2/2005 | Heller ............. 705/2 |
| 2004/0242977 A1 | 12/2004 | Dosmann ............. 600/315 | 2005/0045476 A1 | 3/2005 | Neel ............... 204/403.2 |
| 2004/0243164 A1 | 12/2004 | D'Agostino .......... 606/181 | 2005/0049473 A1 | 3/2005 | Desai .............. 600/347 |
| 2004/0243165 A1 | 12/2004 | Koike ............... 606/181 | 2005/0050859 A1 | 3/2005 | Coppeta ............ 53/471 |
| 2004/0245101 A1 | 12/2004 | Willner ............. 204/403 | 2005/0054082 A1 | 3/2005 | Pachl .............. 435/287.2 |
| 2004/0248282 A1 | 12/2004 | Sobha ............... 435/287.2 | 2005/0059895 A1 | 3/2005 | Brown .............. 600/481 |
| 2004/0248312 A1 | 12/2004 | Vreeke .............. 436/95 | 2005/0060194 A1 | 3/2005 | Brown .............. 705/2 |
| 2004/0249254 A1 | 12/2004 | Racchini ............ 600/347 | 2005/0067280 A1 | 3/2005 | Reid ............... 204/403.14 |
| 2004/0249310 A1 | 12/2004 | Shartle ............. 600/583 | 2005/0067737 A1 | 3/2005 | Rappin ............. 264/272.19 |
| 2004/0249311 A1 | 12/2004 | Haar ................ 600/584 | 2005/0070771 A1 | 3/2005 | Rule ............... 600/316 |
| 2004/0249405 A1 | 12/2004 | Watanabe ............ 606/181 | 2005/0070819 A1 | 3/2005 | Poux ............... 600/576 |
| 2004/0249406 A1 | 12/2004 | Griffin ............. 606/182 | 2005/0070945 A1 | 3/2005 | Schraga ............ 606/182 |
| 2004/0251131 A1 | 12/2004 | Ueno ................ 204/403 | 2005/0072670 A1 | 4/2005 | Hasegawa ........... 204/403.01 |
| 2004/0253634 A1 | 12/2004 | Wang ................ 435/7.1 | 2005/0077176 A1 | 4/2005 | Hodges ............. 204/403.01 |
| 2004/0254434 A1 | 12/2004 | Goodnow ............. 600/365 | 2005/0077584 A1 | 4/2005 | Uhland ............. 257/414 |
| 2004/0254599 A1 | 12/2004 | Lipoma .............. 606/181 | 2005/0079542 A1 | 4/2005 | Cullen ............. 435/7.1 |
| 2004/0256228 A1 | 12/2004 | Huang ............... 204/434 | 2005/0080652 A1 | 4/2005 | Brown .............. 705/2 |
| 2004/0256248 A1 | 12/2004 | Burke ............... 205/792 | 2005/0085839 A1 | 4/2005 | Allen .............. 606/181 |
| 2004/0256685 A1 | 12/2004 | Chou ................ 257/414 | 2005/0085840 A1 | 4/2005 | Yi ................. 606/182 |
| 2004/0258564 A1 | 12/2004 | Charlton ............ 422/58 | 2005/0086083 A1 | 4/2005 | Brown .............. 705/2 |
| 2004/0260204 A1 | 12/2004 | Boecker ............. 600/584 | 2005/0090754 A1 | 4/2005 | Wolf ............... 600/509 |
| 2004/0260324 A1 | 12/2004 | Fukuzawa ............ 606/181 | 2005/0090850 A1 | 4/2005 | Toes ............... 606/182 |

| Pub. No. | Date | Inventor | Class |
|---|---|---|---|
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 600/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowicz | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Prausnitz et al. | 604/173 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Tang | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Salto | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/322 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Casey | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |

| Pub. No. | Date | Name | Ref. |
|---|---|---|---|
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olson | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |

| | | | | | |
|---|---|---|---|---|---|
| 2006/0231396 A1 | 10/2006 | Yamaoka ............... 204/403.14 | EP | 0368474 | 12/1995 |
| 2006/0231418 A1 | 10/2006 | Harding ..................... 205/775 | EP | 0461601 | 12/1995 |
| 2006/0231442 A1 | 10/2006 | Windus-Smith ............ 206/438 | EP | 0429076 | 1/1996 |
| 2006/0234369 A1 | 10/2006 | Sih ........................ 435/287.1 | EP | 0552223 | 7/1996 |
| 2006/0235284 A1 | 10/2006 | Lee ........................... 600/345 | EP | 0735363 | 10/1996 |
| 2006/0235454 A1 | 10/2006 | LeVaughn ................... 606/181 | EP | 0505504 | 3/1997 |
| 2006/0241517 A1 | 10/2006 | Fowler ....................... 600/583 | EP | 0406304 | 8/1997 |
| 2006/0241666 A1 | 10/2006 | Briggs ........................ 606/181 | EP | 0537761 | 8/1997 |
| 2006/0241667 A1 | 10/2006 | Freeman ..................... 606/181 | EP | 0795601 | 9/1997 |
| 2006/0241668 A1 | 10/2006 | Schraga ...................... 606/181 | EP | 0562370 | 11/1997 |
| 2006/0241669 A1 | 10/2006 | Stout .......................... 606/182 | EP | 0415393 | 12/1997 |
| 2006/0247554 A1 | 11/2006 | Roe ............................ 600/583 | EP | 0560336 | 5/1998 |
| 2006/0247555 A1 | 11/2006 | Harttig ....................... 600/584 | EP | 0 878 708 | 11/1998 |
| 2006/0247670 A1 | 11/2006 | LeVaughn ................... 606/181 | EP | 0 898 936 A2 | 3/1999 |
| 2006/0247671 A1 | 11/2006 | Levaughn ................... 606/182 | EP | 0505475 | 3/1999 |
| 2006/0259057 A1 | 11/2006 | Kim ........................... 606/181 | EP | 0901018 | 3/1999 |
| 2006/0259058 A1 | 11/2006 | Schiff ......................... 606/181 | EP | 0470649 | 6/1999 |
| 2006/0259060 A1 | 11/2006 | Whitson ..................... 606/182 | EP | 0 951 939 | 10/1999 |
| 2006/0264718 A1 | 11/2006 | Ruchti ........................ 600/310 | EP | 0 951 939 A2 | 10/1999 |
| 2006/0264996 A1 | 11/2006 | Levaughn ................... 606/181 | EP | 0847447 | 11/1999 |
| 2006/0264997 A1 | 11/2006 | Colonna ..................... 606/181 | EP | 0964059 | 12/1999 |
| 2006/0271083 A1 | 11/2006 | Boecker ..................... 606/181 | EP | 0969097 | 1/2000 |
| 2006/0271084 A1 | 11/2006 | Schraga ...................... 606/182 | EP | 0 985 376 | 5/2000 |
| 2006/0276724 A1 | 12/2006 | Freeman ..................... 600/583 | EP | 1021950 | 7/2000 |
| 2006/0277048 A1 | 12/2006 | Kintzig ....................... 704/275 | EP | 0894869 | 2/2001 |
| 2006/0278545 A1 | 12/2006 | Henning ..................... 206/363 | EP | 1074832 | 2/2001 |
| 2006/0282109 A1 | 12/2006 | Jansen ........................ 606/181 | EP | 1093854 | 4/2001 |
| 2006/0286620 A1 | 12/2006 | Werner ......................... 435/14 | EP | 1 101 443 | 5/2001 |
| 2006/0287664 A1 | 12/2006 | Grage ......................... 606/181 | EP | 1101443 | 5/2001 |
| 2006/0293577 A1 | 12/2006 | Morrison .................... 600/365 | EP | 1114995 | 7/2001 |
| 2007/0004989 A1 | 1/2007 | Dhillon ....................... 600/583 | EP | 0736607 | 8/2001 |
| 2007/0004990 A1 | 1/2007 | Kistner ....................... 600/583 | EP | 0874984 | 11/2001 |
| 2007/0007183 A1 | 1/2007 | Schulat ....................... 209/573 | EP | 0730037 | 12/2001 |
| 2007/0009381 A1 | 1/2007 | Schulat ......................... 422/58 | EP | 0636879 | 1/2002 |
| 2007/0010839 A1 | 1/2007 | Galloway ................... 606/167 | EP | 01174083 | 1/2002 |
| 2007/0010841 A1 | 1/2007 | Teo ............................. 606/181 | EP | 0851224 | 3/2002 |
| 2007/0015978 A1 | 1/2007 | Kanayama .................. 600/310 | EP | 0759553 | 5/2002 |
| 2007/0016079 A1 | 1/2007 | Freeman ..................... 600/476 | EP | 0856586 | 5/2002 |
| 2007/0016103 A1 | 1/2007 | Calasso ...................... 600/583 | EP | 0817809 | 7/2002 |
| 2007/0016104 A1 | 1/2007 | Jansen ........................ 600/583 | EP | 0872728 | 7/2002 |
| 2007/0038235 A1 | 2/2007 | Freeman et al. | EP | 0795748 | 8/2002 |
| 2007/0129650 A1 | 6/2007 | Freeman et al. | EP | 0685737 | 9/2002 |
| 2007/0142748 A1 | 6/2007 | Deshmukh et al. | EP | 0958495 | 11/2002 |
| 2007/0173741 A1 | 7/2007 | Deshmukh et al. | EP | 0937249 | 12/2002 |
| 2007/0276290 A1 | 11/2007 | Boecker et al. | EP | 0880692 | 1/2004 |
| 2008/0047764 A1 | 2/2008 | Lee et al. | EP | 01374770 | 1/2004 |
| 2008/0194987 A1 | 8/2008 | Boecker | EP | 1246688 | 5/2004 |
| | | | EP | 1502614 | 2/2005 |
| | FOREIGN PATENT DOCUMENTS | | FR | 2 555 432 A | 5/1985 |
| | | | GB | 2168815 | 6/1986 |
| DE | 29824204 | 10/2000 | GB | 233936 A | 6/1999 |
| DE | 10032042 | 1/2002 | GB | 2335860 A | 10/1999 |
| DE | 10057832 | 2/2002 | GB | 2335990 A | 10/1999 |
| DE | 10057832 C1 | 2/2002 | WO | WO 80/01389 | 7/1980 |
| DE | 10142232 | 3/2003 | WO | WO 85/04089 | 9/1985 |
| DE | 10208575 C1 | 8/2003 | WO | WO 86/07632 | 12/1985 |
| DE | 10245721 | 12/2003 | WO | WO 91/09139 | 6/1991 |
| DE | 10361560 A1 | 7/2005 | WO | WO 93/06979 | 4/1993 |
| EP | 0199484 A2 | 10/1986 | WO | WO 93/25898 | 12/1993 |
| EP | 0289 269 | 11/1988 | WO | WO 94/27140 | 11/1994 |
| EP | 0320109 | 6/1989 | WO | WO 94/29703 | 12/1994 |
| EP | 0 364 208 A1 | 4/1990 | WO | WO 94/29704 | 12/1994 |
| EP | 0170375 | 5/1990 | WO | WO 94/29731 | 12/1994 |
| EP | 0136362 | 12/1990 | WO | WO 95/00662 | 1/1995 |
| EP | 0453283 | 10/1991 | WO | WO 95/06240 | 3/1995 |
| EP | 0263948 | 2/1992 | WO | WO 95/10223 | 4/1995 |
| EP | 0374355 | 6/1993 | WO | WO 95/22597 | 8/1995 |
| EP | 0351891 | 9/1993 | WO | WO 96/30431 | 10/1996 |
| EP | 0593096 | 4/1994 | WO | WO 97/02359 | 1/1997 |
| EP | 0415388 | 5/1995 | WO | WO 97/02487 | 1/1997 |
| EP | 0505494 | 7/1995 | WO | WO 97/11883 A1 | 4/1997 |
| EP | 0359831 | 8/1995 | WO | WO 97/18464 | 5/1997 |
| EP | 0471986 | 10/1995 | WO | WO 97/30344 | 8/1997 |

| | | | | | |
|---|---|---|---|---|---|
| WO | WO 97/42882 | 11/1997 | WO | WO 02/41227 | 5/2002 |
| WO | WO 97/45720 | 12/1997 | WO | WO 02/41779 | 5/2002 |
| WO | WO 98/03431 | 1/1998 | WO | WO 02/44948 | 6/2002 |
| WO | WO 98/19159 | 5/1998 | WO | WO/0249507 | 6/2002 |
| WO | WO 98/20332 | 5/1998 | WO | WO 02/059734 | 8/2002 |
| WO | WO 98/20348 | 5/1998 | WO | WO 02/069791 | 9/2002 |
| WO | WO 98/24366 | 6/1998 | WO | WO 02/077638 | 10/2002 |
| WO | WO 98/24373 | 6/1998 | WO | WO 02/100251 | 12/2002 |
| WO | WO 98/35225 | 8/1998 | WO | WO 02/100252 | 12/2002 |
| WO | WO 99/03584 | 1/1999 | WO | WO 02/100253 | 12/2002 |
| WO | WO 99/05966 | 2/1999 | WO | WO 02/100254 | 12/2002 |
| WO | WO 99/07431 A1 | 2/1999 | WO | WO 02/100460 | 12/2002 |
| WO | WO 99/13100 | 3/1999 | WO | WO 02/100461 | 12/2002 |
| WO | WO 99/17854 | 4/1999 | WO | WO 02/101343 | 12/2002 |
| WO | WO 99/18532 | 4/1999 | WO | WO 02/101359 | 12/2002 |
| WO | WO 99/19507 | 4/1999 | WO | WO 03/000321 | 1/2003 |
| WO | WO 99/19717 | 4/1999 | WO | WO 03/023389 | 3/2003 |
| WO | WO 99/27483 | 6/1999 | WO | WO 03/042691 | 5/2003 |
| WO | WO 99/27852 | 6/1999 | WO | WO 03/045557 | 6/2003 |
| WO | WO 99/62576 | 12/1999 | WO | WO 03/046542 | 6/2003 |
| WO | WO 99/64580 | 12/1999 | WO | WO 03/049609 | 6/2003 |
| WO | WO 00/06024 | 2/2000 | WO | WO 03/050534 | 6/2003 |
| WO | WO 00/09184 | 2/2000 | WO | WO 03/066128 | 8/2003 |
| WO | WO 00/11578 | 3/2000 | WO | WO 03/070099 | 8/2003 |
| WO | WO 00/15103 | 3/2000 | WO | WO 03/071940 | 9/2003 |
| WO | WO 00/17799 | 3/2000 | WO | WO 03/082091 A2 | 10/2003 |
| WO | WO 00/17800 | 3/2000 | WO | WO 03/088851 A1 | 10/2003 |
| WO | WO 00/18293 | 4/2000 | WO | WO/03088834 | 10/2003 |
| WO | WO 00/19346 | 4/2000 | WO | WO 03/094752 | 11/2003 |
| WO | WO 00/30186 | 5/2000 | WO | WO 03/101297 | 12/2003 |
| WO | WO 00/32097 | 6/2000 | WO | WO 04/008130 | 1/2004 |
| WO | WO 00/32098 | 6/2000 | WO | WO 2004/022133 | 3/2004 |
| WO | WO 00/33236 | 6/2000 | WO | WO 04/026130 | 4/2004 |
| WO | WO 00/39914 | 7/2000 | WO | WO 04/041082 | 5/2004 |
| WO | WO 00/42422 | 7/2000 | WO | WO 2004/040285 A2 | 5/2004 |
| WO | WO 00/44084 | 7/2000 | WO | WO 2004/040287 A1 | 5/2004 |
| WO | WO 00/50771 | 8/2000 | WO | WO 2004/040948 | 5/2004 |
| WO | WO 00/60340 | 10/2000 | WO | WO 2004/054455 | 7/2004 |
| WO | WO 00/64022 | 10/2000 | WO | WO 2004/060174 | 7/2004 |
| WO | WO 00/67245 | 11/2000 | WO | WO 2004/060446 | 7/2004 |
| WO | WO 00/67268 | 11/2000 | WO | WO 2004/091693 | 10/2004 |
| WO | WO 00/72452 | 11/2000 | WO | WO 2004/098405 | 11/2004 |
| WO | WO 01/00090 | 1/2001 | WO | WO 2004/003147 | 12/2004 |
| WO | WO 01/15807 | 3/2001 | WO | WO 2004/107964 | 12/2004 |
| WO | WO 01/16578 A1 | 3/2001 | WO | WO 2004/107975 | 12/2004 |
| WO | WO 01/75433 | 3/2001 | WO | WO 2004/112602 | 12/2004 |
| WO | WO 01/23885 | 4/2001 | WO | WO 2004/112612 A1 | 12/2004 |
| WO | WO 01/25775 | 4/2001 | WO | WO 2005/001418 | 1/2005 |
| WO | WO 01/26813 | 4/2001 | WO | WO 2005/006939 | 1/2005 |
| WO | WO 01/33216 | 5/2001 | WO | WO 2005/011774 | 2/2005 |
| WO | WO 01/34029 | 5/2001 | WO | WO 2005/016125 | 2/2005 |
| WO | WO 01/36955 | 5/2001 | WO | WO 2005/018425 | 3/2005 |
| WO | WO 01/37174 | 5/2001 | WO | WO 2005/018430 | 3/2005 |
| WO | WO 01/45014 A1 | 6/2001 | WO | WO 2005/018454 | 3/2005 |
| WO | WO 01/40788 | 7/2001 | WO | WO 2005/018709 | 3/2005 |
| WO | WO 01/57510 | 8/2001 | WO | WO 2005/018710 | 3/2005 |
| WO | WO 01/64105 | 9/2001 | WO | WO 2005/018711 | 3/2005 |
| WO | WO 01/66010 | 9/2001 | WO | WO 2005/022143 | 3/2005 |
| WO | WO 01/69505 | 9/2001 | WO | WO 2005/023088 | 3/2005 |
| WO | WO 01/72220 A | 10/2001 | WO | WO 2005/033659 | 4/2005 |
| WO | WO 01/72225 | 10/2001 | WO | WO 2005/034720 | 4/2005 |
| WO | WO 01/73124 | 10/2001 | WO | WO 2005/034721 | 4/2005 |
| WO | WO 01/73395 | 10/2001 | WO | WO 2005/034741 | 4/2005 |
| WO | WO 01/89691 | 11/2001 | WO | WO 2005/034778 | 4/2005 |
| WO | WO 02/00101 | 1/2002 | WO | WO 2005/035017 | 4/2005 |
| WO | WO 02/02796 | 1/2002 | WO | WO 2005/035018 | 4/2005 |
| WO | WO 02/08750 | 1/2002 | WO | WO 2005/037095 | 4/2005 |
| WO | WO 02/08753 | 1/2002 | WO | WO 2005/046477 | 5/2005 |
| WO | WO 02/08950 | 1/2002 | WO | WO 2005/065399 | 7/2005 |
| WO | WO 02/18940 | 3/2002 | WO | WO 2005/065414 | 7/2005 |
| WO | WO 02/21317 | 3/2002 | WO | WO 2005/065415 | 7/2005 |
| WO | WO 02/25551 | 3/2002 | WO | WO 2006005545 A2 | 7/2005 |
| WO | WO 02/32559 | 4/2002 | WO | WO 2005/072604 | 8/2005 |

| | | | | | |
|---|---|---|---|---|---|
| WO | WO 2005/084557 | 9/2005 | WO | WO 2006/001973 | 1/2006 |
| WO | WO 2005/104948 A1 | 11/2005 | WO | WO 2006/011062 | 2/2006 |
| WO | WO 2005/116622 | 12/2005 | WO | WO 2006/013045 | 2/2006 |
| WO | WO 2005/119234 | 12/2005 | WO | WO 2006/027702 A2 | 3/2006 |
| WO | WO 2005/120365 A1 | 12/2005 | WO | WO 2006/032391 | 3/2006 |
| WO | WO 2005/121759 | 12/2005 | WO | WO 2006/072004 | 7/2006 |

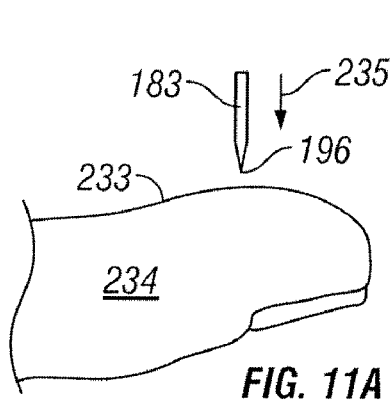
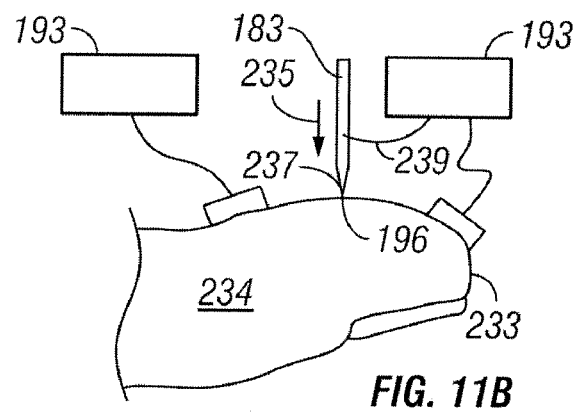
FIG. 11A        FIG. 11B
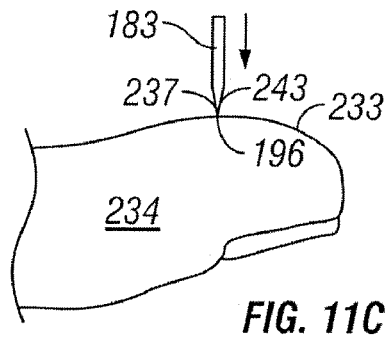
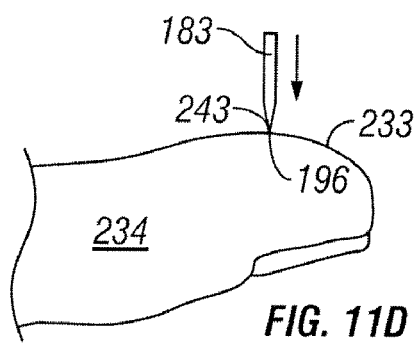
FIG. 11C        FIG. 11D
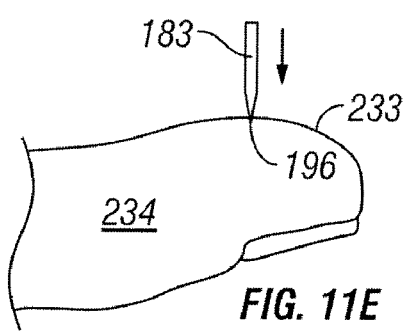
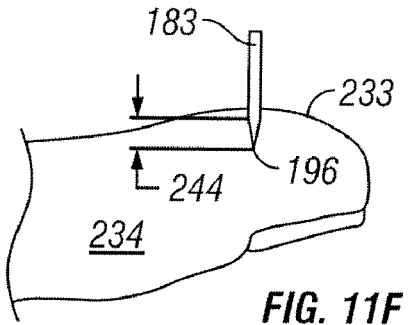
FIG. 11E        FIG. 11F
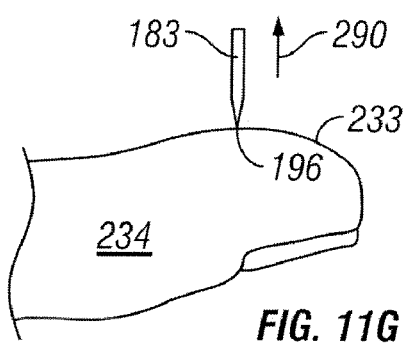
FIG. 11G Time effect: s Sensitivity to variation

| Controller | I/O system | | Physical system | |
|---|---|---|---|---|
| Controller<br>Entry Speed<br>Energy Set Point<br>Brake Assist Gain<br>LUT Resolution<br>Under design control | Encoder<br>Resolution<br>Noise<br><br>Under design control,<br>variable in mfr | | Carriage<br>Mass<br>Initial Position<br>Limit Position<br><br>Under design control | Launcher<br>*stiction*<br>*pull-out force*<br>*dynamic friction*<br><br>Known, variable in mfr |
| Coil model<br>Peak force<br>Centre<br>*Coil switch points*<br>Under design control,<br>experimentally based | PWM<br>Period<br>Resolution<br>*Force rise time*<br>Under design control | | Coil<br>Peak force<br>Centre<br>*Coil switch points*<br>*Force rise time*<br>Under design control,<br>variable in mfr | Skin<br>force gain<br>noise<br>offset<br>*stiction*<br>Unknown - variable in use |
| Skin model<br>force gain<br>noise<br>offset<br>*stiction*<br>Under design control,<br>experimentally based | | | | | bold modeled in sensitivity analysis
*italic* *variable - not yet modelled*
plain text under design control

*FIG. 39*

Coil Usage

Effect on Stopping accuracy of variation in predicted skin force gain of / 2x

METHOD AND APPARATUS FOR BODY FLUID SAMPLING AND ANALYTE SENSING

BACKGROUND OF THE INVENTION

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Another impediment to patient compliance is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of attempts required by a patient to successfully generate spontaneous blood flow. Different skin thickness may yield different results in terms of pain perception, blood yield and success rate of obtaining blood between different users of the lancing device. Known devices poorly account for these skin thickness variations.

Variations in skin thickness including the stratum corneum and hydration of the epidermis can yield different results between different users. Spontaneous blood droplet generation is dependent on reaching the blood capillaries and venuoles, which yield the blood sample. It is therefore an issue of correct depth of penetration of the cutting device. Due to variations in skin thickness and hydration, some types of skin will deform more before cutting starts, and hence the actual depth of penetration will be less, resulting in less capillaries and venuoles cut and less spontaneous blood generation.

Known lancing devices fail to provide accurate sensing of lancet position. Thus they do not know exactly how far the penetrating member has cut into the tissue. This lack of position sensing is one reason for more painful lancing associated with known fluid sampling devices.

Additionally, known lancing devices fail to have sufficiently accurate control of lancet position and velocity to achieve a spontaneous blood generation in a relatively pain free manner.

SUMMARY OF THE INVENTION

The present invention provides solutions for at least some of the drawbacks discussed above. The technical field relates to the lancing of the finger to obtain a body fluid or blood sample for the analysis of that sample. Because the penetration distance is a strong predictor of the success of the lancing event for spontaneous blood generation, the ability of the device to accurately control this distance is of interest. Specifically, some embodiments of the present invention provide an improved body fluid sampling device. For some embodiments of penetrating member drivers, the invention provides improved methods for controlling the velocity and cutting efficient of a penetrating member. At least some of these and other objectives described herein will be met by embodiments of the present invention.

In one aspect, the present invention provides improved lancing devices operating with adaptive control algorithms. Because of the very high speeds that embodiments of the present invention may move their penetrating members, feedback control may not be sufficient, due to the short amount of time available. In one embodiment, the present invention provides desired parameters, based on the models of the penetrating member, the penetrating member driver, and the targeted tissue. Based on this model, the system may have predictive information stored in lookup tables on how to drive the penetrating member driver and when to apply braking force so that the device performs as desired to arrive at a desired depth and to provide a desired level of cutting efficiency and/or performance.

In one embodiment, a method of controlling a penetrating member is provided. The method comprises providing a lancing device having a penetrating member driver with a position sensor and a processor that can determine the relative position and velocity of the penetrating member based on measuring relative position of the penetrating member with respect to time; providing a look up table having desired velocity trajectory based on empirical data; and using control to adjust lancet velocity to maintain penetrating member velocity along said trajectory.

In another embodiment, the present invention relates to the way that an electronically driven lancing device controls the trajectory of the inbound lancet up to the point of maximum extension or penetration into a target tissue. This is the point of maximum penetration of the lancet into the skin. This embodiment of the present invention comprises a control algorithm, that when combined with the necessary hardware to execute the control instructions, increases the depth accuracy of the penetrating member. The present invention also provides improved cutting efficiency by providing lancet behavior that is optimized for cutting tissue.

In one aspect, the present invention involves learning through testing what the ideal setup parameters are and then using more complicated feedback systems to get results similar to a feed-forward system.

In other aspects, the present invention may involve manual braking, braking with zero residual energy, braking only, preserving acceleration, and appropriate force for smart braking.

The system may further comprise means for coupling the force generator with one of the penetrating members.

The system may further comprise a penetrating member sensor positioned to monitor a penetrating member coupled to the force generator, the penetrating member sensor configured to provide information relative to a depth of penetration of a penetrating member through a skin surface.

The depth of penetration may be about 100 to 2500 microns.

The depth of penetration may be about 500 to 750 microns.

The depth of penetration may be, in this nonlimiting example, no more than about 1000 microns beyond a stratum corneum thickness of a skin surface.

The depth of penetration may be no more than about 500 microns beyond a stratum corneum thickness of a skin surface.

The depth of penetration may be no more than about 300 microns beyond a stratum corneum thickness of a skin surface.

The depth of penetration may be less than a sum of a stratum corneum thickness of a skin surface and 400 microns.

The penetrating member sensor may be further configured to control velocity of a penetrating member.

The active penetrating member may move along a substantially linear path into the tissue.

The active penetrating member may move along an at least partially curved path into the tissue.

The driver may be a voice coil drive force generator.

The driver may be a rotary voice coil drive force generator.

The penetrating member sensor may be coupled to a processor with control instructions for the penetrating member driver.

The processor may include a memory for storage and retrieval of a set of penetrating member profiles utilized with the penetrating member driver.

The processor may be utilized to monitor position and speed of a penetrating member as the penetrating member moves in a first direction.

The processor may be utilized to adjust an application of force to a penetrating member to achieve a desired speed of the penetrating member.

The processor may be utilized to adjust an application of force to a penetrating member when the penetrating member contacts a target tissue so that the penetrating member penetrates the target tissue within a desired range of speed.

The processor may be utilized to monitor position and speed of a penetrating member as the penetrating member moves in the first direction toward a target tissue, wherein the application of a launching force to the penetrating member is controlled based on position and speed of the penetrating member.

The processor may be utilized to control a withdraw force to the penetrating member so that the penetrating member moves in a second direction away from the target tissue.

In the first direction, the penetrating member may move toward the target tissue at a speed that is different than a speed at which the penetrating member moves away from the target tissue.

In the first direction the penetrating member may move toward the target tissue at a speed that is greater than a speed at which the penetrating member moves away from the target tissue.

The speed of a penetrating member in the first direction may be the range of about 2.0 to 10.0 m/sec.

The average velocity of the penetrating member during a tissue penetration stroke in the first direction may be about 100 to about 1000 times greater than the average velocity of the penetrating member during a withdrawal stroke in a second direction.

A further understanding of the nature and advantages of the invention will become apparent by reference to the remaining portions of the specification and drawings.

BRIEF DESCRIPTION OF THE DRAWINGS

FIGS. 11A-11G shows a method of penetrating tissue.

FIGS. 31-43 show various graphs of penetrating member performance and control schematics.

DESCRIPTION OF THE SPECIFIC EMBODIMENTS

The present invention provides a multiple analyte detecting member solution for body fluid sampling. Specifically, some embodiments of the present invention provides a multiple analyte detecting member and multiple penetrating member solution to measuring analyte levels in the body. The invention may use a high density design. It may use penetrating members of smaller size, such as but not limited to diameter or length, than known lancets. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It must be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
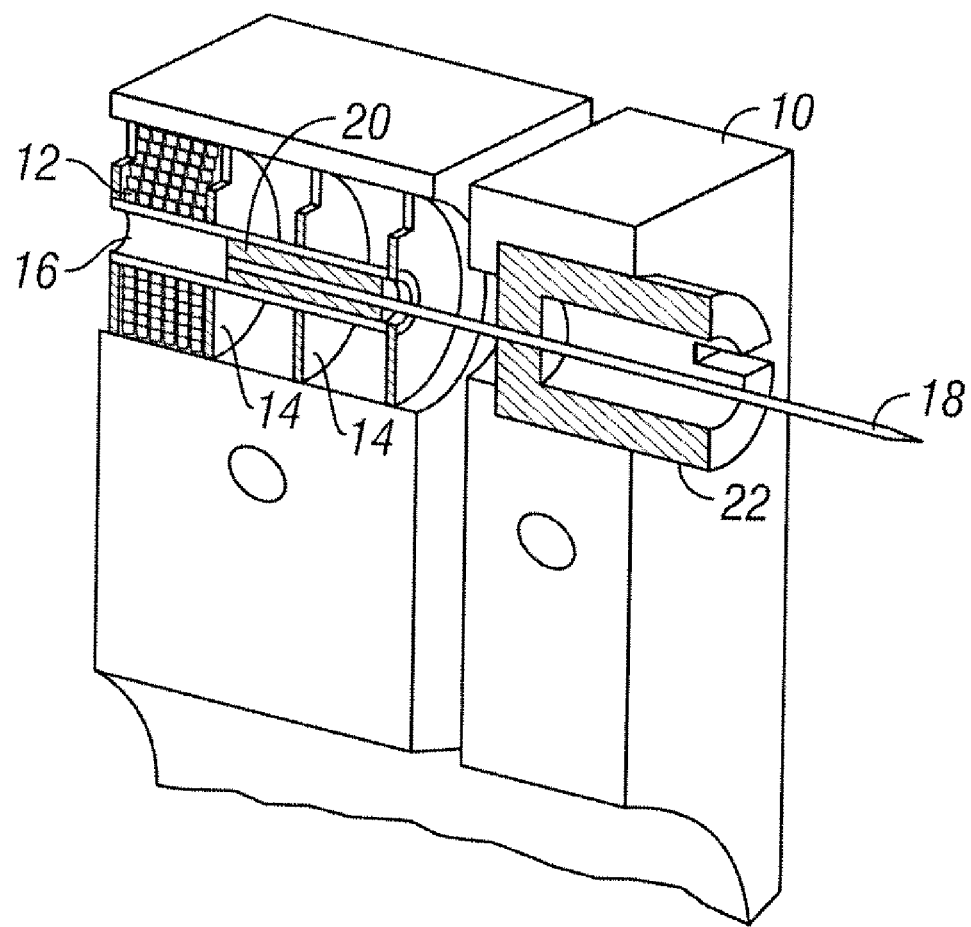
FIG. 1 illustrates an embodiment of a controllable force driver in the form of a cylindrical electric penetrating member driver using a coiled solenoid-type configuration.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

Figure 2A:
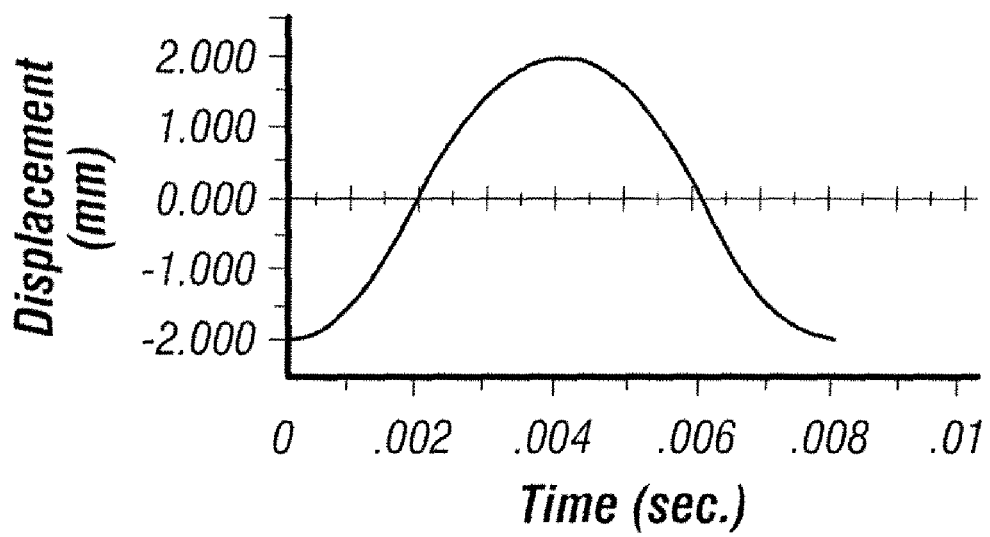
FIG. 2A illustrates a displacement over time profile of a penetrating member driven by a harmonic spring/mass system.
Figure 2B:
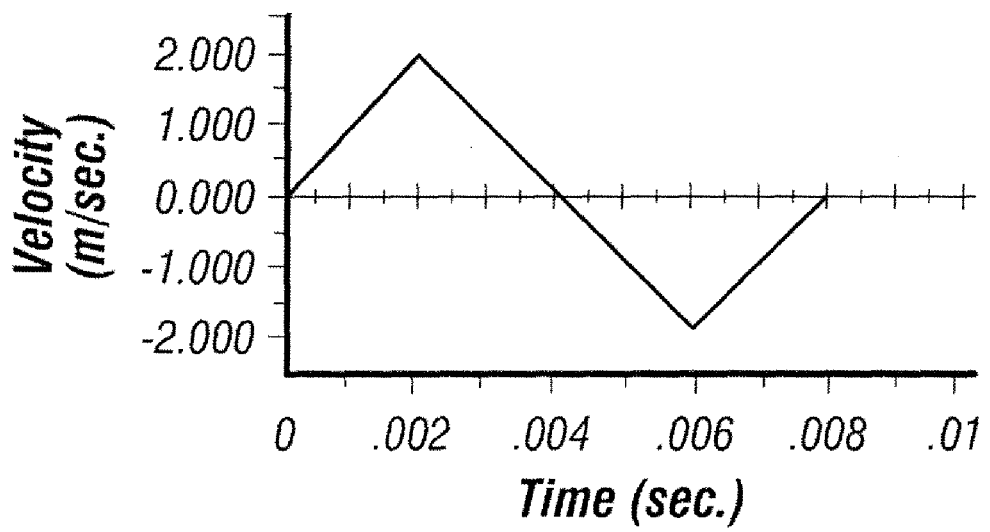
FIG. 2B illustrates the velocity over time profile of a penetrating member driver by a harmonic spring/mass system.
Figure 2C:
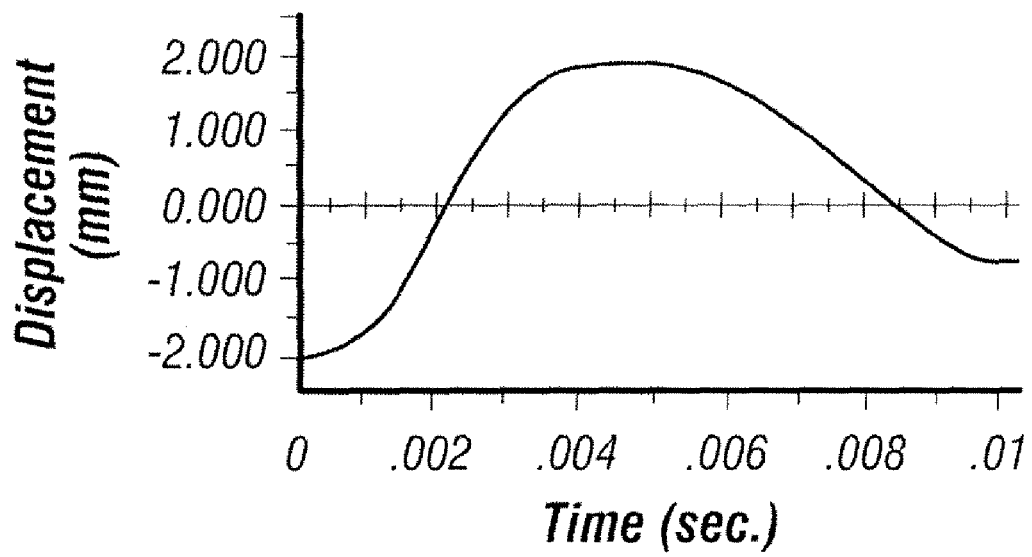
FIG. 2C illustrates a displacement over time profile of an embodiment of a controllable force driver.
Figure 2D:
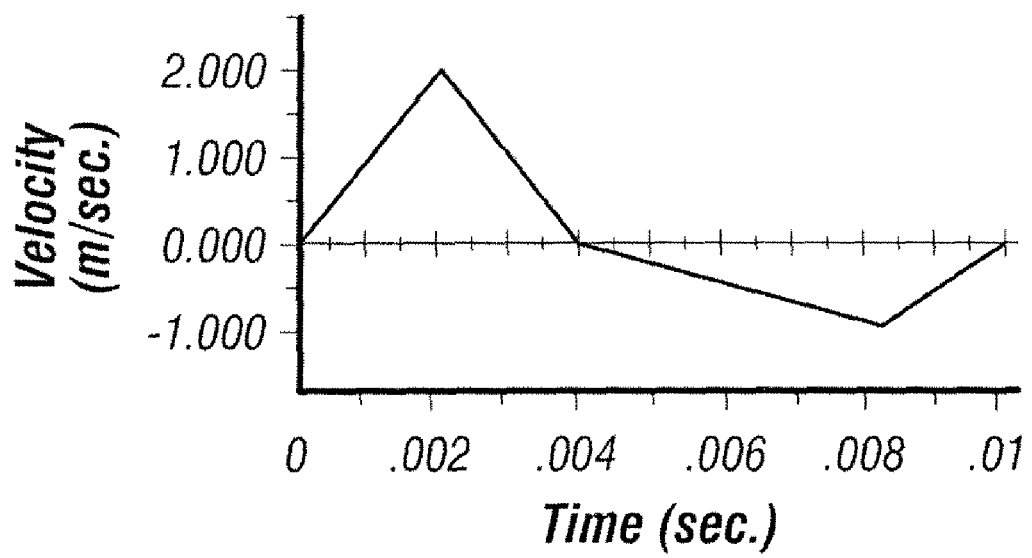
FIG. 2D illustrates a velocity over time profile of an embodiment of a controllable force driver.
Figure 3:
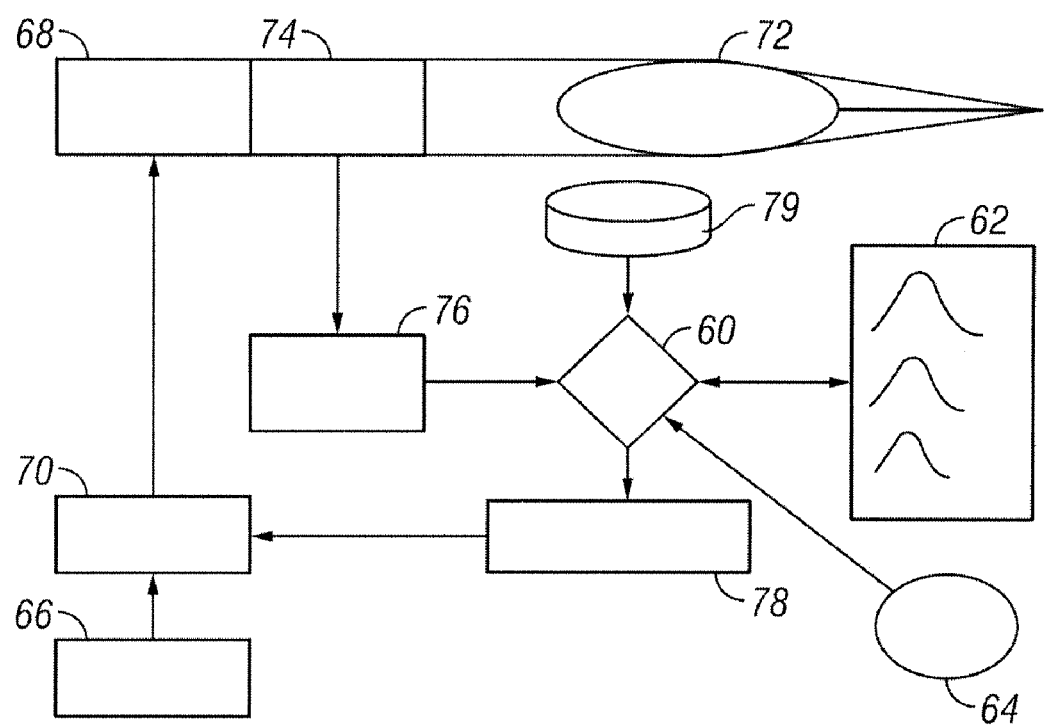
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member as shown in FIGS. 2 and 3. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in FIG. 2C which illustrates an embodiment of a controlled displacement profile and FIG. 2D which illustrates an embodiment of a the controlled velocity profile. These are compared to FIGS. 2A and 2B, which illustrate embodiments of displacement and velocity profiles, respectively, of a harmonic spring/mass powered driver. Reduced pain can be achieved by using impact velocities of greater than about 2 mls entry of a tissue penetrating element, such as a lancet, into tissue. Other suitable embodiments of the penetrating member driver are described in commonly assigned, U.S. Pat. No. 7,025,774 previously incorporated herein.

In one embodiment, a controllable force driver is used to drive a penetrating member and can be powered by electromagnetic energy. A controllable driver can achieve a desired velocity versus position profile. The driver is coupled to a processor and a penetrating member driver to control depth of penetration, to control penetrating member penetration and withdrawal velocity, and therefore reduce the pain perceived when cutting into the skin. Embodiments of the invention include a controllable driver that can be used with a feedback loop with a position sensor to control the power delivered to the lancet, which can optimize the velocity and displacement profile to compensate for variations in skin thickness.

The electromagnetic driver allows programmable control over the velocity vs. position profile of the entire lancing process including timing the start of the lancet, tracking the lancet position, measuring the lancet velocity, controlling the distal stop acceleration, and controlling the skin penetration depth.

In one embodiment, The electromagnetic driver has a moving part comprising a lancet assembly with a penetrating member and a magnetically permeable flag attached at the proximal or drive end and a stationary part comprising a stationary housing assembly with electric field coils arranged so that they produce a balanced field at the flag to reduce or eliminate any net lateral force on the flag. The electric field coils are generally one or more metal coils, which generate a magnetic field when electric current passes through the coil. The iron flag is a flat or enlarged piece of magnetic material, which increases the surface area of the penetrating member assembly to enhance the magnetic forces generated between the proximal end of the penetrating member and a magnetic field produced by the field coils. The combined mass of the penetrating member and the iron flag can be minimized to facilitate rapid acceleration for introduction into the skin of a patient, to reduce the impact when the penetrating member stops in the skin, and to facilitate prompt velocity profile changes throughout the sampling cycle.

FIG. 3 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned U.S. Pat. No. 7,025,774, previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

In one embodiment, a penetrating member device includes a controllable driver coupled to a penetrating member. The penetrating member device has a penetrating member coupled to an elongate coupler shaft by a drive coupler. The elongate coupler shaft has a proximal end and a distal end. A driver coil sack is disposed about the elongate coupler shaft proximal of the penetrating member. A position sensor is disposed about a proximal portion of the elongate coupler shaft and an electrical conductor electrically couples a processor to the position sensor. The elongate coupler shaft is driven by a driver coil pack, controlled by the position sensor and processor coupled to the controllable driver, and by way of illustration and without limitation, a controllable electromagnetic driver.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 microliter volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
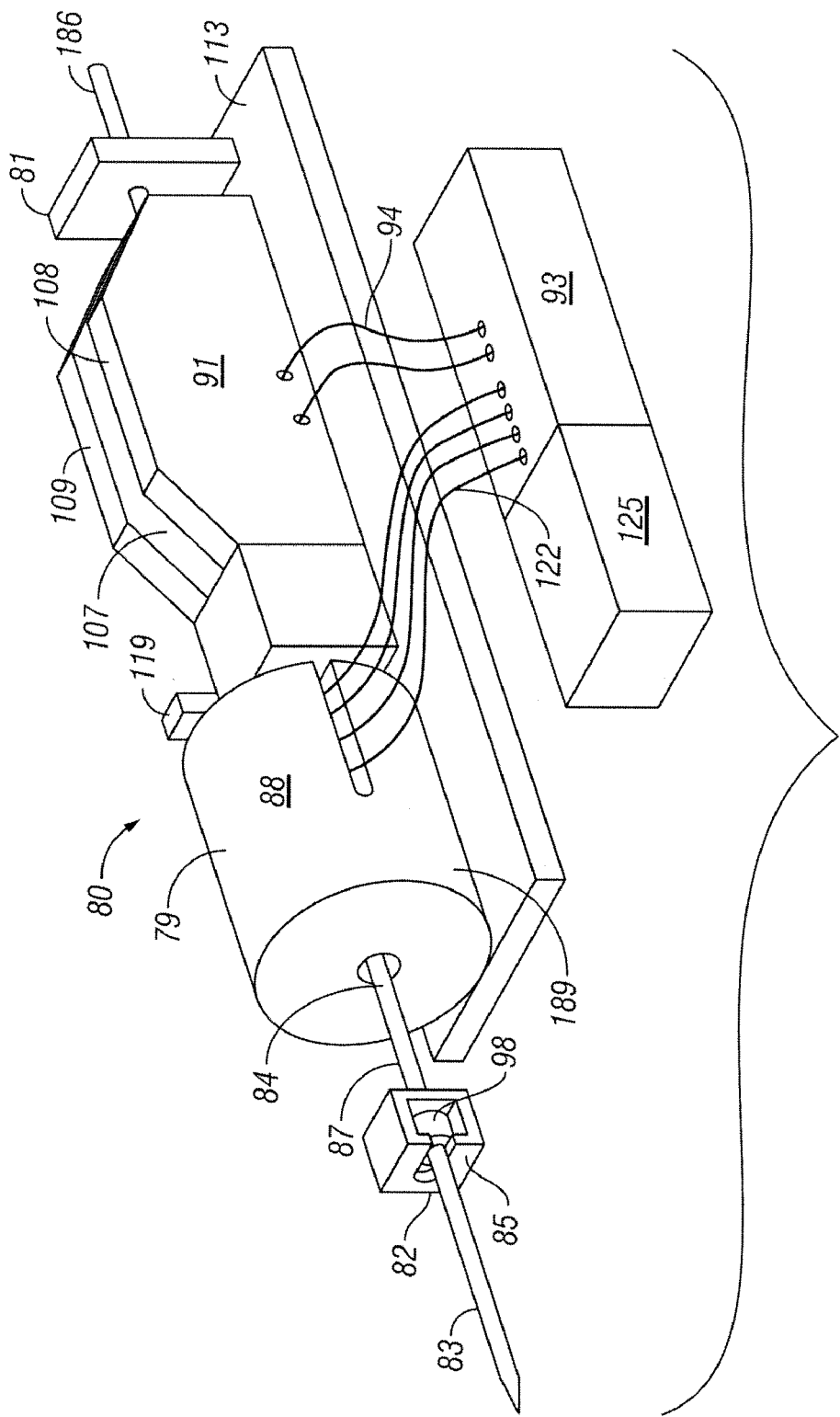
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
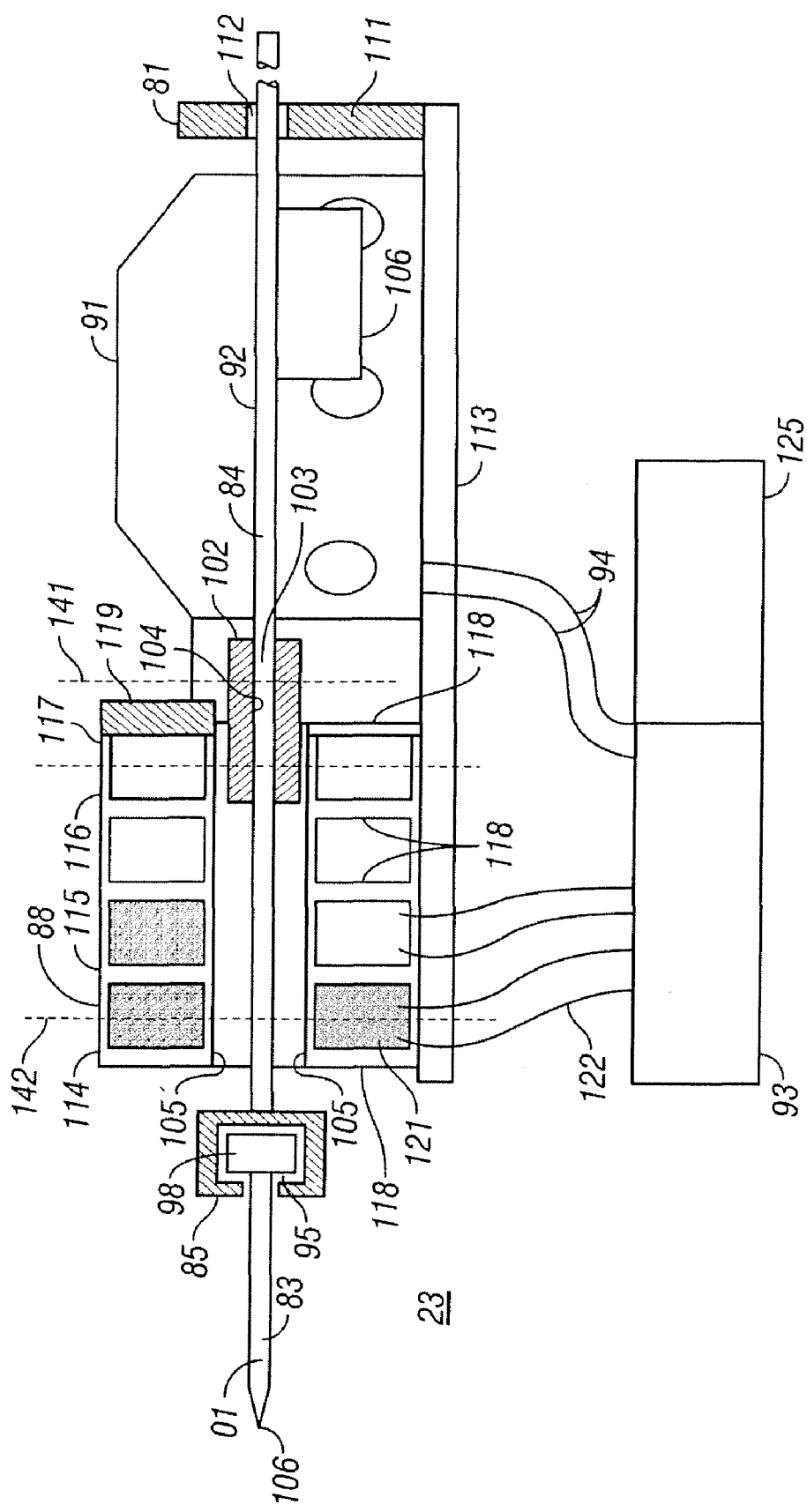
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 108 and 109 in a predetermined manner. The interaction of the optical beams generated by the LEDs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

In another aspect of the present invention, this solution involves using two measurements, tenting and force present at the front end of the lancing device 200, to interpolate the stratum corneum (SC) thickness at that particular skin location. It is known that force applied to the front end of a lancing device affects the amount of tenting caused by an inbound lancet. This effect can be visualized by plotting force vs. tenting on a linear scale. Varying Stratum Corneum thickness causes a change in the slope of this curve. This data can be used to interpolate an SC thickness value.

Figure 6:
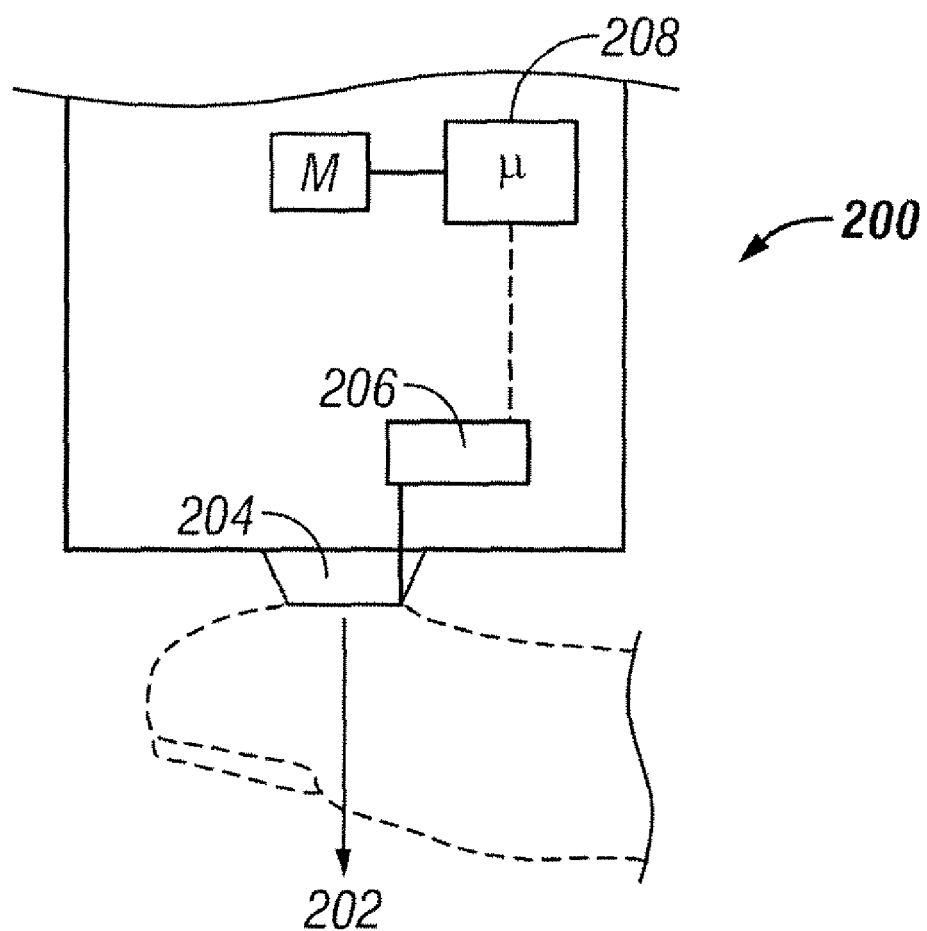
FIG. 6 shows one embodiment of the present invention with a front end and landing a target tissue.
Figure 7A:
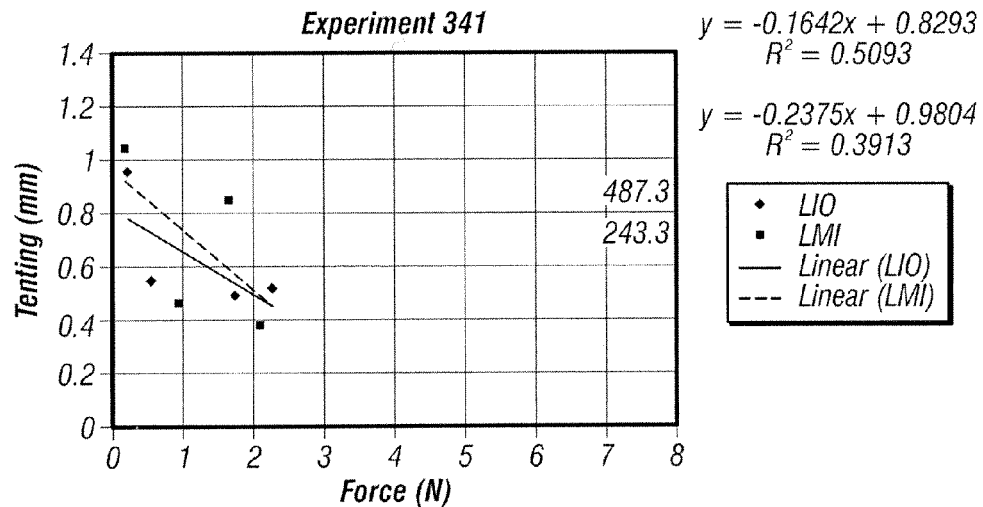
FIG. 7 are graphs showing tenting and force related to a lancing event.
Figure 7B:
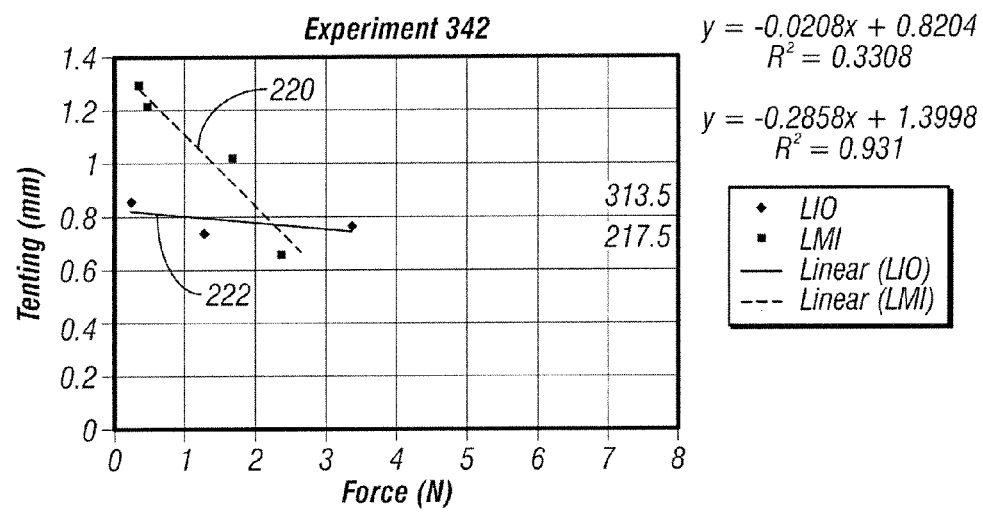
Figure 7C:
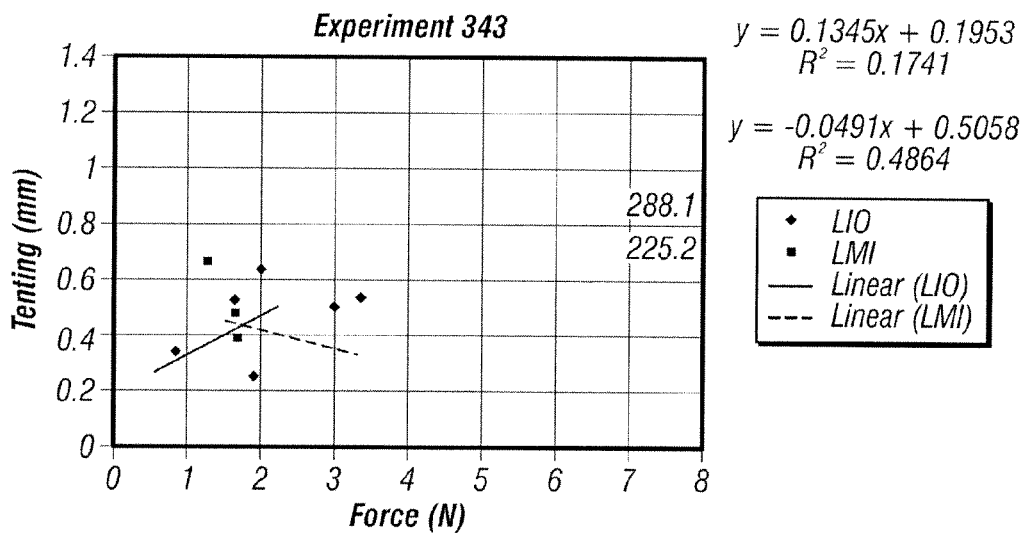
Figure 7D:
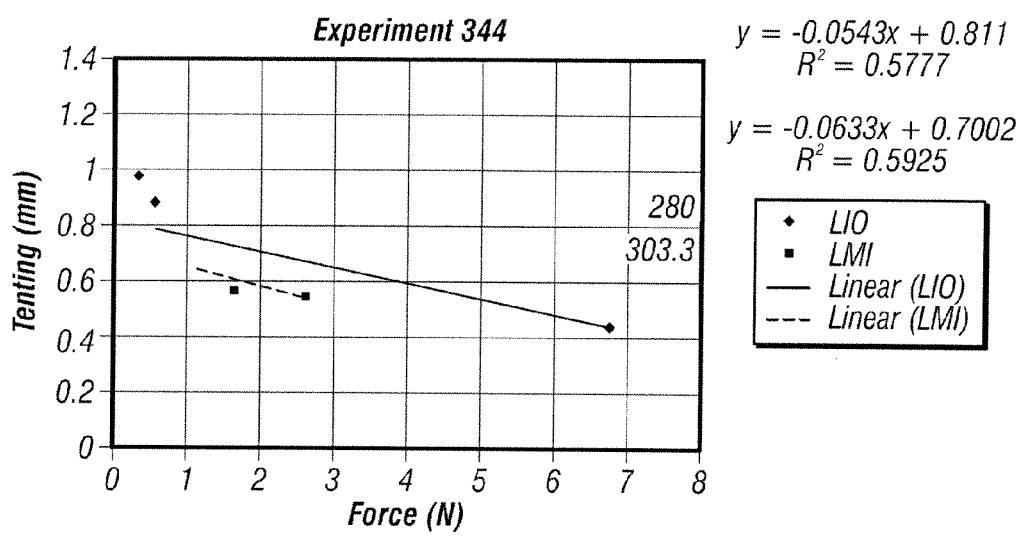

Referring now to FIG. 6, one embodiment of a lancing device 200 is shown. The arrow 202 indicates that a penetrating member will move outward to penetrate tissue. A finger (shown in phantom) will press against the front end 204 which is coupled to a pressure transducer 206. This may in turn be coupled to a processor 208. The pressure transducer 206 may be any one known in the art such as but not limited to a strain gauge or a piezoelectric sensor. The processor 208 may be coupled to memory M that stores readings.

Referring now to FIG. 7, experiment 342 shows that there are two different slopes 220 and 222 for different SC thicknesses. Line 222 corresponds to the thicker (313) SC while line 220 corresponds to the thinner (217) SC. Thus in the lancing device 200, by recording the force (which will undoubtably vary) applied by the user and the tenting, the SC thickness can be determined based on the slope of the line. Methods for determining tenting are discussed in commonly assigned, copending U.S. patent application Ser. No. 60/476,584 may be used with the present invention. It should be understood that this information may be stored into the memory. The location used to lance may also be stored into memory M so that measurements for specific sites may be grouped together.

It should be understood that the present invention relates to the way that an electronically driven lancing device controls the trajectory of the inbound lancet up to the point of maximum extension. This is the point of maximum penetration of the lancet into the skin. In one embodiment, the invention comprises a control algorithm, that when combined with the suitable hardware to execute the control instructions, increases the depth accuracy. The present application also describes the method of a quiet phase but only refers to traditional braking adjustment after this phase. The present application also describes the idea of setting the contact velocity at a rate where coil activity is minimized and the control system "operates within a projected trajectory."

Figure 8:
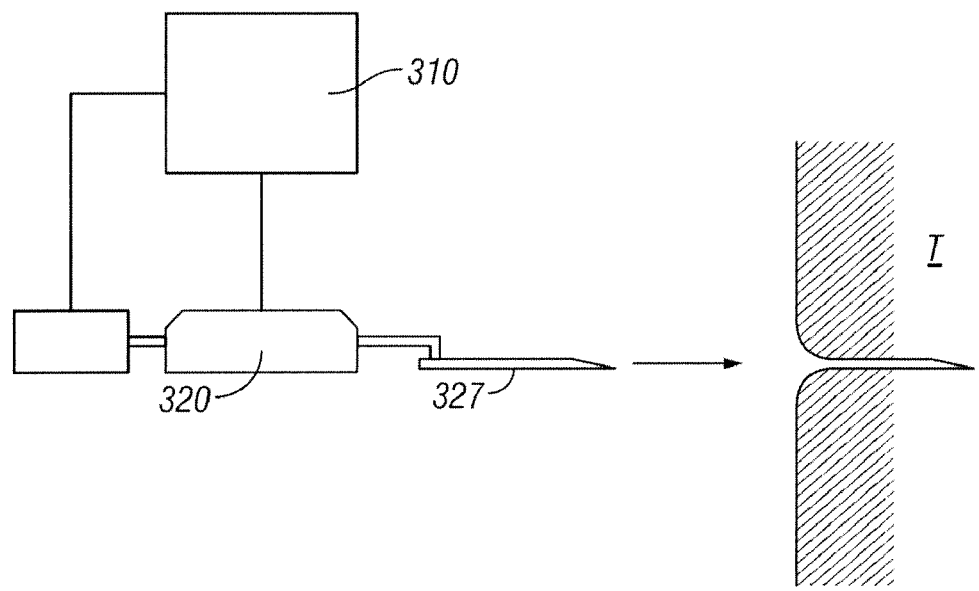
FIG. 8-9 show schematics for a tissue penetrating device.

Referring now to FIG. 8, one method of penetrating member control will be described. The method of lancing starts with the penetrating member control system 310 that is coupled to an electric drive mechanism 320 used to accelerate the penetrating member 322 to a desired speed toward a target tissue T. The penetrating member 322 hits the skin at a relative point and then there is a switch when the penetrating member 322 reaches a certain displacement. The control system will cause the braking to come on. And then braking will happen really kind of a nondeterministic way. The brakes are on, it goes to a certain depth. There is not an interactiveness with the control system as to where the member 322 is at, as to where it needs to be (from the point the braking switches on). The variance of where the member 322 is and where it wants to be is could be improved.

Figure 9:
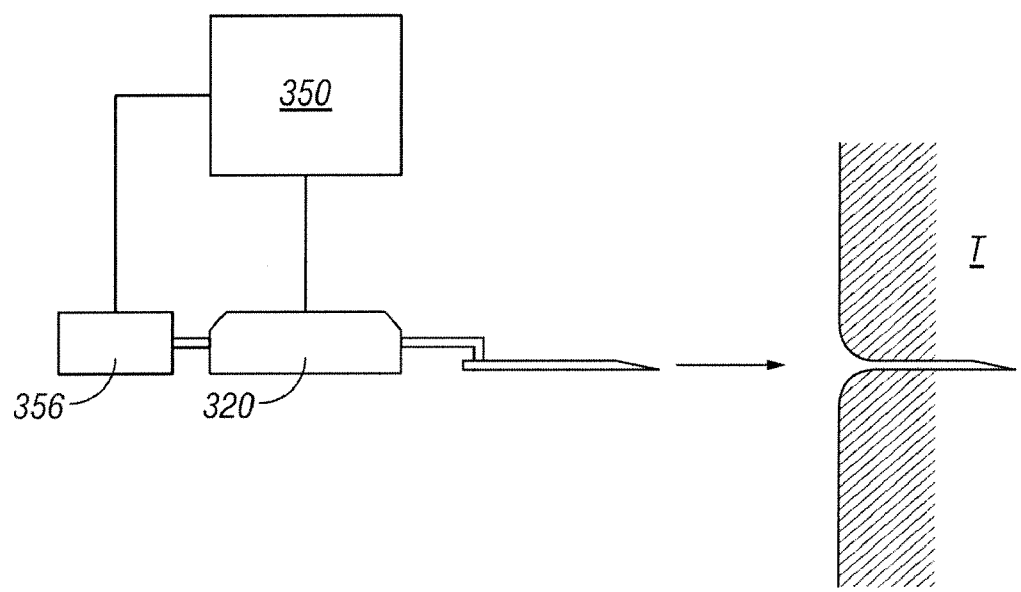

Referring now to FIG. 9, with the present invention using one embodiment of what is termed "smart braking", an adaptive control system 350 may be used to improve performance. Such a system 350 has the ability to redirect braking during the braking period to get to the member 322 to the appropriate depth desired. In one embodiment, it is not necessarily a full-on braking up to the point of reversal in a binary manner (i.e. either full on or full off).

In one embodiment of adaptive control system 350, variable braking force, which is computationally more complex, may be used. In one embodiment, for each duty cycle that the penetrating member 322 is braking, the system 350 will look where the member 322 is, and where it should be. There may be a look up table used to determine if the member 322 is under or over the place where the member 322 wants to be for a particular part of the braking cycle. The control system 350 can redirect or adjust braking (e.g. not as hard or harder in the next braking cycle). A position encoder 356 is used with the system 350.

In a still further embodiment of the present invention, a more complex processor may be used with the system 350. In this embodiment, rather than just a lookup table, the processor in control system 350 can calculate the level of deceleration and maybe make that relative to the contact point, so that you do not need to do an integration of the curve. Instead of using a ton of lookup tables, the system 350 can direct the lancet with a more elegant algorithm.

In still other embodiments, the control system 350 may be paired with an improved position sensor. If the processor desires a certain amount of data to make a predictive decision within the braking segment, the amount of position feedback to the processor may be increased. It may be that you may not have enough predictive ability because the control system is limited or it comes too late. The penetrating member 322 may already have gone too far or the controller is too slow to make the change. Accordingly, an improved position sensor may provide more position data. The data may arrive faster and it may be more precise as to the location of the penetrating member.

From an conceptual standpoint, it would be possible to further improve control system performance. As discussed, the position encoder would be improved. The clock speed of the processor would be faster to handle the additional flow of data because it comes faster. Finer control of the solenoid or other electronic drive mechanism may also be desired so that solenoid can move the penetrating member at a level of accuracy matching or coming close to that of the position encoder.

Optimally, the present invention provides for controlling the trajectory of the inbound lancet up to the point of maximum extension with an adaptive algorithm. With regards to the algorithm, in one embodiment, there is a decision point when the penetrating member 322 is still traveling in the inbound direction. With stored up data, based on this time and this position and a desired depth or profile, the control system 350 will make a decision whether to accelerate, brake, or do nothing. The decision point will ultimately determine what depth the penetrating member 322 reaches. It should be understood of course that there may be more than one decision point in a braking cycle. But if the deceleration is too high or other factors excessively slow the member 322, the control system 350 may choose to accelerate rather than brake. It could also brake harder, as the circumstances warrant.

It should also be understood that it may be possible to bring down the variance where the lancet ultimately ends up. For a certain depth, there is an optimal contact speed, given the uncertainly once the penetrating member 322 goes past initial contact with the tissue. It helps that the entire control system, in that it gives a neutral composition. There may be some braking or some acceleration, but there is not a huge amount of correction. There is a neutral position.

In one embodiment, if the braking algorithm is more complex in the sense that instead of just looking at position and time, it is looking at position and time for the last three cycles and dividing that into a smooth braking factor and taking that's distance (or corrected distance based on the contact point routine), then it is a simple multiplication of this factor and that position factor and that the system does not need a true update at the next look up table interval. It is a rolling average that gets the penetrating member to the intended depth at a higher degree of accuracy.

There is some variability with how the skin performs. Physiologically, as a nonlimiting example, a stick of about 2 mm in depth might increase the actual depth by +/−300 microns. Even though theoretically, the system can get really close to the desired depth with the control system, other mechanical or physiological reasons may create errors. Smarting braking increase the stability of the control system. It might have a more stable profile to deal with physiological uncertainties that are otherwise unaccounted for.

Various velocity profiles can influence cutting efficiency and more specifically, a final depth as the tissue reacts differently based on velocity of the penetrating member. As a nonlimiting example, if the penetrating members goes in fast and is braked hard, the tissue may still have momentum and the tissue/lancet interface may not be stable (i.e. not move together), and it might end up being that the composition of the tissue plays more of a factor. If you had a more stable control, the physiological variability of the tissue could be reduced or substantially taken out of the equation. In one embodiment of the present invention, the control tends to adjust the braking cycle so that the rate of deceleration is relatively constant and keeps the tissue or skin in a state where it does not have any unfair loads put on it. If the braking occurs too suddenly, the skin can bound away from the lancet and be keep moving.

Other improved embodiments of the control system, in addition to accounting for position and velocity, they may also account for trajectory. In one embodiment, the ideal lancing algorithm involves driving the lancet at a high rate of velocity to a predetermined depth, stopping at a given distance, and pulling out the lancet at a given rate. By achieving a contact speed, the device can meter the amount of force it presents to the skin at impact. This contact speed will be higher for a lancing cycle in which a higher penetration depth is intended. A velocity lookup table corresponding to the composite amount (The average velocity necessary to achieve a certain depth through iteration of many sticks) is set as one of the directions to the control sequence. The decision to redirect the lancet should come late in the lancing cycle and should be relative to displacement, rather than velocity. If the lancet passes within a certain distance of the intended displacement, the velocity can be checked by the control processor, and compared to a velocity lookup table.

As a nonlimiting example, 0.5 millimeters before the intended penetration distance, the speed is 30% of the contact speed. According to the velocity lookup table that is stored for this control algorithm and called at this displacement, the speed should be 30%. In this case, the control system does nothing to redirect the lancet. If the speed was 20% of the contact speed, this would indicate to the device that the lancet had decelerated too much, and a metered burst of energy corresponding to its deviation would be applied to the lancet from the drive motor to accelerate lancet to its intended displacement. If the speed was 40% of the contact speed, the lancet would be decelerated with a metered burst of energy. Because a linear position sensor has better position/time resolution at higher speeds and the ability of the motor to accelerate or decelerate is higher at low speeds, the decision to accelerate or brake should come at a displacement in which the velocity is consistently within the optimal working range of the position encoder and the motor. It should also occur late enough in the lancing cycle to be predictive. There may be more than one position-based decision point while penetrating, but the processing speed, force response of the electronic motor, and resolution of the position sensor are the physical determinants of whether this is feasible for the system and within what range of positions this control methodology is effective.

A more complex control algorithm would also utilize a least squares method in tandem with the velocity and position comparison. In this embodiment, this binomial equation would determine the rate of deceleration and invoke the braking or acceleration algorithm with the additional factor concerning the shape of the curve. It would distinguish between skin stiffness and skin position by effectively integrating the velocity vs. position curve during the deceleration phase of the lancing cycle. An algorithm factors these variables and accounts for them during in the control loop will provide a more desirable result, in terms of cutting efficiency and desired penetrating depth of a penetrating member into tissue.

Figure 10:
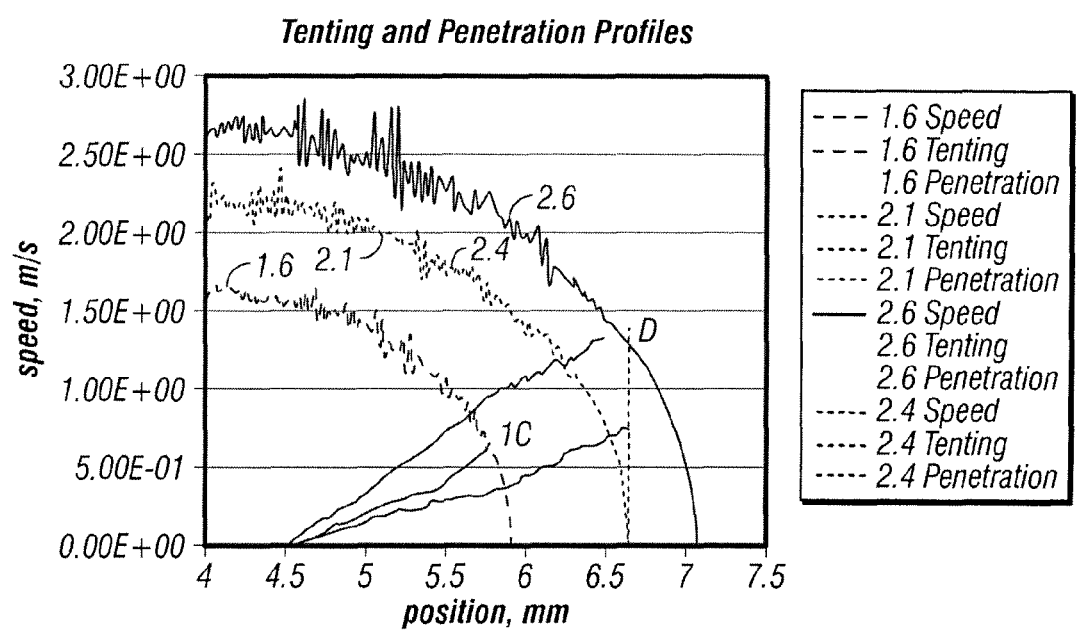
FIG. 10 shows a graph of tenting and penetration profiles.

In yet another embodiment of the present invention, disclosure is provided herein that relates to a mode of operation with an electronic lancet drive system where the inbound penetration of the lancet to the skin is determined by the amount of force applied by the motor. Referring now to FIG. 10, the graph shows lancing sticks or events into the same finger with different contact speeds. As seen in FIG. 10, there is a strong correlation between speed and penetration. No feedback is applied to obtain a certain position. As seen in FIG. 10, the repeatability of the depth appears to be high. There is also a relatively predictable way that the skin tents above a certain speed.

The current method concerning lancing involves driving the lancet at a high rate of velocity to a predetermined depth, stopping at a given distance, and pulling out the lancet at a given rate. In the present embodiment of the invention, the system involves an alternative control mode of operation where the intended depth is not held constant.

With electronic lancing and position feedback, the lancing device 20 can meter the amount of force it presents to the skin at impact. The contact speed will be higher for a lancing cycle in which a higher penetration depth is intended. In one embodiment, a velocity lookup table corresponding to the composite amount (the average velocity necessary to achieve a certain depth through iteration of many sticks) is set as one of the directions to the control sequence. There may be a desire not to exceed threshold of a certain position in which the lancet control system intervenes and stops the lancet from penetrating further.

The tenting and penetration appeared to be more consistent than when feedback is applied. When the rate of a blade already cutting through a material is suddenly changed, the cutting efficiency decreases and the blade binds. This may translate into increases in the amount and variance of deflection, or tenting, of the skin.

It should understood that this type of setup may be advantageous mode for some users. This is true if the physiological characteristics that determine successful sampling hold more consistently with force applied rather than depth achieved. Successful sampling is defined as a sufficient sample with a minimum of pain. The control system can introduce uncertainty for certain types of sticks by providing a position-based correction that does not need to occur. The device is not limited to this forced-based mode. Both force and position based control may be loaded on the same device.

Fixed Contact Point

Referring now to FIGS. 11A-11G, in one embodiment, the processor determines that the skin has been contacted when the end tip of the penetrating member has moved a predetermined distance with respect to its initial position. If the distance from the tip 961 of the penetrating member 183 to the target tissue 233 is known prior to initiation of penetrating member 183 movement, the initial position of the penetrating member 183 is fixed and known, and the movement and position of the penetrating member 183 can be accurately measured during a lancing cycle, then the position and time of penetrating member contact can be determined. This method requires an accurate measurement of the distance between the penetrating member tip 196 and the patient's skin 233 when the penetrating member 183 is in the zero time or initial position. This can be accomplished in a number of ways. One way is to control all of the mechanical parameters that influence the distance from the penetrating member tip 196 to the patient's tissue or a surface of the lancing device 180 that will contact the patient's skin 233. This could include the start position of the magnetic member 202, magnetic path tolerance, magnetic member 202 dimensions, driver coil pack 188 location within the lancing device 180 as a whole, length of the elongate coupling shaft 184, placement of the magnetic member 202 on the elongate coupling shaft 184, length of the penetrating member 183 etc. If all these parameters, as well as others can be suitably controlled in manufacturing with a tolerance stack-up that is acceptable, then the distance from the penetrating member tip 196 to the target tissue 233 can be determined at the time of manufacture of the lancing device 180. The distance could then be programmed into the memory of the processor 193. If an adjustable feature is added to the lancing device 180, such as an adjustable length elongate coupling shaft 184, this can accommodate variations in all of the parameters noted above, except length of the penetrating member 183. An electronic alternative to this mechanical approach would be to calibrate a stored memory contact point into the memory of the processor 193 during manufacture based on the mechanical parameters described above.

In another embodiment, moving the penetrating member tip 196 to the target tissue 233 very slowly and gently touching the skin 233 prior to actuation can accomplish the distance from the penetrating member tip 196 to the tissue 233. The position sensor can accurately measure the distance from the initialization point to the point of contact, where the resistance to advancement of the penetrating member 183 stops the penetrating member movement. The penetrating member 183 is then retracted to the initialization point having measured the distance to the target tissue 233 without creating any discomfort to the user.

Using an Acoustic Signal to Determine Contact Point

Figure 31:
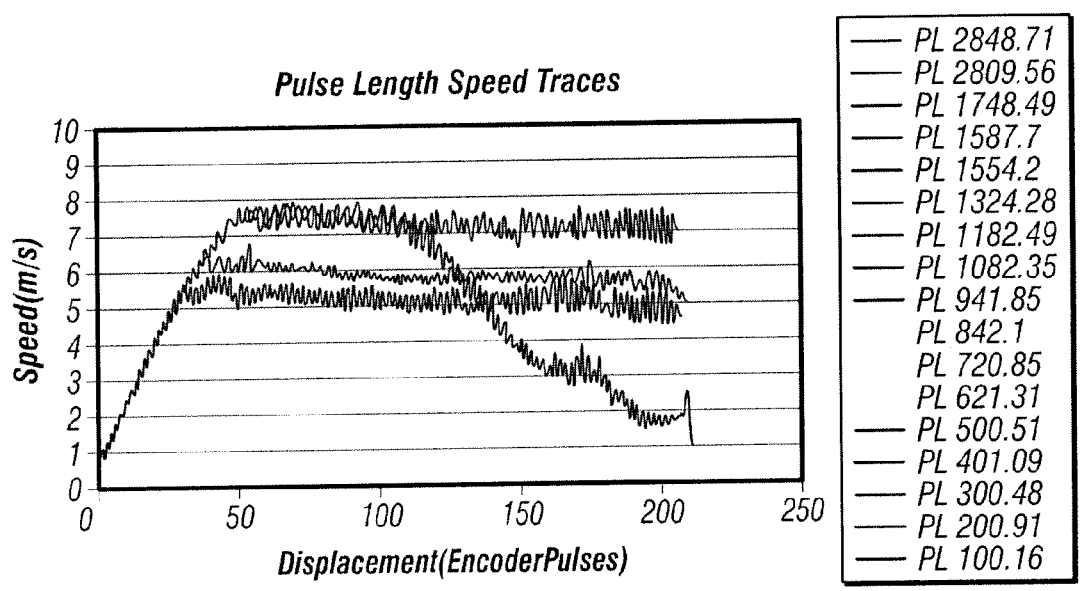
Figure 32:
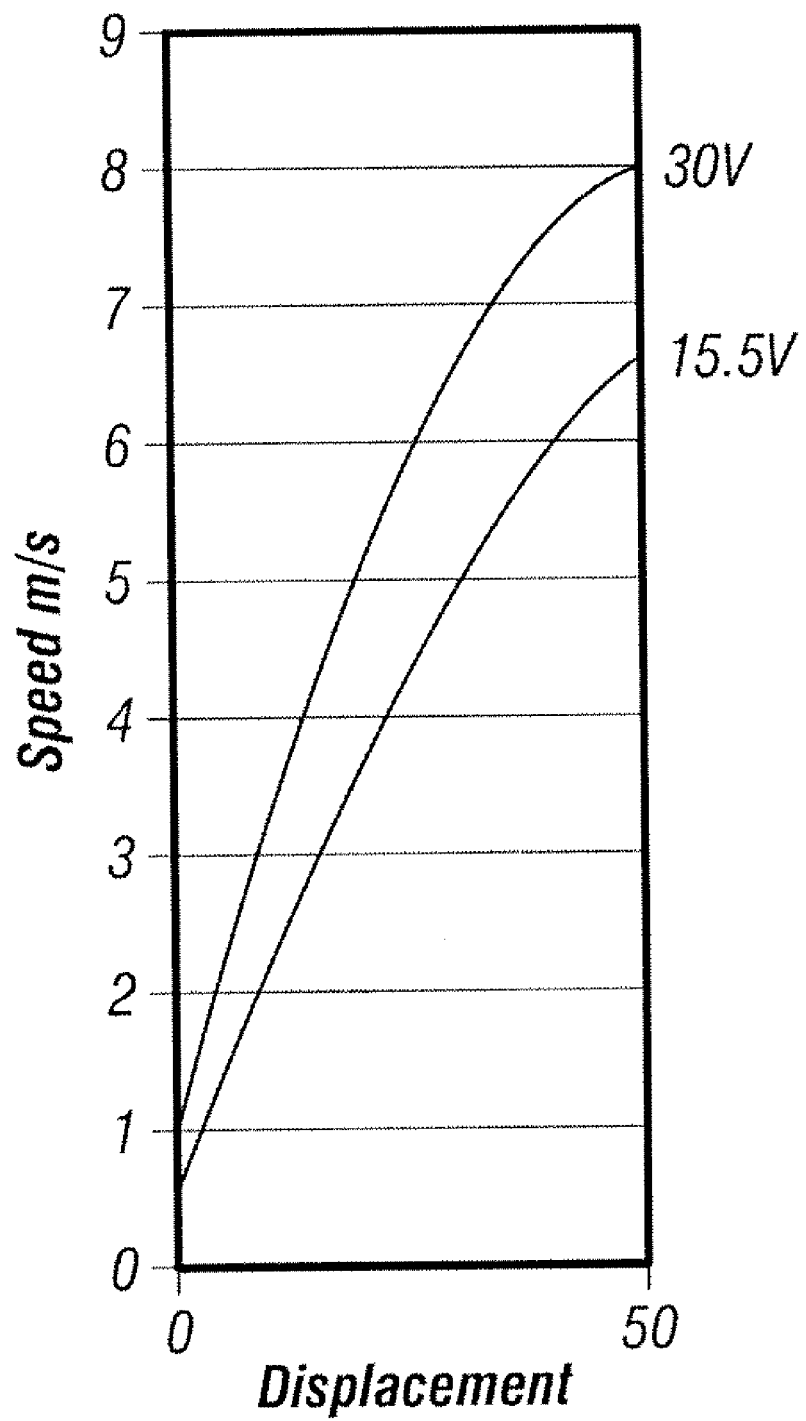

In yet another embodiment, the processor 193 determines skin 233 contact by the penetrating member 183 by detection of an acoustic signal produced by the tip 196 of the penetrating member 183 as it strikes the patient's skin 233. Detection of the acoustic signal can be measured by an acoustic detector 236 placed in contact with the patient's skin 233 adjacent a penetrating member penetration site 237, as shown in FIG. 31. Suitable acoustic detectors 236 include piezo electric transducers, microphones and the like. The acoustic detector 236 transmits an electrical signal generated by the acoustic signal to the processor 193 via electrical conductors 238.

Using Continuity in an Electric Circuit to Measure Contact Point

In another embodiment, contact of the penetrating member 183 with the patient's skin 233 can be determined by measurement of electrical continuity in a circuit that includes the penetrating member 183, the patient's finger 234 and an electrical contact pad 240 that is disposed on the patient's skin 233 adjacent the contact site 237 of the penetrating member 183. In this embodiment, as soon as the penetrating member 183 contacts the patient's skin 233, the circuit 239 is completed and current flows through the circuit 239. Completion of the circuit 239 can then be detected by the processor 193 to confirm skin 233 contact by the penetrating member 183. If the penetrating member 183 has not contacted the target skin 233, then the process proceeds to a timeout operation. In the timeout operation, the processor 193 waits a predetermined time period. If the timeout period has not yet elapsed (a "No" outcome from the decision box 267), then the processor continues to monitor whether the penetrating member has contacted the target skin 233. The processor 193 preferably continues to monitor the position and speed of the penetrating member 183, as well as the electrical current to the appropriate coil 214-217 to maintain the desired penetrating member 183 movement; If the timeout period elapses without the penetrating member 183 contacting the skin (a "Yes" output from the decision box 267), then it is deemed that the penetrating member 183 will not contact the skin and the process proceeds to a withdraw phase, where the penetrating member is withdrawn away from the skin 233, as discussed more fully below. The penetrating member 183 may not have contacted the target skin 233 for a variety of reasons, such as if the patient removed the skin 233 from the lancing device or if something obstructed the penetrating member 183 prior to it contacting the skin.

Reduction in Penetrating Member Velocity to Determine Contact Point

In another embodiment, the processor 193 may use software to determine whether the penetrating member 183 has made contact with the patient's skin 233 by measuring for a sudden reduction in velocity of the penetrating member 183 due to friction or resistance imposed on the penetrating member 183 by the patient's skin 233. The optical encoder 191 measures displacement of the penetrating member 183. The position output data provides input to the interrupt input of the processor 193. The processor 193 also has a timer capable of measuring the time between interrupts. The distance between interrupts is known for the optical encoder 191, so the velocity of the penetrating member 183 can be calculated by dividing the distance between interrupts by the time between the interrupts. This method requires that velocity losses to the penetrating member 183 and elongate coupler 184 assembly due to friction are known to an acceptable level so that these velocity losses and resulting deceleration can be accounted for when establishing a deceleration threshold above which contact between penetrating member tip 196 and target tissue 233 will be presumed.

This same concept can be implemented in many ways. For example, rather than monitoring the velocity of the penetrating member 183, if the processor 193 is controlling the penetrating member driver in order to maintain a fixed velocity, the power to the driver 188 could be monitored. If an amount of power above a predetermined threshold is required in order to maintain a constant velocity, then contact between the tip of the penetrating member 196 and the skin 233 could be presumed. All of the above figures are in reference to figures found in U.S. patent application Ser. No. 10/127,395.

Using a Slow Moving Penetrating Member to Determine Contact Point

In a still further embodiment, a new contact point algorithm is run before the actual lance event. As a nonlimiting example, such an algorithm may be run immediately prior to lancing.

Whether the penetrating member is striking a finger or other material/object can be determined. Information about the skin properties of the finger can be determined. With a reasonable sized aperture, the finger contact point can vary by more than the depth of penetration. Unless the contact point can be accurately determined, correct depth may be difficult to control. This method cancels out mechanical variations that occur in the manufacturing process of the actuator, coupling to the penetrating member, and length of the penetrating member. In addition, we can determine if there is anything there at all (strike into air). The finger in the above description can be any part of the body to be lanced.

Description of the algorithm: In one embodiment, the penetrating member is accelerated to a slow speed, in the present embodiment of the actuator, it is about 0.6 to 0.8 meters/second. It should be understood that this is a nonlimiting example. The speed may be tuned to the mass of the lancing assembly. The more the mass of the assembly, the slower the speed should be. Since the energy stored in the assembly is determined by $\frac{1}{2} MV^2$, the desire is to store a sufficiently small amount of energy such that the penetrating member does not penetrate or does not significantly penetrate the stratum corneum of the skin.

Figure 12A:
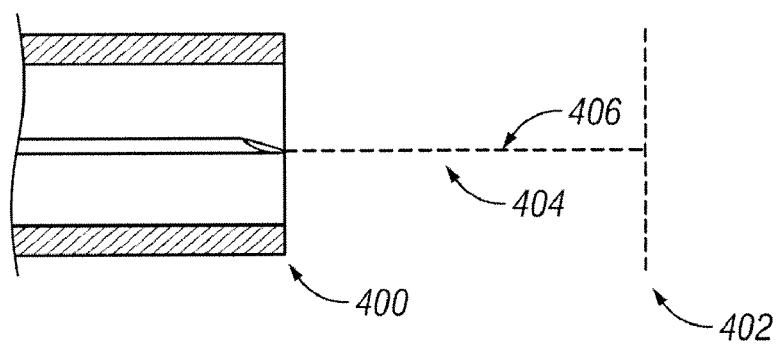
FIGS. 12A-12C show various embodiments of a tissue penetrating device.
Figure 12B:
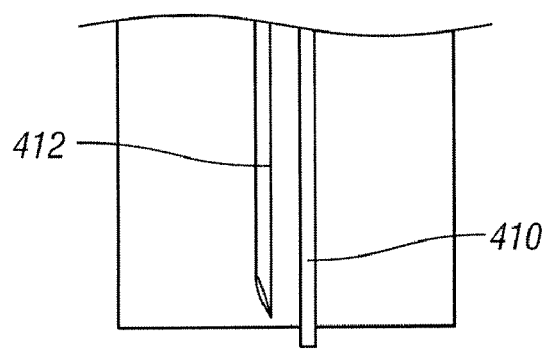
Figure 12C:
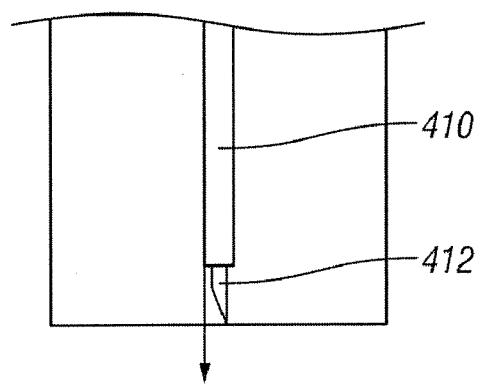

Referring now to FIG. 12A-12C, the speed of the penetrating member is maintained at the desired velocity until the Start Contact Search Point 400 is reached. In the present embodiment, this is simply first point before the contact can occur. The coil power is turned off when the Start Contact Search Point is reached, and the penetrating member assembly coasts. In one embodiment, this Start Contact Search Point may be where the front end of the device is located.

Unimpeded, the penetrating member assembly in this present embodiment of the invention will coast until the Stop Contact Search Point is reached 402. In the present embodiment, this is simply the maximum point at which a finger can be placed for a valid strike to be achieved. Since the penetrating member assembly has a maximum depth limited by the physical stop, unless there is enough depth available (maximum depth-contact point has to be >desired depth) there is no reason to continue the stick. This is also the way it is determined that the penetrating member would strike into air.

While coasting, a base speed of the penetrating member at the beginning of the Start Contact Search Point is established and the speed of the penetrating member assembly is monitored. Position feedback and monitoring is discussed in commonly assigned copending U.S. Pat. No. 7,025,774, fully incorporated herein by reference. When a slowdown of more than a preset threshold (in one embodiment, we have found that about 12.5% seems to work fine), the distance at which this occurs is recorded. In one embodiment, this distance may be recorded in the processor or in memory coupled to a processor. This is called the tentative contact point 404. Using a quadrature phase sensor in one embodiment of the present invention or other sensor, we can measure direction. The coasting continues until a reversal of direction or a timeout occurs with no reversal. In one embodiment, if no reversal occurs, we may assume that either binding in the mechanical assembly occurred or the penetrating member struck something that did not rebound. This is called a stall.

The penetrating member and driver are configured so that feedback control is based on penetrating member displacement, velocity, or acceleration. The feedback control information relating to the actual penetrating path is returned to a processor that regulates the energy to the penetrating member driver, thereby precisely controlling the penetrating member throughout its advancement and retraction If a reversal of direction occurs, we store this value or distance too. The difference between the reversal point 406 and tentative contact point 404 is calculated. The positions shown in FIG. 12A purely illustrative and are nonlimiting. If the difference is lower than a preset threshold, we know this is not a typical finger. If the difference is above the threshold we declare it is a finger and the difference between the two is a measure of the stretching or tenting as discussed in copending U.S. patent application Ser. Nos. 10/127,395 & 60/476, 584. In one embodiment, the above rules result in many output codes from the contact point algorithm. They are summarized below.

1. Valid contact point detected (outputs contact point measurement and reversal point)
2. Stop Contact Search Point exceeded. No contact point detected because there was no slowdown within the Contact Search range (Start Contact Search Point to Stop Contact Search Point).
3. Start Contact Search Point error. The contact point (slowdown) was detected too close to the Start Contact Search Point such that the slowdown might have already started during the establishment of the base speed.
4. Stall—A stall is an error that results from a slowdown detected, but no reversal (described above).
5. Contact Hard Surface—this error results from a the difference between the reversal and tentative contact point being is lower than a preset threshold. This indicates the object hit did not deform, so we know this is not a typical finger.

The difference between the threshold value and the actual measured difference between the reversal point 406 and the tentative contact point 404 may be used to adjust the desired penetration depth. For example, if the distance between points 406 and 404 is greater than a threshold value, then this tissue exhibits more tenting than the standard tissue model. The desired penetration depth may then be increased to account for the extra tenting. On the other hand, if it turns out that the distance between points 406 and 404 is less than the threshold, then this tissue exhibits less tenting. The desired penetration depth may then be reduced, by a proportional amount in one embodiment, since the tissue has less tenting to account for.

After the skin or other tissue relaxes, the difference between the reversal position 406 and the initial position 404 may be measured so that the amount of tenting T for this stick or lancing event is known. Now the actual penetration or depth in the skin or tissue may be calculated and a new target depth may be calculated by adding the variance of the actual depth from that of the threshold to the target depth to yield a new target depth that now compensates for the amount of tenting. In one embodiment, the engine or penetrating member driver that actuates the penetrating member is reengaged to achieve the new target depth which includes the distance to compensate for tenting. This process is relatively fast such as but not limited to under about 50 ms, so that it appears and feels like one operation to the user or patient. In another embodiment, at least one separate probe may be used to provide skin qualities. As a nonlimiting example as seen in FIG. 12B, a separate probe 410 with mass and dimension substantially similar to that of the penetrating member 412 may be used to determine tissue quality. The probe 410 may be used to determine features and then the penetrating member 412 fired to create the tissue wound. In another embodiment, a coaxially mounted movable probe (slidable over the penetrating member) may be advanced to determine tissue quality.

In another aspect of the present invention, penetration depth may be controlled via speed and deceleration power modulation. Penetration depth of an electronically actuated penetrating member device is controlled by modulating the speed and the deceleration power. In other embodiments, the methodology was to accelerate the penetrating member to a constant speed and control depth by adjusting the point along the penetrating member trajectory where braking began. This current embodiment of the method takes advantage of the ability to modulate the amount of braking power applied as well as the ability to modulate penetrating member speed to control penetration depth. Penetrating member speed has also been studied and optimized for each depth setting. Varying the braking power provides a still further variable which may be adjusted to provide improved penetration depth control. It may also allow for more variety in velocity profiles used with actuating the penetrating member.

Figure 13:
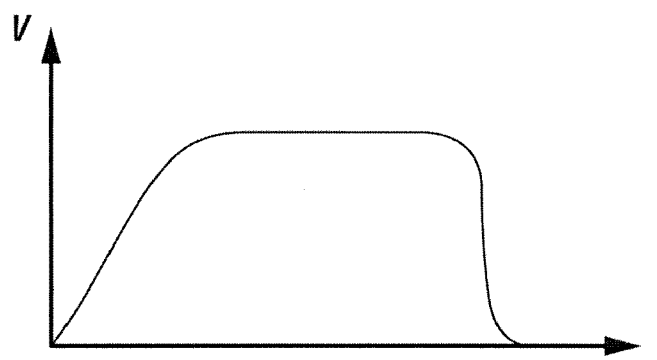
FIGS. 13-15 show graphs of penetrating member velocity over time.
Figure 14:
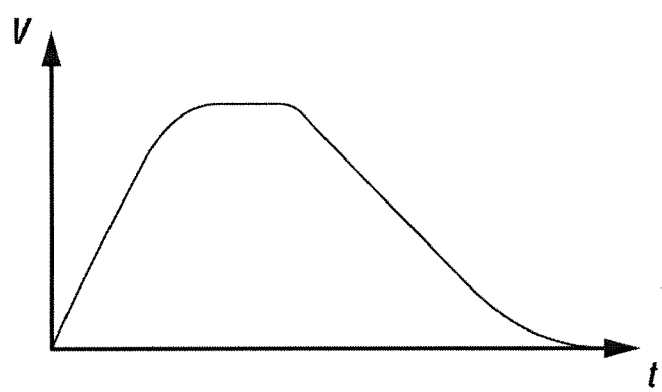
Figure 15:
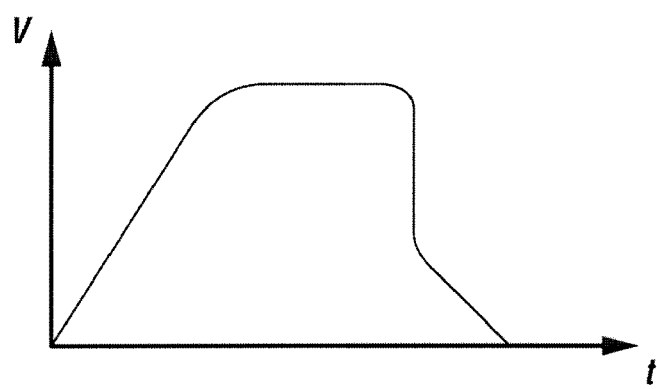

Referring to FIG. 13, as a nonlimiting example, being able to increase the braking force allows a user to increase penetration velocity and maintain that velocity for a longer period of time in the tissue and then bring the penetrating member to a stop a the desired depth. In other embodiments as seen in FIG. 14, it may be desirable to brake slowly over a greater distance and thus provide a soft stop. In a yet further embodiment as seen in FIG. 15, the braking force may be modulated to be any combination of the above such as but not limited to an initial hard braking followed by a period of soft braking to bring the penetrating member to a controlled stop. It should be understood that any combination of the above hard and soft braking may be used. Variation in braking force also provides an additional variable during feedback control such that position of the penetrating member as it nears a desired depth may be braked with more force so that the penetrating member stops at the desired depth. It should be understood that the above may be used with an electronic lancing device as disclosed in U.S. patent application Ser. No. 10/127,395. The braking force control may be adapted for use with a processor. The braking force control may be used with a multiple penetrating member device such as that disclosed in U.S. patent application Ser. No. 10/423,851.

Figure 16:
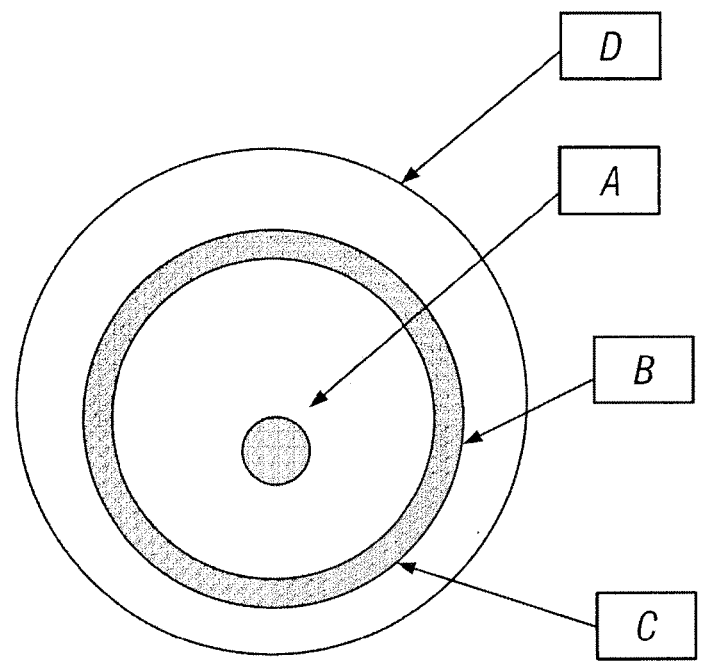
FIG. 16 shows a schematic representation of the reperfusion of skin after impact.

Referring now to FIG. 16, a schematic representation of the reperfusion of skin after impact with a tent and hold motion profile is shown. This figure is not to scale, and does not describe depth. This is a top down schematic view onto the skin or tissue. Penetrating member strikes perpendicularly to the skin in area A. Blood is initially forced out to an area D. Blood will quickly return from D to C as the skin settles after the shock of impact. Tent and hold allows blood reperfusion from C to B and is due to the delayed deformation of the skin tissue immediately around A, unloading the peripheral skin tissue vasculature. The vasculature also functions as a pressure system, forcing blood towards the penetrating member after a delay that is related to the force of impact. This pressuring is one factor in increasing spontaneous blood generation.

Figure 17:
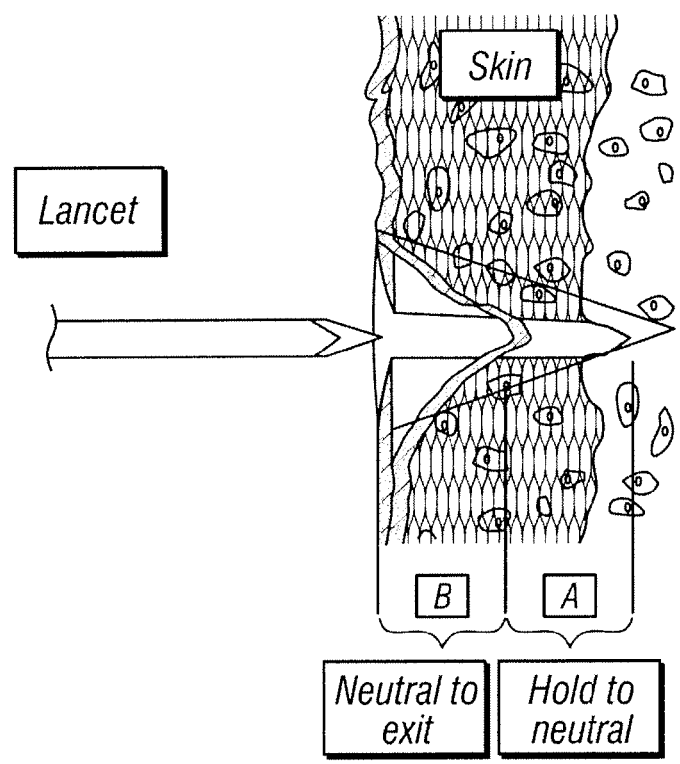
FIG. 17 shows a tissue penetration device piercing skin.

Referring now to FIG. 17, two components of retraction profile are shown: As a nonlimiting example, reference letter A shows a "hold-to-neutral" position or range—when skin-penetrating member interface migrates together, and the skin settles naturally after the impact force tents the tissue. Perfusion acts as three-dimensional function of the pressure. Pressure distribution and perfusion is cone-shaped, as illustrated by the blue triangle below. Reference letter B shows neutral to exit position or range where the actuator retracts the penetrating member from the skin.

Figure 18:
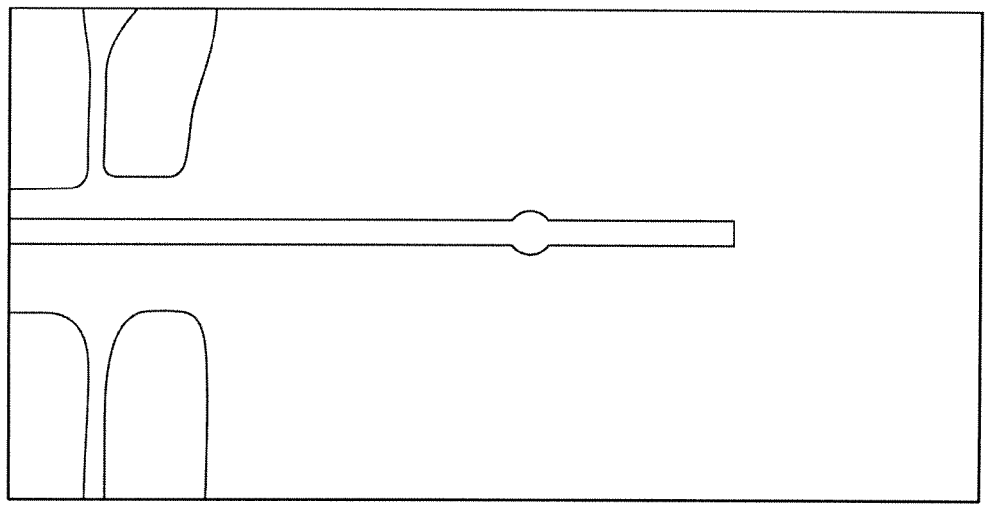
FIGS. 18-21 are images of penetrating members and their interaction with tissue.

Referring now to FIG. 18, a high resolution image of the penetrating member and skin interface is shown. Specifically, the figure shows a "hold-to-neutral" phase—when skin-penetrating member interface migrate together.

Figure 19:
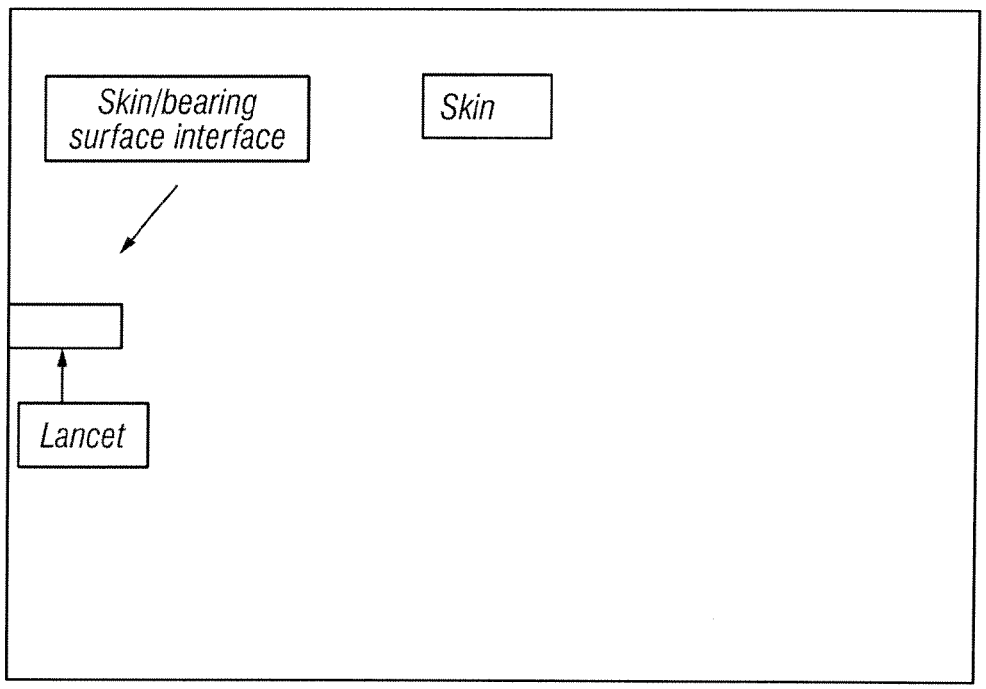

Referring now to FIG. 19, a high-resolution optical image of skin relaxation "Natural Settling" with skin relaxing unimpeded by penetrating member.

In some embodiment, a tent and hold profile 1 at 2.6 ms may be used. A tent and hold profile 1 at 6.6 ms is used in some embodiments. Primary visible skin buckling has broadened, and proximal edge of the wound channel has slid up the penetrating member shaft. A tent and Hold profile 2 at 3.9 ms is shown. Other experiment parameters are held constant. A tent and hold profile 2 at 6.6 ms is shown. The buckling is not as evident, but the sliding is more obvious.

Figure 20:
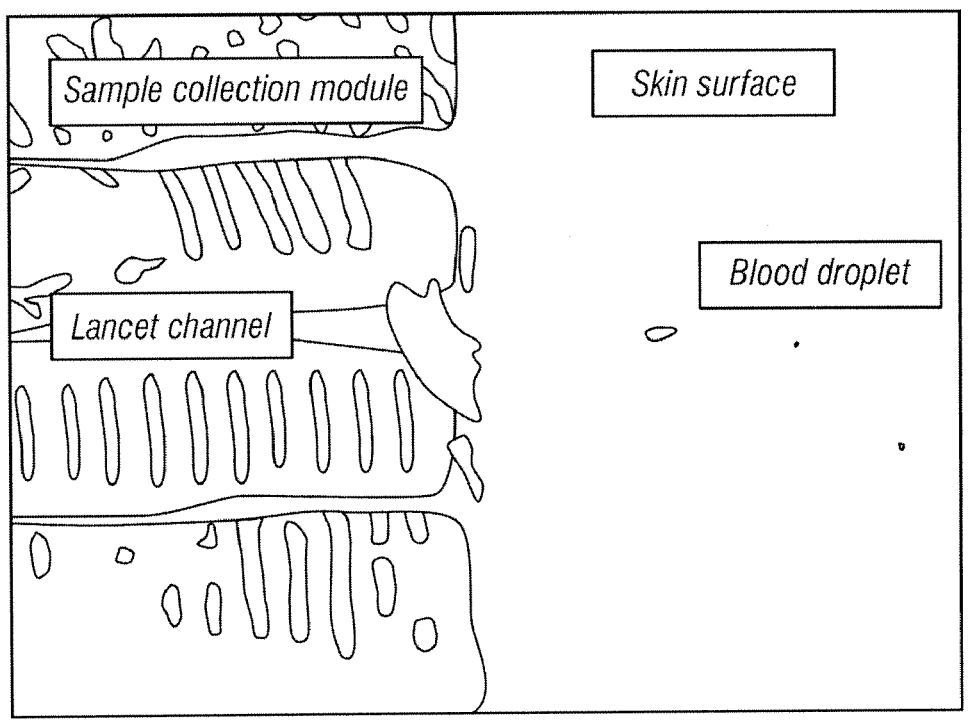

Referring now to FIG. 20, a Natural relaxation 4 seconds after the strike is shown. After a good initial spontaneous, flow, the flow stalls.

Figure 21:
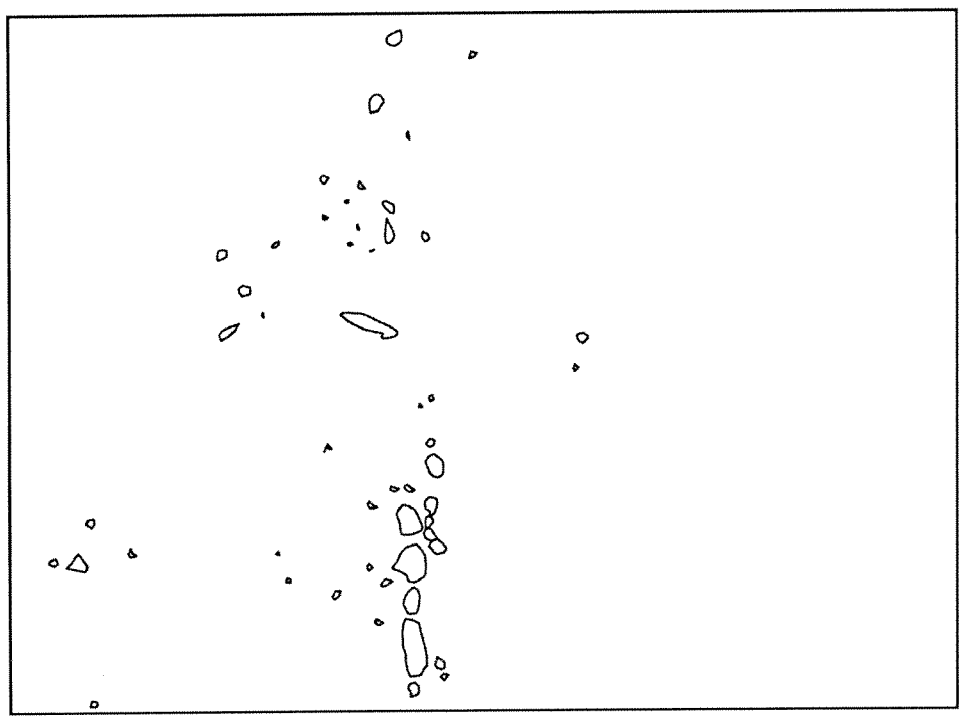

Referring now to FIG. 21, a Tent and Hold profile 2 at 4 s is shown. The motion profile results in an extended period of high spontaneous flow. Module fills despite large offset of the skin relative to the collection channel.

Spontaneous blood yield can be achieved by a lancing motion profile that holds the penetrating member at maximum extension for a prolonged period of time. The viscoelastic of the skin may allow for a momentary tissue deflection that would rebound immediately after the penetrating member was retracted. A tent and hold lancing profile counteracts this natural property of the skin. In one embodiment, the penetrating member driver can maintain an extended position for about 2-8 ms, and then make a controlled retraction out of the finger. The skin will slide up the penetrating member shaft as the collagen matrix in the reticular layer inelastically deforms. In this nonlimiting example, the penetrating member continues to cut, but only as a result of the relaxation of the surrounding tissue. This deformation during the hold happens radially as well as axially to the penetrating member shaft. With tissue compressed more evenly around the lanced area, the resulting wound maintains it shape longer before it collapses into a thin line that would resist blood spontaneously rising to the surface. The wound shape may exhibit increased blood sufficiency by counteracting tissue rebound characteristics using the tent and hold profile.

In one embodiment, to achieve a "tent-and-hold" event, the penetrating member penetrates to the intended depth and then may maintain the position in the skin to prevent or retard the relaxation of the tissue, which would naturally return at approximately 1 m/s. In one nonlimiting example, holding the penetrating member in the skin between about 2 to 100 milliseconds appears be ideal to achieve spontaneous blood yield. Deeper lances will require more "hold" time. In one embodiment, hold may be achieved by removing the drive force from the penetrating member while letting the skin or tissue relax and reposition the penetrating member. In other embodiments, hold may involve placing the penetrating member at a fixed depth and maintaining that depth for the desired period. Although not limited by the following, motion profiles for which the hold time is longer than about 1 second may introduce a deleterious physical reaction from the patient or unnecessary pain. It may also use more power from the motor to maintain the position of the penetrating member for an extended period of time.

Some advantages of a "tent-and-hold" motion profile or trajectory waveform include:

1. Integrity of the wound channel by decreasing the effect of distension in the wound channel. The viscoelasticity of the skin may allow for a momentary tissue deflection that would rebound immediately after the penetrating member was retracted. A tent and hold lancing profile may counteract this natural property of the skin. This behavior can be directly observed when the penetrating member is held for greater than 200 microseconds. The skin will slide up the penetrating member shaft as the collagen matrix in the stratum reticulare layer inelastically deforms. The penetrating member continues to cut, but only as a result of the relaxation of the surrounding tissue. This deformation during the hold happens radially as well as axially to the penetrating member shaft. With tissue compressed more evenly around the lanced area, the resulting wound maintains it shape longer before it collapses into a thin line, which may resist blood spontaneously rising to the surface.

2. A limited amount of pinching and subsequent binding of the venuoles (at deeper lancing depths) by surrounding tissue at the target depth. In one nonlimiting example, a strike with the best yield would involve the larger venuoles at higher depths filling the channel with blood. As the blood moves with the retracting penetrating member up the channel, the inside of the channel is coated with blood, allowing the blood in smaller venuoles with higher pressures to overcome to use the advantage of the bloods natural surface tension to lower the pressure threshold that would prevent blood spontaneously coming to the surface. The momentum that a well-executed tent and hold with an appropriate retraction rate would build in the lancing channel not only decreases the number of sticks or lancing events with no spontaneous blood, but decrease the number of spontaneous sticks that are spontaneous but would require milking of the finger to gather a sufficient sample. This increase in the yield/depth ratio would thereby reduce pain/yield, as an optimal retraction speed profile would reduce the depth sufficient to gather a sufficient sample.

3. The force of the impact evacuates the blood from the area around the penetrating member channel. This lack of movement after the impact allows for reperfusion into the area of the strike before any significant movement occurs. If the pressure is too high in the tented tissue area, the blood may not return until the retraction is performed. However, the coherence and focus of the tissue reperfusion is greater with the device-controlled relaxation of the penetrating member.

Once the penetrating member holds a certain period of time, there are two components of the retraction profile that influences blood spontaneously reaching the surface of the skin. The held-to-neutral subcomponent, (which may be at a speed), which facilitates a focused and optimal reperfusion of the lanced area; and the neutral-to-exit subcomponent, which allows the penetrating member to perform at least one of the following:

Travel without binding or damaging the wound channel.

Prevent the channel from closing up abruptly, enabling blood to displace the penetrating member as it performs a controlled exit.

The power requirement to hold a penetrating member may vary. Variations may be due in part to type of drive device such as but not limited to solenoid or voice coil and the like. In another embodiment, the penetrating member may apply a force only great enough to slow the relaxation of the skin, but not to hold the relaxation of the skin. The relationship of the power to tent-and-hold, or damp-and-hold may be related to: the skin characteristics e.g. hydration, possibly stratum corneum thickness. The power used to retract the penetrating member from a given depth or given skin may be used to relate characteristics of the skin. The wound stabilization characteristics required to get the blood out, reorientation of collagen fibers to keep the channel patent, may depend on the velocity profile used.

Figure 22A:
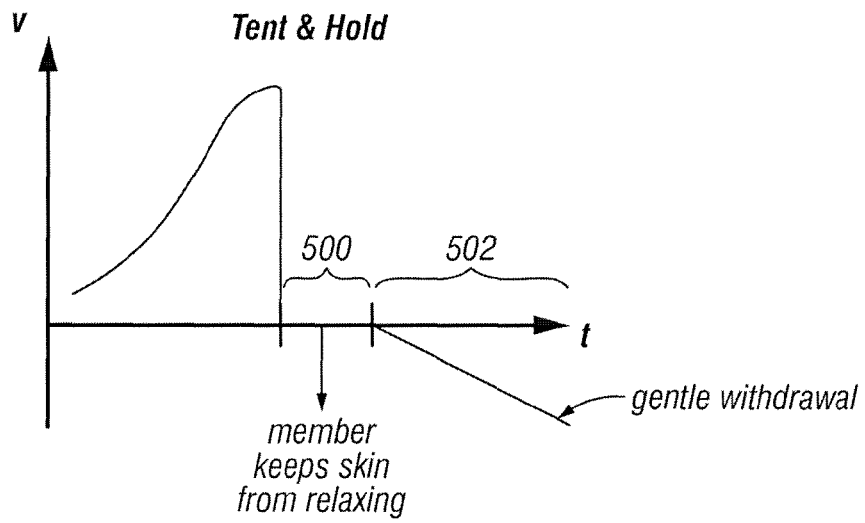
FIGS. 22-23 show various control methods as illustrated in graphs of velocity overtime.
Figure 22B:
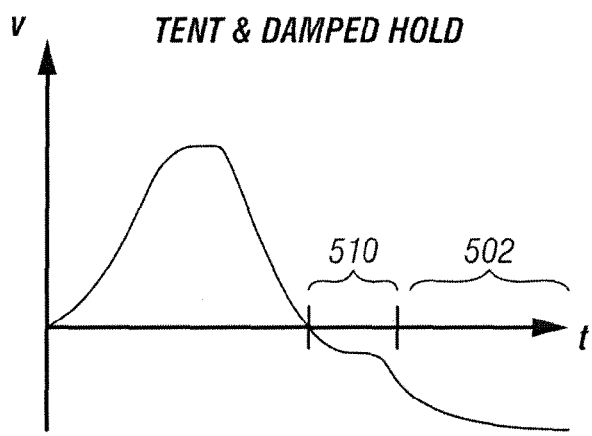
Figure 22C:
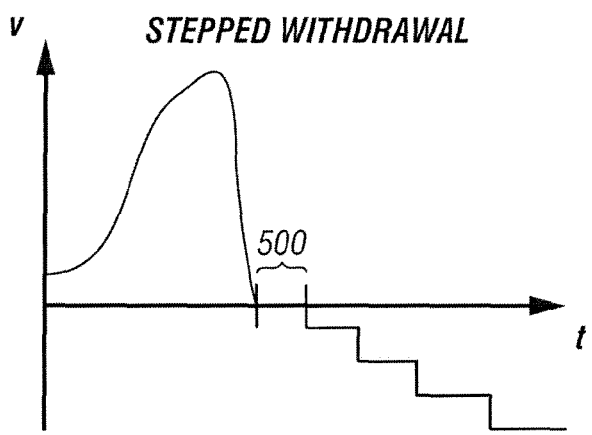

Some of the various embodiments of motion profiles, velocity profiles, or velocity waveforms are shown in FIGS. 22A-22C. As a nonlimiting example, FIG. 22A shows a velocity versus time chart for a tent and hold velocity profile. After the hold period 500 where sufficient force is applied to hold the penetrating member at the current depth in the tissue, in this embodiment, there is a withdrawal phase 502 where the penetrating member is backed out of the tissue at a velocity slower that the average entry velocity. The portion 502 is for velocity on the withdrawal of the penetrating member from the tissue.

Referring now to FIG. 22B, another embodiment of the velocity profile is shown. In this embodiment, the profile is characterized as a "tent and damped hold" where sufficient force is applied to the penetrating member to allow it to move retrograde, but at a velocity slower than that which it would move if no force were applied and the skin or tissue naturally relaxes. The damped hold over region 502 may occur at a controlled rate. After this damped hold, the penetrating member may be backed out of the skin at reduced velocity as indicated by 502.

Referring now to FIG. 22C, yet another embodiment of a velocity waveform is shown. FIG. 22C shows an embodiment where there is a hold period 500, after which the penetrating member is withdrawn using a stepped withdrawal. In one nonlimiting example, the steps occur so that the average withdrawal speed is less that the average penetrating member inbound speed. The stepped configuration may provide more time for collagen in the skin to form around the shaft of the penetrating member during each withdrawal motion so that the wound shape and patentness of the wound channel may be maintained more easily (temporarily) by the collagen. This allows body fluid to more easily follow the wound tract created by the penetrating member so that the fluid can reach the surface. The steps may be at various spacings such as but not limited to about 50 ms per step, 75 ms per step, 100 ms per step, or other step times as desired.

Figure 22D:
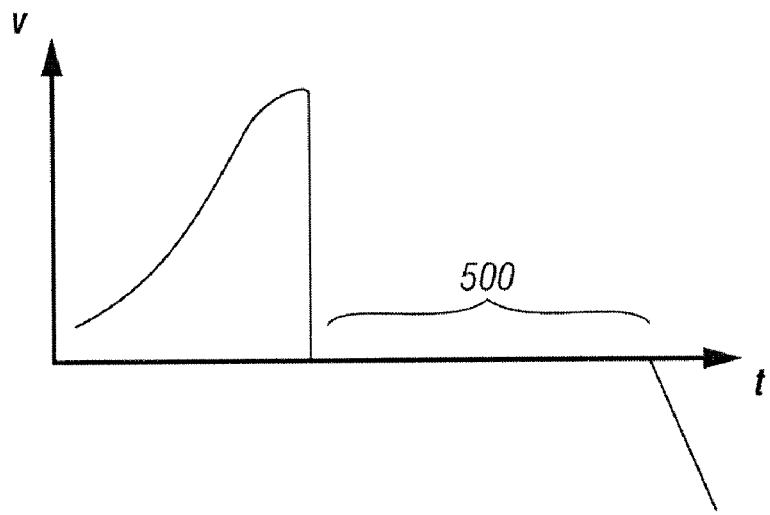

Referring now to FIG. 22D, a still further embodiment of the waveform is shown. FIG. 22D shows a profile where the hold period 500 is of an extended time. This may allow the collagen to form about the penetrating member to help maintain the patentency of the wound channel. After a selectable amount of time, the penetrating member may be backed out of the skin as indicated by 512. The embodiment shown in FIG. 22D has the pull out occurring at an average velocity greater than that of the average inbound penetrating member velocity. In one embodiment, the overall time that the penetrating member is in the tissue may be about 500 ms. In other embodiments, the overall time in tissue or skin may be about 450 ms, 400 ms, 350 ms, 300 ms, 250 ms, 200 ms, 150 ms, 100 ms, 75 ms, 50 ms, 25 ms, 20 ms, or 15 ms. These number may be applicable to any of the velocity profiled disclosed herein or in the profiles shown in U.S. patent application Ser. No. 10/127,395.

Figure 23:
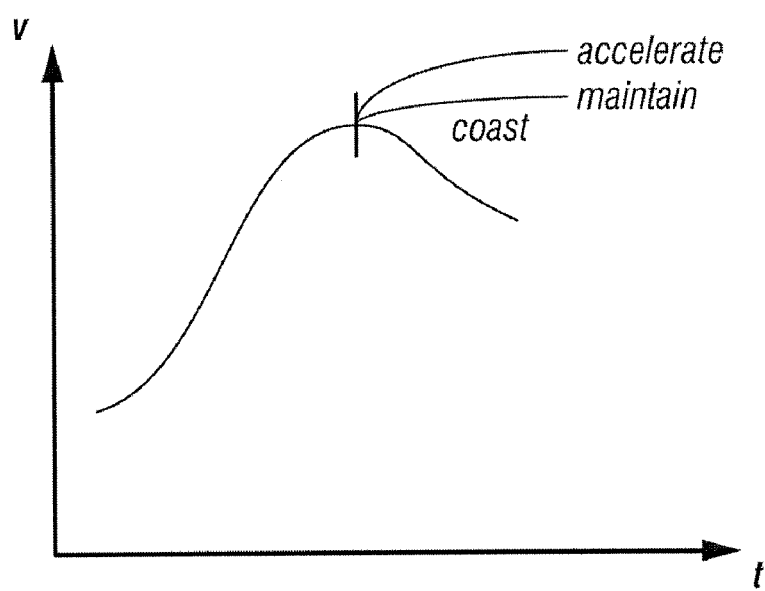

FIG. 23 shows an embodiment where it should be understood the penetrating member velocity may be increased or decreased or maintained based on various decision points along the velocity trajectory. Further disclosure can be found in commonly assigned, copending U.S. patent application Ser. No. 10/420,535 filed Apr. 21, 2003, and fully incorporated herein by reference.

Figure 24:
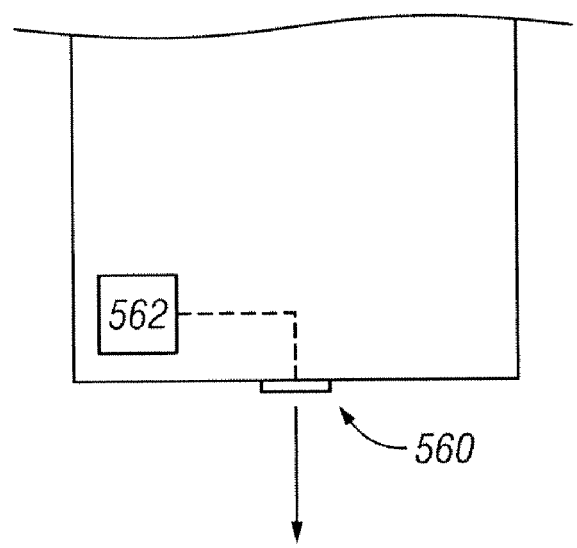
FIGS. 24-25 show schematics of embodiments of a penetrating member device with a controller to account for pressure.
Figure 25:
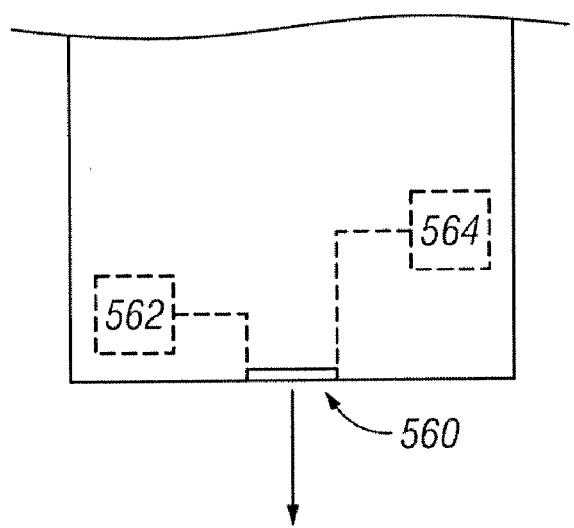

Referring now to FIG. 24, a still further embodiment, a controller may also account for pressure from applying a front end of the body fluid sampling device to the skin or tissue. The effect of front end pressure and stretching are discussed in U.S. Pat. No. 6,306,152 fully incorporated herein by reference. Stretching from the front end may influence the amount of tenting of the underlying tissue. In one embodiment, the front end 560 may have an aperture sized of about 4.5 mm. The aperture may be varied in size from annular ring, square, triangular, polygonal, hexagonal, or other shaped. In one embodiment, the front end 560 may be movable into the housing as seen in FIG. 25. The front end 560, when depressed, may configured to only provide a selected amount of force, thus making the tenting quality of the skin more controllable. In other embodiments, a pressure transducer 562 may be coupled to the front end. The measurements from the pressure transducer 562 may be used by the controller 564 to adjust the tenting adjustment. Various adjustment amounts may be stored in a lookup table in the device. The pressure transducer 562 may also be used during calibration or measurement of the tenting T so that it will be recorded and adjusted for if later lancings with the device do not occur at the same pressure. The tenting amount T may be adjusted based on the pressure used during the original measurement and the amount being applied during the current lancing.

Figure 26:
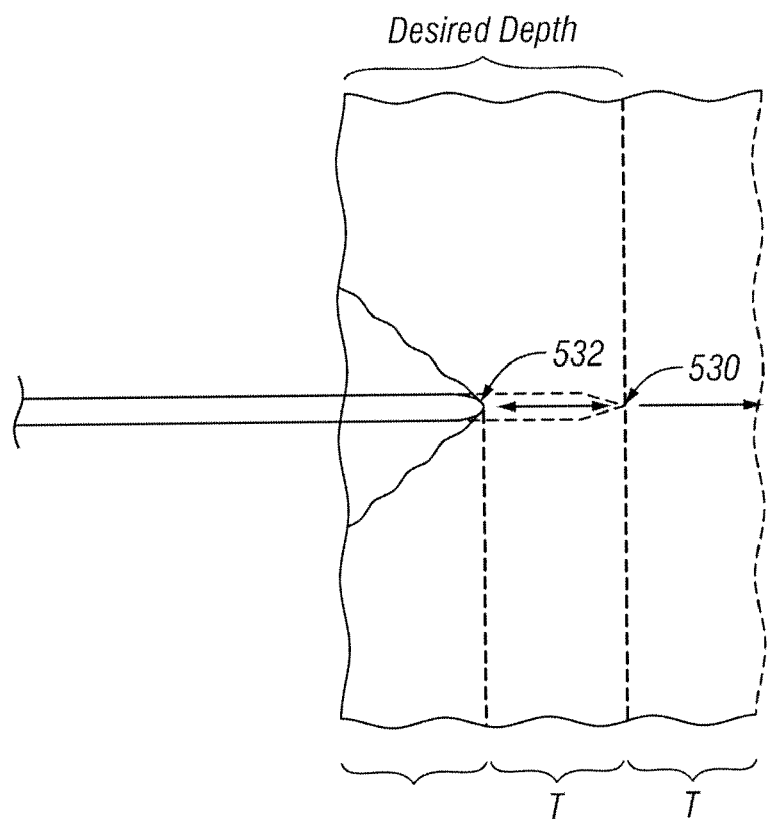
FIG. 26 shows a penetrating member in tissue.

In a still further embodiment of the present invention, a method for accurate control of penetrating member depth will be discussed. Referring now to FIG. 26, the invention claims that the true depths may be consistently obtained for a desired depth by lancing to the desired depth neglecting tenting. In one embodiment, after this first depth 530 is achieved, the drive is turned off and skin or other tissue is allowed to relax until it has a neutral or "un-tented" as shown in FIG. 17 and per previously described in commonly assigned, copending U.S. patent application Ser. No. 10/127,395, filed Apr. 19, 2002, and incorporated herein by reference. In FIG. 14, this position is shown at position 532.

After the skin or other tissue relaxes, the difference between the deepest penetration to position 530 and the relaxed position 532 may be measured so that the amount of tenting T for this stick or lancing event is known. Now the actual penetration or depth in the skin or tissue may be calculated and a new target depth may be calculated by adding the tenting distance T to the target depth to yield a new target depth that now compensates for the amount of tenting (assuming the position 530 represented the desired depth of penetration into tissue. In one embodiment, the engine or penetrating member driver that actuates the penetrating member is reengaged to achieve the new target depth which includes the distance to compensate for tenting. This process is relatively fast such as but not limited to under about 50 ms, so that it appears and feels like one operation to the user or patient.

In other embodiments, once the tenting T is calculated, the tenting amount T may be used for subsequent lancing events. A penetrating member controller (not shown) may include or be coupled to memory that will store this tenting distance. Thus, subsequent lancing events may be configured to account for the tenting distance on the first inbound stroke and achieve a desired depth without necessarily using a true depth type penetration stroke on each lancing event. Thus the depth for penetrating member penetration will include a desired depth D and the tenting T. The calculation of tenting T may be initiated on a first lancing event by the user and on any subsequent lancing events as desired by the user for recalibration of tenting purposes. In still further embodiments, the tenting distance T may also be adjusted by a certain amount (such as but not limited to ±1%, ±2%, ±3%, ±4%, ±5%, ±6%, ±7%, ±8%, ±9%, ±10%, or more) based on the time of day and hydration pattern of the user or patient. A lookup table containing different tenting distances T may also be used to pick off the desired amount of tenting compensation based on a number of variables such as but not limited to: time of day, hydration, age of patient, or other patient information.

In some embodiments, the penetrating member on the inbound path penetrates into the tissue during the tenting measurement. In other embodiments, the penetrating member does not fully pierce the patient while gathering information of tenting distance.

Figure 27:
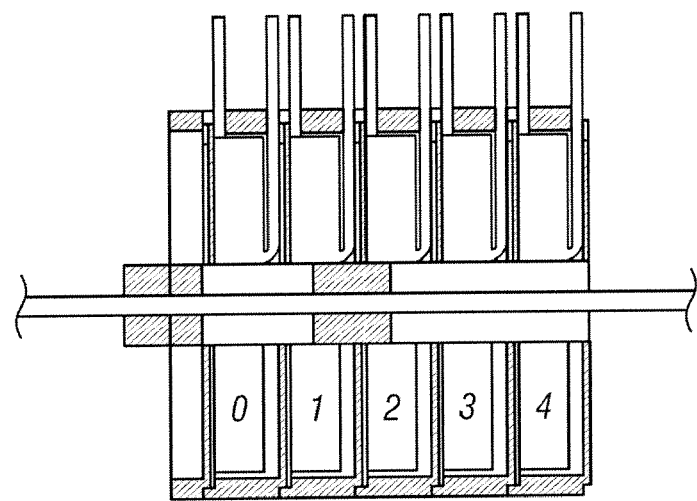
FIG. 27 shows another embodiment of a slug for use with the present invention.
Figure 28:
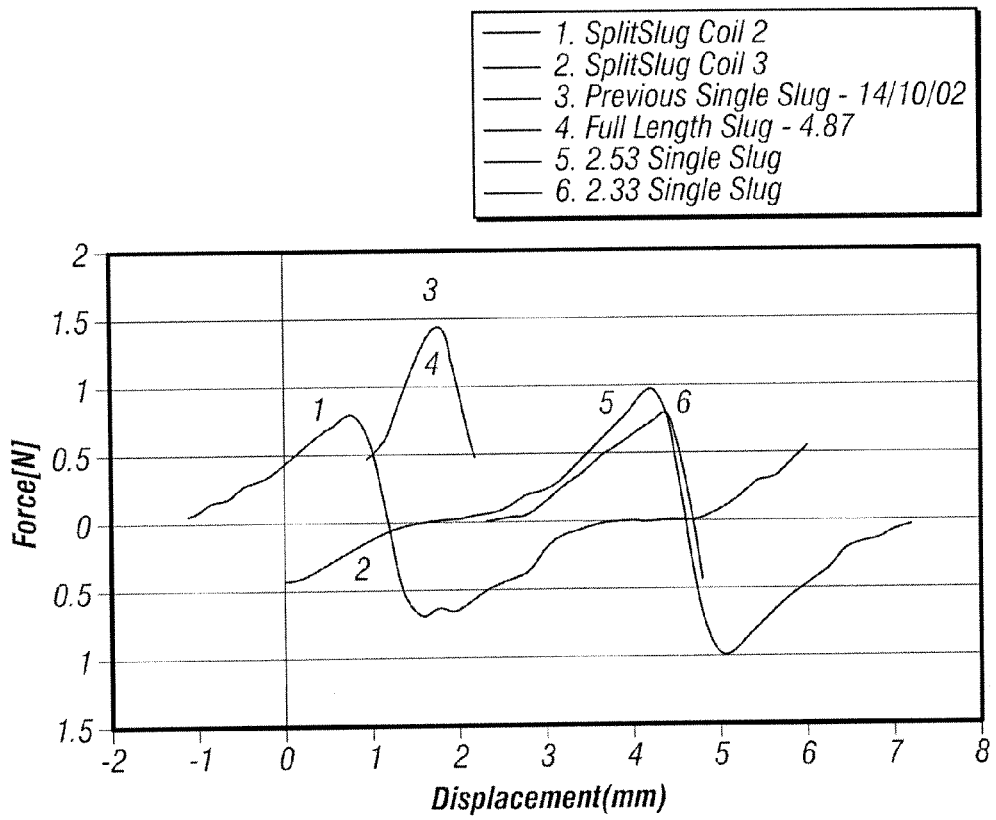
FIG. 28 shows a graph of force and displacement.

Referring now to FIGS. 27 and 28, further embodiments of the present invention will now be described. These embodiments relate to modifications for the electronic drive mechanisms used with the present invention.

Solenoid Study

The objective of the solenoid study is to further understand its operation and to look for techniques to further enhance the force capability. The existing solenoid design results in a very non linear force profile, and in all changes we are looking to increase the overall force while improving the low points in the achievable force.

2.1.1 Disk Thickness

Several modeling runs were conducted to study the effect of increasing the thickness of the coil disks on the peak coil force. It is thought that the disks are in saturation at the inner diameter. Therefore increasing the thickness of the disk reduces the saturated diameter of the disk, concentrating the coil flux closer to the centre. This increases the available force when the slug is away from the disk but has little effect as the slug approaches the disk, resulting in little change to the low points in the force profile.

For other embodiments, additional work was done looking at tapered disks and other methods of thickening the disk without compromising coil volume. From this it was seen that the slug force is greatly reduced once the front face of the slug enters the disk. In one embodiment, a 0.3 mm disk offers a good compromise between force and available coil volume without introducing flat (near zero force) points in a single coil energization curve.

2.1.2 Slug Dimensions

Several modeling runs were conducted to study the effect of varying the length and the inner and outer diameter of the slug on the peak coil force. In one embodiment, it was found that increasing the slug length was beneficial, so this was set at 4.87 mm. There was also a significant and increasing relationship between outer diameter and peak force—it was decided to settle on a slug OD of 3.6 mm in one embodiment. Over the range modeled, the effect of varying inner diameter was negligible, although slug mass was decreased.

The above table shows the effects of increasing the slug dimensions. The latter results from ID of 2-3 mm are extrapolated from the results and show the most promising increase in force available. This force is shown in terms of the Acceleration factor, i.e. the ability of the solenoid to accelerate the Total Carriage Mass.

From these results we estimate that some controlling factors are the Slug End Area, relating to the area available for the flux lines to act upon and the acceleration factor. Assuming this is correct, in one embodiment, the desired dimensions for increased force are an OD of 3.6 mm with an ID of between 2.6 and 2.8 mm to match to the existing end area at an OD of 2.4 mm 2.2 Split Slug In one embodiment, the concept behind the split slug was to even out the force profile over the whole slug throw by firing two coils simultaneously, whilst ensuring that when one slug is in an active force region, the other is producing no force and vice versa. This route was particularly interesting as a way of linearising the force profile.

2.2.1 Split Slug—Testing

In order to test the theoretical force curves, two pairs of metal slugs were made. One set was 2.53 mm long and the other set 2.33 mm. These sets were slid onto the end of metal wire with a spacer between the pairs to set the coil pitch at 3.28 mm. This spacer dimension was based on the simulation data suggesting an optimum gap of 1.41×coil pitch.

In one embodiment, a static test was performed—the force applied to the slug assembly by a single active coil at several fixed positions through the coil was measured. The end of the slug assembly was attached to a 600 g load cell, and the coil was attached to a track that allowed the slug to be accurately positioned within the solenoid. A 15.6 A constant current supply was applied to the coil for a duration that allowed the force applied to load cell to stabilize (35 ms).

In one embodiment, starting with the back edge of the slug flat with the back edge of the solenoid "zero position", the slug was moved in 0.2 mm increments through the solenoid; this allowed a force profile for the slug and solenoid to be recorded. Profiles were recorded for the 2.53 mm pair of slugs, 2.33 mm pair of slugs, and individual slugs at 2.53 mm and 2.33 mm.

In one embodiment, the static test force profiles for the split slugs can be compared to the results from a previous static test done on a full-length single slug as can be seen in FIG. 28 which illustrates a split slug force profile. A full length 4.87 mm slug generated 1.5N. The peak force for a 2.33 mm slug was 0.92N. The peak force for a 2.53 mm slug was 0.96N. The force on a split slug completely changed direction in 0.8 mm from peak to trough. At the overlap of coil influence a maximum of less than 0.1N could be applied to the slug in either direction.

In some embodiments, by going to a split slug design, the drop in the overall peak force available was significant. The peaks and troughs in force are still large enough to make it difficult to assume an effective linear control strategy. The large drop in force is likely due to plate saturation. The plates closest to the active coil saturate when turned on and the magnetic field extends to include the next set of plates, the smaller slugs are too small to make effective use of the force provided from these more distant plates.

2.3 Electrical Improvements

In one embodiment, the main aspect of the electrical system is the power supply and the PET drive. This system takes up considerable space as large capacitors are used to supply sufficient energy to the solenoid.

2.3.1 High Voltage Drive

Figure 29:
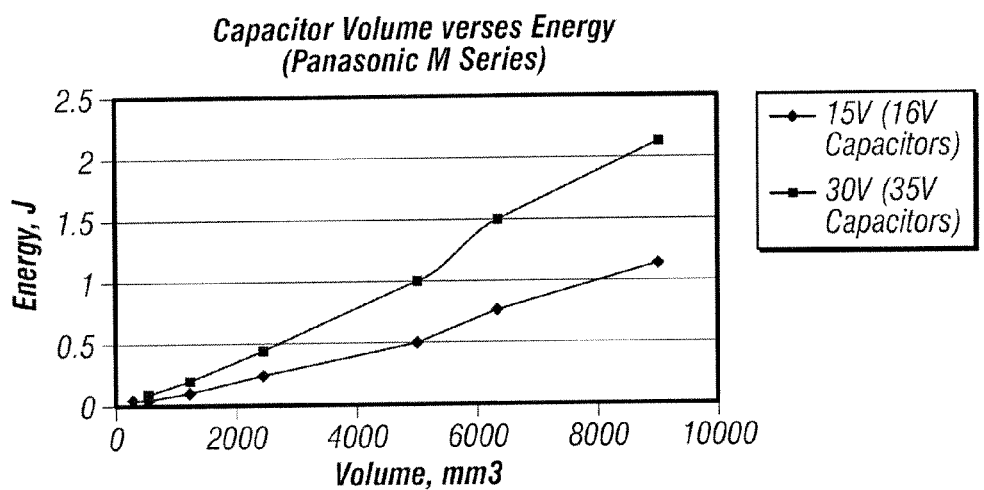
FIG. 29 shows a graph of electrical performance.

Referring now to FIG. 29, in one embodiment, the current power supply is based around a 15.5V boost converter using 20V rated FETs and 16V rated electrolytic capacitors. By increasing the voltage which the boost converter supplies, the energy stored in the capacitors is significantly improved in accordance with the equation: Energy=$\frac{1}{2}CV^2$. A higher voltage system would use different capacitors and transistors, but the capacitance used to achieve equivalent energy storage would be greatly reduced and consequently the size of the capacitors.

Approach

In one embodiment, the next common voltage range of capacitors above 16V is 35V and therefore it was decided to test a 30V system using an equivalent energy capacity to 13600 µF at 15.5V which is approx. 3300 µF at 30V. In addition the FETs tested were dual FET packages rated 55V—Part No. IR7341

In one embodiment, a test were devised to give a comparison of available force between the 15.5V and 30V systems. Static tests could not be used to obtain a force profile for the higher voltage system, as a steady supply that could provide the desired energy to the system could not be acquired. A dynamic test was seen as the best alternative and most accurate measure of performance for a 30V system.

Figure 30:
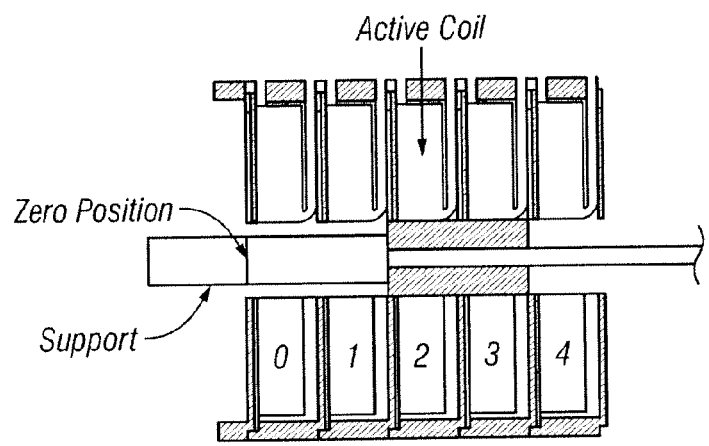
FIG. 30 shows a zero position for a solenoid driver.

In one embodiment, the coil was placed vertically so that the slug could be fired upwards to reduce the effects of friction in the system. The slug assembly's weight was adjusted so that it was exactly 1 g, this enabled the slug to be fired at a slower speeds which reduced encoder noise. A logic analyser running at 100 Mhz was attached to the output of the optical encoder in order to log the time at which encoder edge inputs occurred. The slug was moved so that its back edge was flat with the rear of the solenoid "zero position" (see FIG. 30).

First—the central coil was pulsed at 100 μs to 1500 μS at 100 μs intervals to check that the acceleration profile was independent of pulse length.

Second—the starting position for the slug was raised through the coil at 0.5 mm intervals to 2.5 mm and the central coil was fired for 1200 μs at each of these positions.

Finally—in one embodiment, the extra weight on the slug assembly was removed (making the weight 0.28 g), this was in order to get a speed comparison to previous tests performed at 15.5V. The slug was moved so that its back edge was flat with the rear of the solenoid and the central coil was fired for 1200 μs.

During all of the tests at 30V, the current that could be drawn to charge the capacitors was limited to 0.1 A (0.2 A was allowed for all previous experiments at 15.5V). For a given starting point all pulses accelerated the slug along the same acceleration profile. FIG. 31 shows the speed traces for different pulse lengths in μSeconds.

In one embodiment, by incrementing the start position of the slug towards the active coil, the acceleration of the slug appears to increase. The noise in the system means accurate measurement of the discrepancies between the acceleration is virtually impossible. However, it was possible to calculate the average force over a broad section of the force profile by using the maximum speed achieved and the associated time to obtain an average acceleration value. The mass was then divided in to obtain the force. The noisy position data was not significant over large displacements and therefore an average force within those displacements could be calculated using the data shown in FIG. 31.

In one embodiment, by removing the extra weight from the slug and firing it from the zero position with the middle coil the slug reached a maximum speed of 15.5 m/s. The energy in the 3300 μF capacitor with a limited 0.1 A supply was sufficient to accelerate the slug assembly to 15.5 m/s and then decelerate the slug to a complete stop without any deterioration in the acceleration profile. The lower voltage system showed some deterioration in acceleration during the braking section of an equivalent test.

The acceleration profile is independent of the pulse length. The force on the slug has been increased significantly with no detrimental effects observed. This has been done with the use of smaller capacitors as highlighted by the lower mass experiments. The average force produced by the 30V system was 6.6N compared to an average force of 3.7N for the 15.5V system. The clear advantages of this approach are:

Smaller capacitors

Higher forces, giving faster acceleration/deceleration, higher speeds and increased ability to pull out, push in static/standing forces Increased magnetic field influence (potentially fewer coils used)

2.3.2 Recommended Next Steps—Electronics Optimisation

Change the 15.5V PSU rail to a 30V rail and change the capacitor size to 3300 mf.

A possible further avenue of exploration is to measure PSU energy use during the complete firing cycle and use these results to set the absolute minimum size of the capacitor.

Redesign of the boost converter using a transformer to optimise the efficiency of the converter at this higher voltage.

A new rig is currently being designed in order to obtain the higher positional resolution needed to gain an accurate force profile.

3 Control System Development 3.1 Objective

The launcher system technical objectives include:

accelerating to a speed of at least 4 m/s.

achieving a positional accuracy on stopping of +/−0.05 mm at any set depth between 0.5 and 3.5 mm retracting from the skin under control at slow speed The objectives of this part of the work were to create a model to test control algorithms for the system and to create and test the models over a wide range of conditions.

3.2 Approach 3.2.1 Modelling Environment

One embodiment of the launcher system was modelled in Matlab/Simulink. Matlab is a numerical modelling environment able to manipulate and compute mathematical models based on matrices. It is both command-line and script driven. Simulink is an extension to Matlab. It is a graphical environment which allows dynamic system modelling using the notation and conventions of control system block diagram models. Models are defined, initialised and then a simulation of their dynamic behaviour is run over a specified time sequence. Using Matlab scripts, multiple model runs were executed enabling fast analysis of model sensitivity to variables.

3.2.2 Model Composition

The Simulink model created is in two parts:

the controller, which runs the control system software. This handles all phases of the launch and retract cycle the test shell, which is a model of selected physical features of the launcher and the electronic input/output system, essential for testing the controller.

Figure 33:
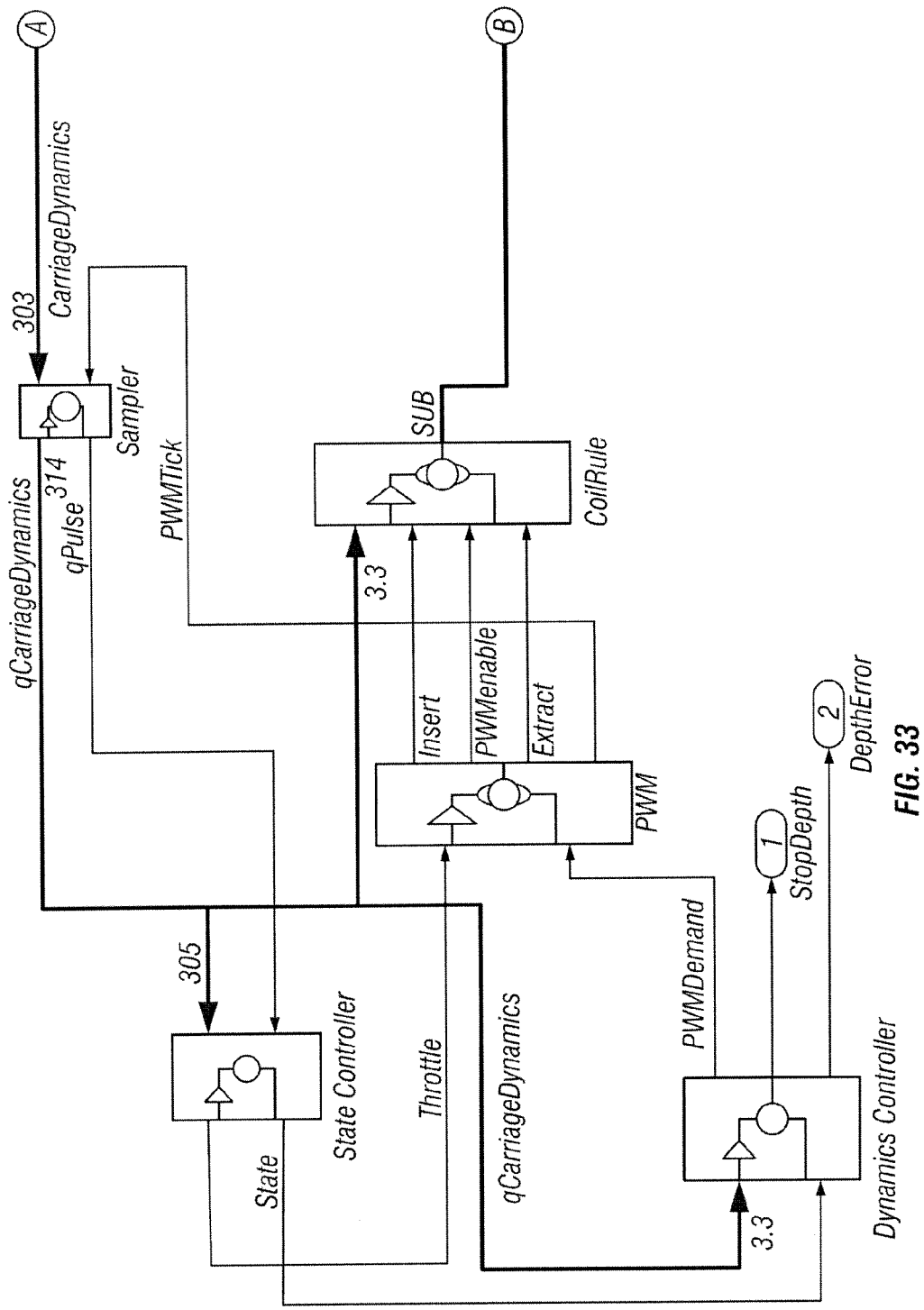
Figure 33:
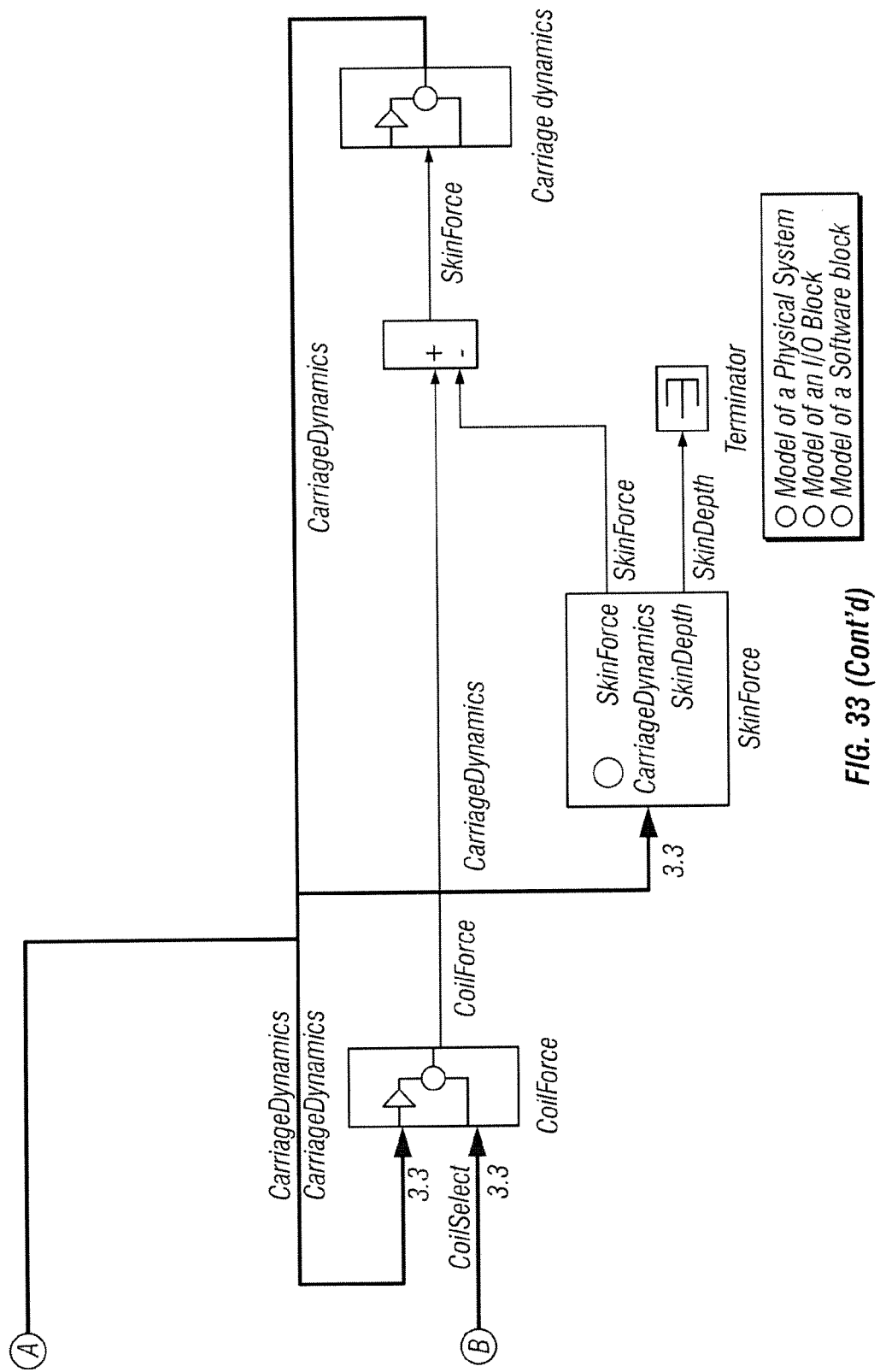

Referring now to FIG. 33, one embodiment of a launcher system model is shown. The approach was modular and iterative—the different system functions of sampling, controlling speed, timing the coil current were split so that each could be improved in isolation. The components of the model are shown in FIG. 7. During the development of the model, some further decisions on implementation were taken—chiefly on the PWM/Coil drive system.

The controller has two parts—the state controller and the dynamics controller. The state controller is designed to execute the whole launch cycle—acceleration, braking, then slow and fast retraction. The dynamics controller deals with adjustments to the coils to achieve control of the carriage.

The test shell and the controller were both initialised from a Matlab script which sets up global constants for the current simulation run. During the run, simulation data is output to Matlab where it can be stored and later analysed. The main focus of work during development was on achieving a tight positional accuracy on insertion.

3.2.3 Realism

In operation, the launcher electronic system has many interactions but the system elements with the biggest impact on the control algorithm are:

the encoder the technique used to drive the coils the coils themselves.

The some characteristics of the launcher system which were used in the model are tabulated here:

| Skin | |
| --- | --- |
| Skin offset from rest position | 4 mm (fixed)[1] |
| Skin force gain | 114 N/m gives 0.4 N @3.5 mm |
| noise s.d. | 3.5% |
| depth setting | 0-3.5 mm in 0.1 mm steps |
| Encoder | |
| Number of channels: | 2 |
| Positional resolution: | 42.32 μm |
| Standard deviation of positional measurement | +/−1 μm |
| Carriage | |
| Mass | 2.98 g |
| Coil | |
| Coil force gain | 3 N peak |
| Coil offset, from zero position | 3.5 mm |
| Coil pitch | 2.33 mm |
| PWM | |
| PWM period | 50 μs |
| resolution | 8 bit |
| throttle setting | 50% |

3.2.4 Implementability

In order to be fit to implement in a low-end microcontroller, the control algorithm must be constructed from a limited set of mathematical operations and run at a speed, which will fit within its computational capability. In outline, the mathematical functions that will be used are:

16-bit fixed point add/subtract 16-bit fixed point multiply/divide

Look up table.

During this phase of testing, full 32-bit floating-point arithmetic was used.

3.2.5 Force Control—Pulse Width Modulation and Coil Firing

To achieve control over the level of coil force developed, the model contains a PWM module. This pulses current to the coils in time slots of 50 ms. Within this period, the time resolution was 8 bits, giving 256 selectable firing durations. Averaged over the PWM period, this gives direct control of the average force.

Figure 34:
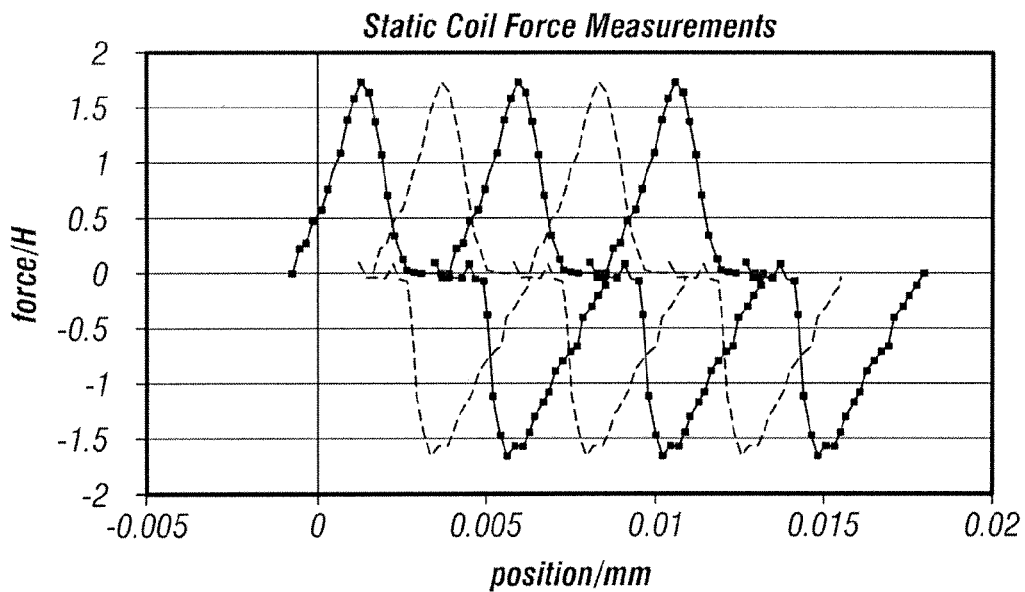

Referring now to FIG. 34, a 5 Coils Force Profile is shown.

A simple rule was needed to decide which coil to fire during the cycle. Static force tests on the solenoids provided a force—distance profile (see FIG. 34). The controller was programmed to use the following simple switching rule:

In this embodiment, at all positions, select the coil that will generate the greatest force.

This rule was encoded in 2 tables of 4-elements containing the switchover points for the 5 coils for insertion and retraction. Because of the modular approach, the coil was treated as an instantly responding actuator. This means that other combinations of coil switching e.g. 2 coils at once can be employed within this module without affecting the architecture of the system.

3.3 Control Techniques Studied

The physical system (plant) under control is a moving mass system with almost instantaneous direct control of the applied force. The only plant information is the position of the carriage. Two techniques were studied to achieve positional control.

3.3.1 Acceleration-Based

In one embodiment, acceleration was measured by differentiating the position signal twice, and averaging this signal over the PWM period. This smoothed value was used as an input to a simple proportional controller, employing no integral or derivative action—see FIG. 35. The output was fed to the PWM module as a time demand—which is translated to a force as described above. The results of this processing were favourable.

Figure 35:
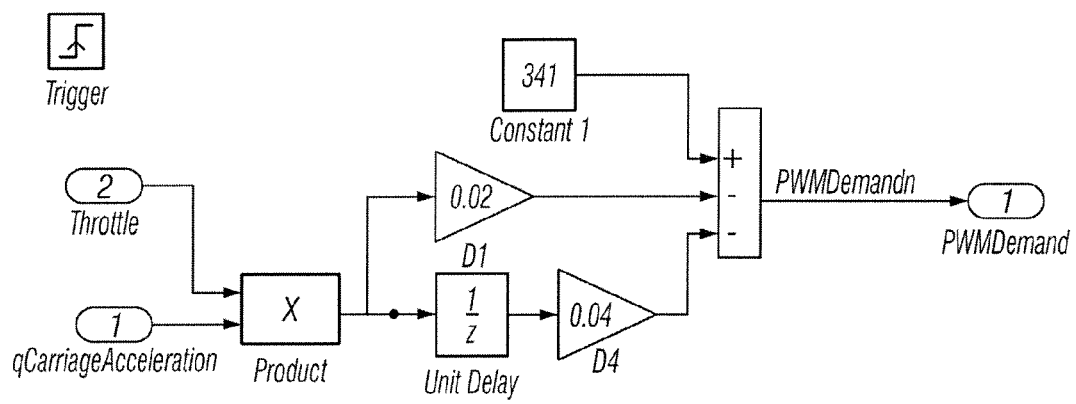

As seen in FIG. 35, a portion of the control algorithm—Acceleration control, is shown.

In this algorithm, the throttle is a logic signal, and the PWM demand is evaluated when triggered every PWM period (50 ms). The PWM demand is a smoothed version of the acceleration error as the sum takes inputs from both the current and previous PWM periods. There are three model parameters—the constant PWM value and the two gain Figures.

The rationale was to create a servo system which would respond quickly by adjusting the coil force in response to any given acceleration demand. If this were possible, velocity and position could be controlled accurately as a result. The acceleration demands are set according to a state controller which runs the launch and retract cycle and is common to all the models discussed here.

A side effect of measuring the acceleration is a real-time measurement of the coil force during the previous PWM period. The acceleration controller's reason for being and its main error input is the variation in coil force caused by the solenoid.

Figure 36A:
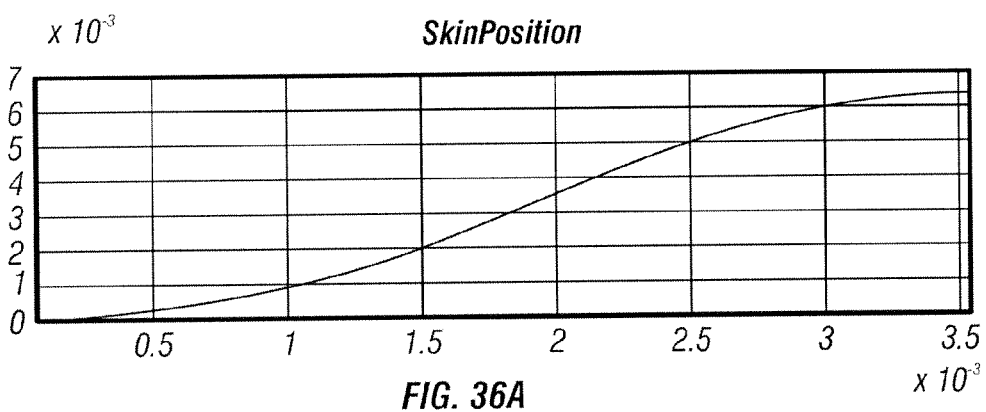
Figure 36B:
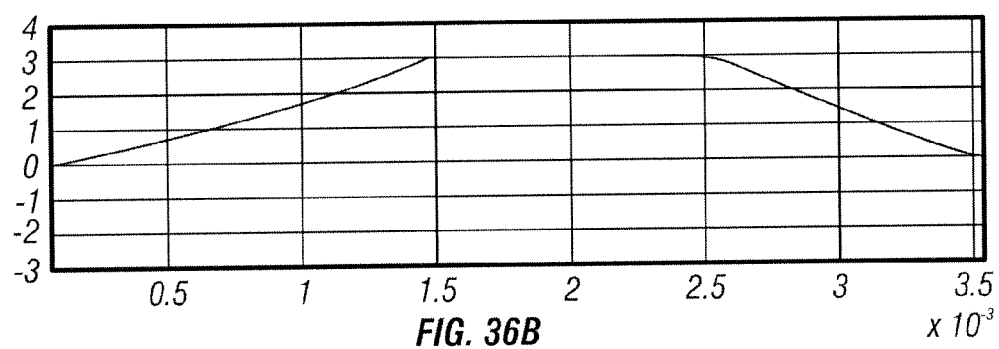
Figure 36C:
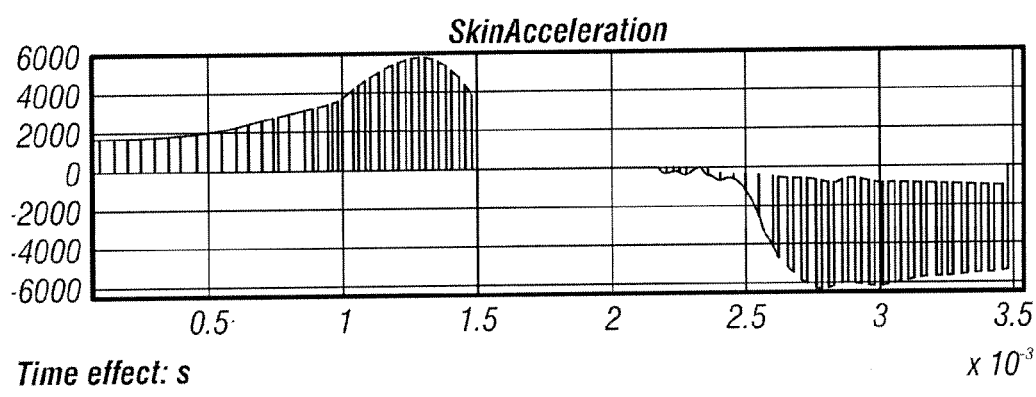

In one embodiment, a forward-looking condition was then used to initiate braking. The results of testing this algorithm can be seen in FIG. 36 and further discussed in FIG. 44. A sign of the correct operation of this algorithm is the variation in PWM duty cycle in sympathy to variation in the coil force, which can be seen. One of the initial findings about this controller was that it is sensitive to gain values that are coil-dependent. It also failed to use the maximum force regions of the coils to full advantage, because it was targeting an acceleration value which was achievable even in a low coil force region. This was quite unsatisfactory as a hard braking method.

Following initial testing of this algorithm it was decided to focus on the energy control algorithm. The acceleration control algorithm was not tested with later model enhancements.

3.3.2 Energy Based

In outline, the 2nd technique of controlling to achieve positional accuracy was based on equating the energy available to stop the carriage in the remaining distance with the kinetic energy, which it has at the skin entry point.

The approach was to send the carriage on a braking profile that uses a fixed fraction (the energy set point) of the total work available from the coils. In practice, this is achieved by setting the PWM value at a constant fraction of 100% duty. Because the coil force varies with carriage position, the effect of this on the carriage is to decelerate it on an uneven speed profile. The speed profile can be calculated from a coil force map, which is obtained experimentally, is stored, and forms part of the control algorithm.

Figure 37:
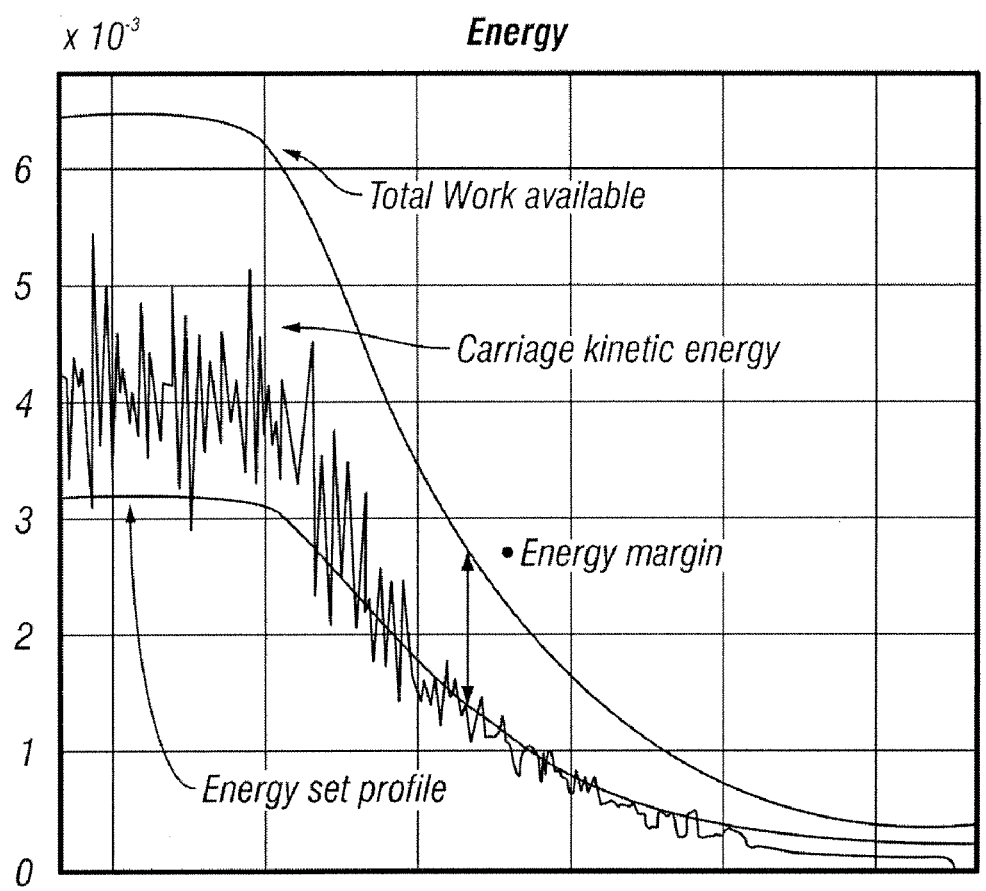

Three important quantities are now introduced. These are shown on FIG. 37:

The energy/speed set profile. For a given energy set point, it is known what the coil force, and therefore the work done by the coil, will be, throughout braking. The work done on the carriage by the skin is also known. By adding these together, the total work done on the carriage is calculated. Therefore, the idealized profile of carriage kinetic energy against distance can be calculated for the braking phase. This is used as the set point profile for control. Assuming there are no errors in the prediction of force on the carriage, this is the profile the carriage will follow when braked at the energy setpoint with no intervention from the controller.

The total work available to brake the carriage from the skin+the coils. This is all the work that can be done on the carriage as it travels to the desired skin depth. It is also the profile which the carriage would follow under the action of 100% coil braking and skin force. This defines the control envelope—if the carriage kinetic energy departs outside this curve, it is certain to overshoot the stopping point.

The difference between the energy set-point and the total work available is the energy margin. This spare work is used to correct for errors between the actual speed and the set speed.

In principle, to obtain a high level of braking, a small level of energy margin is used. To compensate for a large level of errors, a larger energy margin is used. The trade-off between the two can be reduced by improving the performance of the in-built control system. A diagram of the energy control algorithm is shown in FIG. 38.

Figure 38:
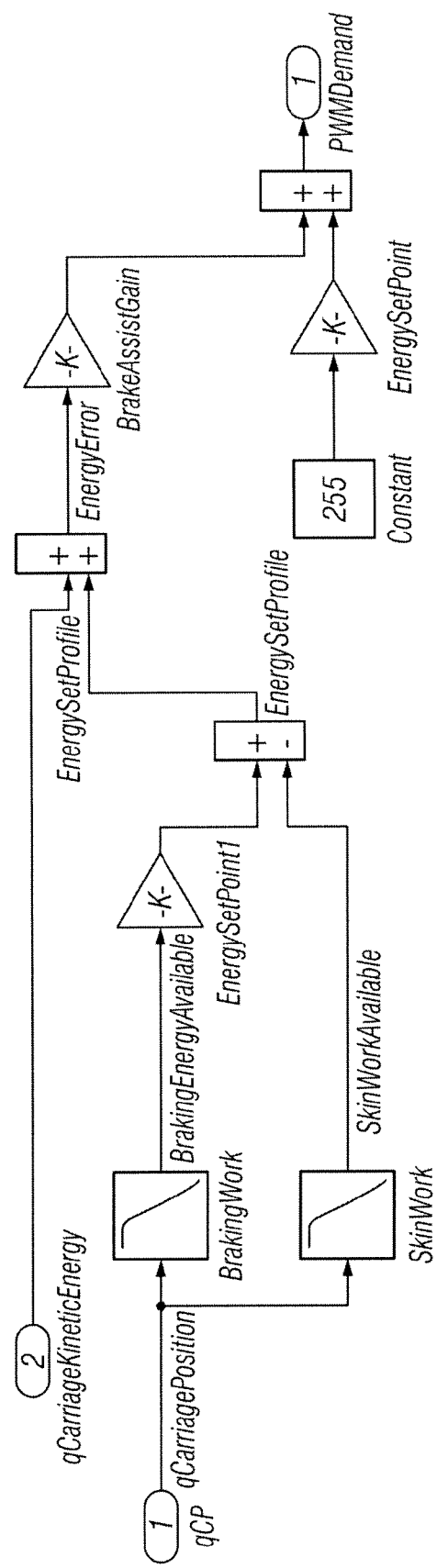

Referring now to FIG. 38, another portion of the control algorithm—energy control, will now be described. In this embodiment, this algorithm is continuously evaluated. A lookup table is used to read the current Figure for "braking work". The "skin work" is pre-calculated by a formula based on skin depth and is also stored in a lookup table. The energy set profile is calculated from the sum of skin work and braking work (scaled). The error (energy error) produced by subtracting this from the carriage kinetic energy is then scaled by a gain and modifies the fixed PWM value.

The main error source which the controller acts on is the error between the predicted force—distance relationship of the skin and its actual value, together with the associated variation (skin noise). This is therefore one of the main testing usements.

Implementation—Data Storage

In order to use the concept of a dynamic energy set profile as an input to the controller, the carriage force profile needs to be stored. This is more sophisticated and data intensive than acceleration control. Even so, 0.1 mm resolution can be achieved to 4.0 mm depth with only 40 stored values.

Following initial testing, the performance of the energy-based control strategy was promising. In some embodiments, the positional error on stopping was between −0.5 mm and −0.15 mm.

After some testing of different methods for calculating the energy set profile, it Was decided to use the following formula to calculate it:

1. Take the estimated work available from the skin from entry to stopping point
2. Add in the work available from coil braking, scaled for the energy set point 3.4 Sensitivity Study The control approach described above is data-intensive. There are several parameters, which affect the performance of the model to varying degrees. An illustration of the variables within each module and the extent to which they are under control is shown in FIG. 39. During the course of this study, it was desired to test the effect of variation in the important factors below to ascertain the level to which they affect system performance. Fortunately, the models can be run repeatedly to investigate these variables over a range of values. During the sensitivity testing, roughly 100 simulation runs with different parameters have been completed.

Referring now to FIG. 39, the nature of the module variables will now be described. The effect of each of the parameters highlighted in bold above on stopping accuracy has been checked. It was decided that the level of launcher friction was so low as to be insignificant in comparison to the other active forces (coil and skin force) and that therefore this was not essential to the model.

Encoder Noise

Figure 40:
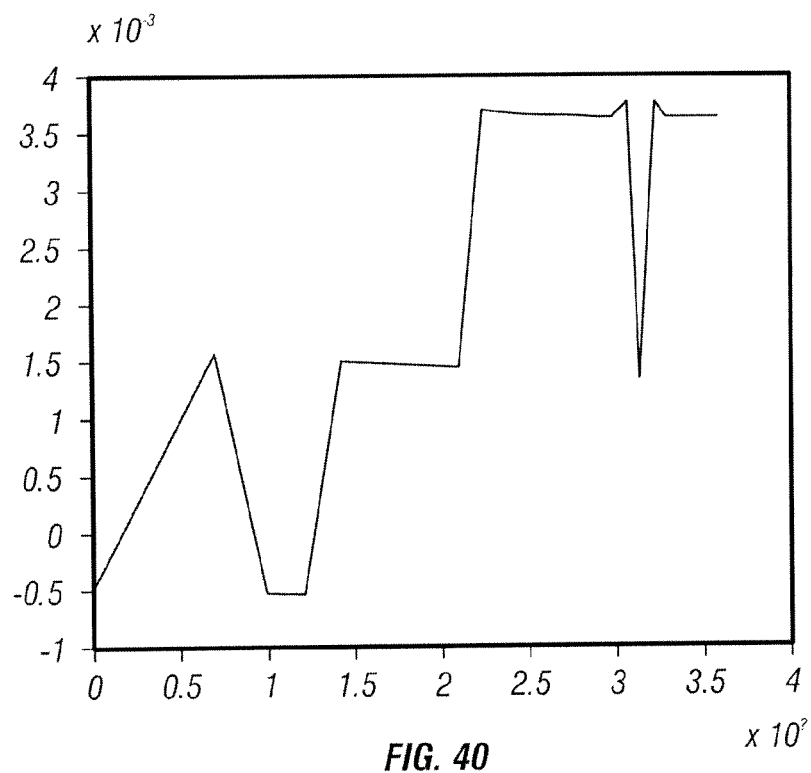

In one embodiment, positional noise from the encoder affects velocity and acceleration measurements. The effect was characterised experimentally. From experimental data, the standard deviation of this noise was found to be +/−1 mm. The noise component of this signal was added into the model as an error signal. The effect on the velocity measurement can be seen in FIG. 1—a noise signal is created. Throughout modelling, a value of 1 mm was selected. The limit on encoder noise beyond which positional control was significantly degraded was 2 mm. A more complete graph of this effect is shown in FIG. 40.

Coil Force Measurement

In one embodiment, the controller braking profile is based on measurements of the coil force conducted in a static force test. The effect of variations in these forces was studied and the result is shown in FIG. 40. For the tests shown in this Figure, the predicted coil peak force was 4N. The actual coil force was varied from 2 to 6N. As can be seen, the effect of underestimating coil force is much less critical than that of overestimating it. The stopping accuracy was generally within 0.1 mm of the desired stopping point, except at low levels of actual coil force. In that case, overshooting was more serious, at up to 0.3 mm at 3 mm set depth.

Skin Entry Speed

In one embodiment, the skin entry speed was targeted so that during braking, the carriage kinetic energy would converge with and run down the pre-programmed profile. Because of the fact that increased skin penetration depth brings more energy available from the coils to stop, this naturally means that the deeper the stopping point, the faster the entry speed.

This way of targeting skin entry speed is not optimised for flight time, as the carriage could be driven faster in the early part of its flight, then braked before entering the skin. This refinement is particularly relevant for shallower depths but was not seen as useful to the set depth accuracy problem. Either side of its velocity set point, the braking controller has a "capture window" within which it can bring and keep the velocity under control during braking. Outside of this window the carriage either ends up overshooting, because the energy margin has been used up, or the carriage has insufficient momentum to enable it to reach its desired position and it stops short.

A refinement that could be tested to deal with either of these eventualities was asymmetric gain.

Coil Usage

During the full insertion and retraction cycle, coil 0 alone is used for braking and acceleration. Because this aspect of the model is fully parametric, the force profile for predicted coils and actual coils can be quickly modified and retested when other coil layouts are tried.

Sensitivity to Errors in Skin Force Prediction

Figure 43:
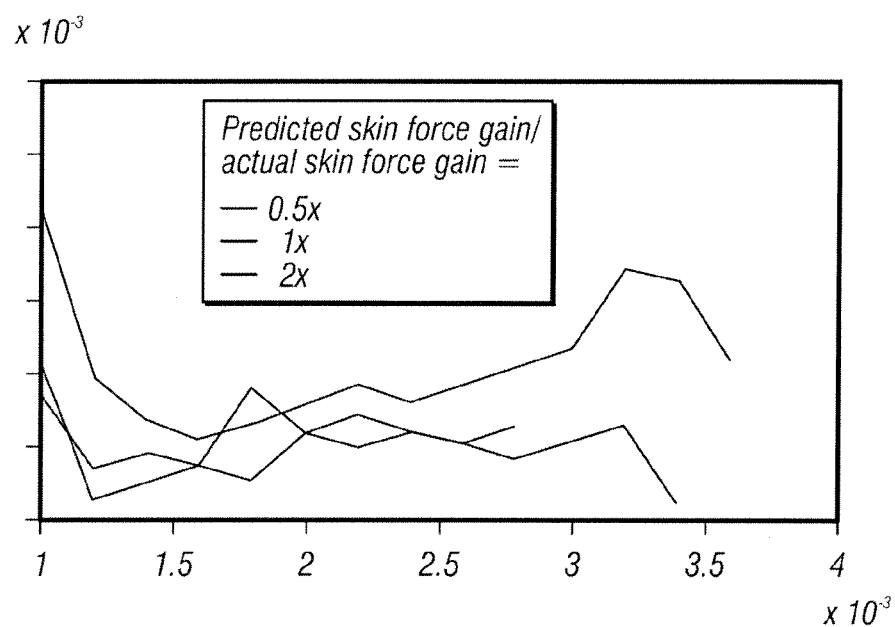
Figure 44:
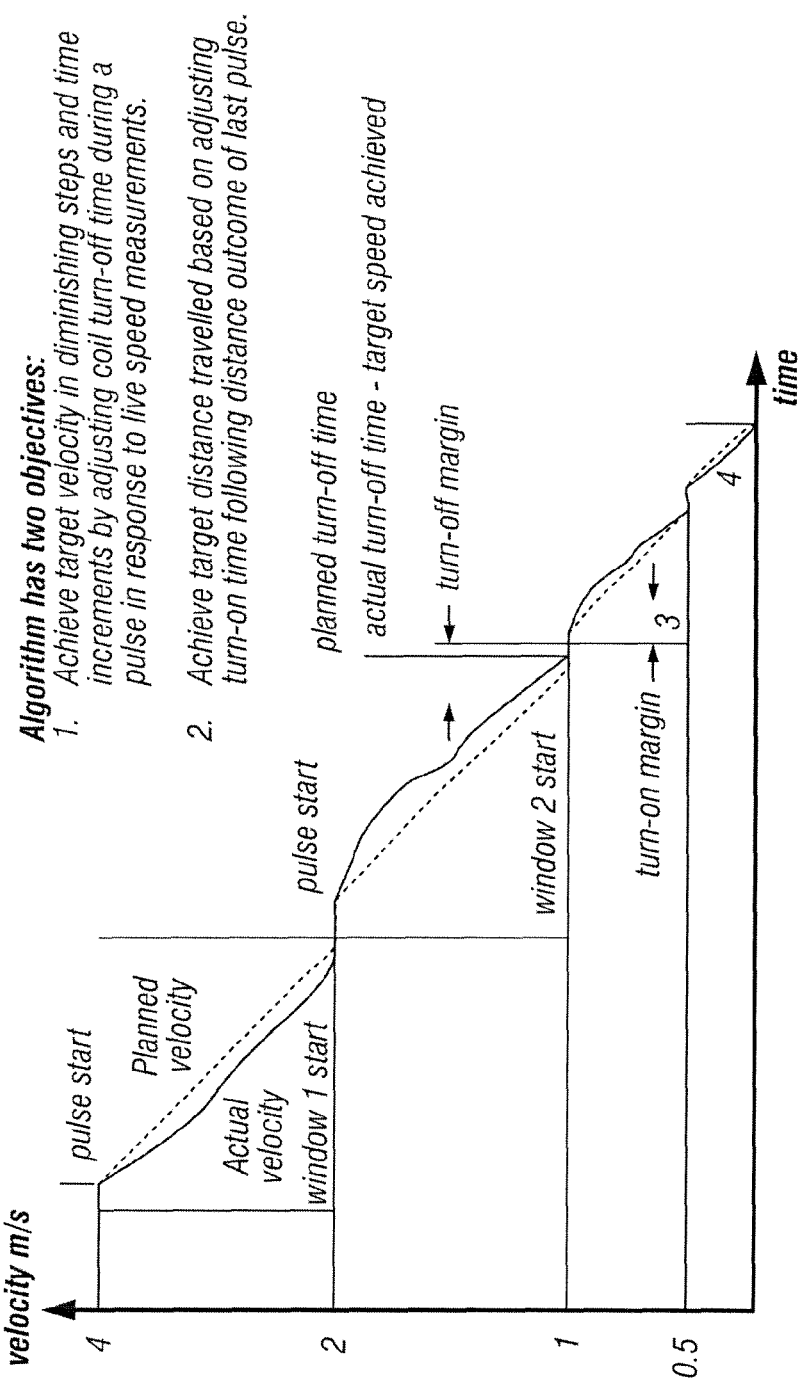
FIG. 44 shows a graph of penetrating member velocity versus time for one embodiment of a control algorithm according to the present invention.

In one embodiment, the algorithm improves positional stopping performance by including a prediction of skin force and hence energy. This estimate was obtained from experimental data. By including this prediction, it introduces sensitivity to that data. Testing was conducted to explore the effects of errors of factors x2 and x½ in the average skin force for comparison with nominal data. The results are shown in FIGS. 43 and 44 below show these three skin force gain scenarios.

Figure 42:
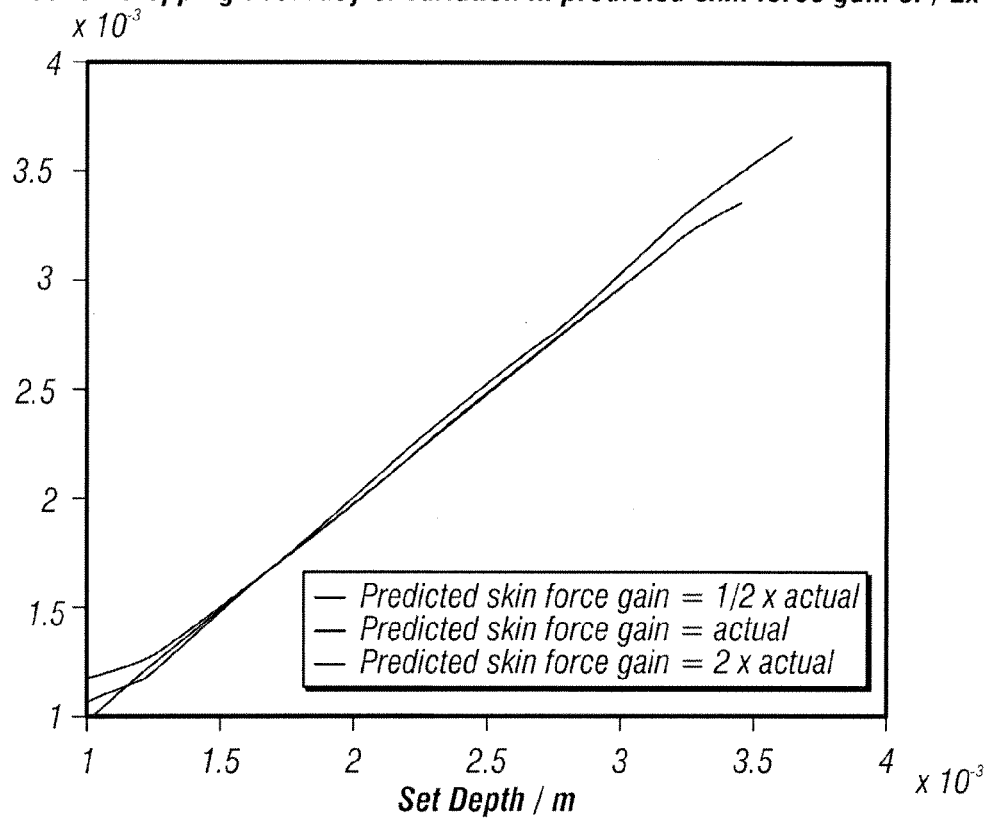

The graph in FIG. 42 is encouraging—it shows the overall performance of the algorithm over a range of set depths and skin force gains.

At deeper set depths, the sensitivity of the positional accuracy to errors in skin force is greater than at lower depths. This is to be expected intuitively, as the work done by the skin increases as a quadratic function of distance.

At lower set depths, the entry speed was simply too low to enable the algorithm to work effectively. This needs more complete testing and probably a different approach for shallow entry. It should be borne in mind that in this testing, the energy control concept was only implemented within the skin and not in free space.

Figure 41:
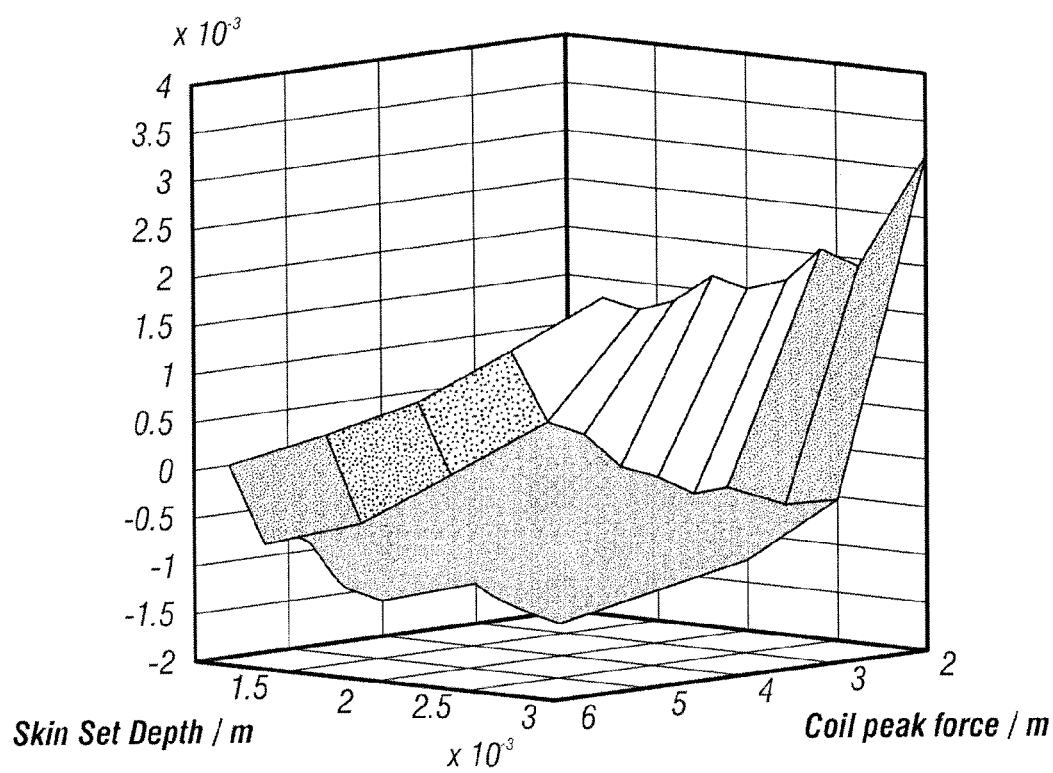

One of the best ways counteract errors in skin force prediction is to make the total possible error small in relation to the coil force, which can be controlled. This is done by increasing the coil force. The effect of this can be seen in the earlier FIG. 41 and also in FIG. 43. The three traces show simulations conducted at the same coil force and stopping error was greater when skin force was underestimated (red trace).

- In general, the control algorithm involves using a pre-programmed speed profile at a fixed coil throttle setting and using what coil force is left to cancel out errors arising from skin and other forces.
- Studies of sensitivity to errors in predicted skin force, encoder noise and to variation in coil force have been conducted and the effects recorded.
- Using a higher force in relation to skin force enables more precise positioning to be achieved.
- Using a peak coil force of 3N, insertion positioning to within +/−0.1 mm can be achieved over a range of set depths from 1 to 3.5 mm and over a range of skin—force curves. At lower coil forces, positioning accuracy is degraded.

Control System Development
- Control algorithm—Test the idea of using an asymmetric gain on the energy error signal during braking. Include a model of the launcher friction. Change the method of calculating the energy set profile for shallow skin entry.
- Implementation—Construct a prototype system using MatLab RTW to produce real time code to run on MatLab XPC real time PC system. This will allow further testing and development of the control algorithm on the real hardware and skin.
- Implementation—Model the system using only 16-bit arithmetic and change the energy-based algorithm to a velocity-based one to maintain signal precision.
- Implementation—Modify the algorithm to operate at the (much slower) PWM frequency, rather than in near real-time.
- Testing—Test the revised algorithms using a similar test suite as described here.
- Experimental/mechanical data—Update the coil force graphs and dimensional parameters for the latest mechanical layout 4 Position Sensors—LVDT In one embodiment, a linear variable differential transformer is an alternative to the optical encoder as a means of position and speed sensing. In a successful realisation, the chief advantages over the optical encoder are:
- a higher linear resolution
- a smaller package size and a shape which is easier to integrate
- The ability to provide position updates to the microcontroller on request, rather than having an interrupt-driven system, which aids software design.
- Lower cost The simple basic design of the LVDT is versatile and offers a wide scope for customisation. LVDTs also offer fast dynamic response, they can make measurements at up to ¹⁄₁₀ of the driving frequency on the primary winding. For this application, that translates into an ability to sense movement at >50 m/s. Although widely used in industrial equipment, they are rarely found in low cost consumer items. The objective for this study is to prototype a design and to find an optimal solution for the launcher.

4.1 Design Issues

Operating frequency Needs to provide positional updates at a rate close to that of the current sensor (4-5 ms). May be possible to go to 10 ms. Assuming an ADC system is used where the ADC can sample successive peaks, then the driving sine wave source frequency is in the range 100 kHz to 250 kHz. For this application it should be able to sense movement at >50 m/s. The maximum frequency of the coil drive is limited by air coupling Resolution To match the encoder resolution uses 1024 positional steps—10 bits Moving weight Must not adversely affect the performance of the solenoid—carriage system.

Packaging Length <30 mm, diameter <8 mm

System BOM cost, including electronics <$3.00

Throw distance 8 mm

Table 2: Outline LVDT Specification

The LVDT electronics is comprised of the following elements:
- Drive circuit. For low component count and design simplicity, it makes sense to control the LVDT drive directly from the microcontroller.
- Sense/sample circuit. Must provide gain and offset zeroing and also the ability to hold the signal for the ADC.
- ADC. Must provide sufficient conversion speed to satisfy the frequency usement.

4.2 Coil Parameters 4.2.1 Coil Disposition

The layout of the coils in commercial LVDT products is such that they may be used in a single ended mode, ie a moving soft metal slug enters from one end only. A simpler design could be a centre primary with two secondary windings. In this case the slug length is the primary length+a single secondary length.

By careful design of the numbers of turns and dimensions of the primary and secondary some gain can be achieved within the LVDT to improve the signal to noise ratio of the secondary signals.

4.2.2 Single Coil

LVDTs traditionally have two coils, each of which produces an output which is linearly proportional to the position of the slug. When subtracted, the two voltages cancel at a zero position. This removes the effect of air coupling. If the sensing/sampling circuit can be designed such that the air offset is zeroed then a single secondary coil can be used. This would produce significant packaging benefits.

4.2.3 Recommended Next Steps—LVDT

Purchase a commercial LVDT and develop suitable drive circuitry for interface to a microcontroller system.

Referring now to FIG. 44, a predictive braking algorithm is shown. By modeling the penetrating member driver and the tissue to be penetrated, a "road map" of short is provided to determine when the braking should be applied to achieve a desired depth. Feedforward systems are described herein and are used in combination with a lancing device such as that described in commonly assigned copending U.S. patent application Ser. No. 10/127,395. Feedback is used in combination with feedforward. In this embodiment, feedforward may be used for braking of the penetrating member or more precisely, the slug driving the penetrating member. The feed forward algorithm may be stored in a processor used to control the penetrating member driver. FIG. 44 shows in detail how the planned velocity is used to determine how to reach a desired depth. In one embodiment, the entire inbound path is traveled in under 10 ms, which is faster than most humans can see. Hence the need for feedforward to provide a planned velocity so that the accurate depth can be reached without lag and/or instability that may be associated with a feedback only system.

As each device is manufactured, each driver may be modeled during manufacturing to adjust the model for each driver. In other embodiments, a standard model may be used.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue.

Figure 45:
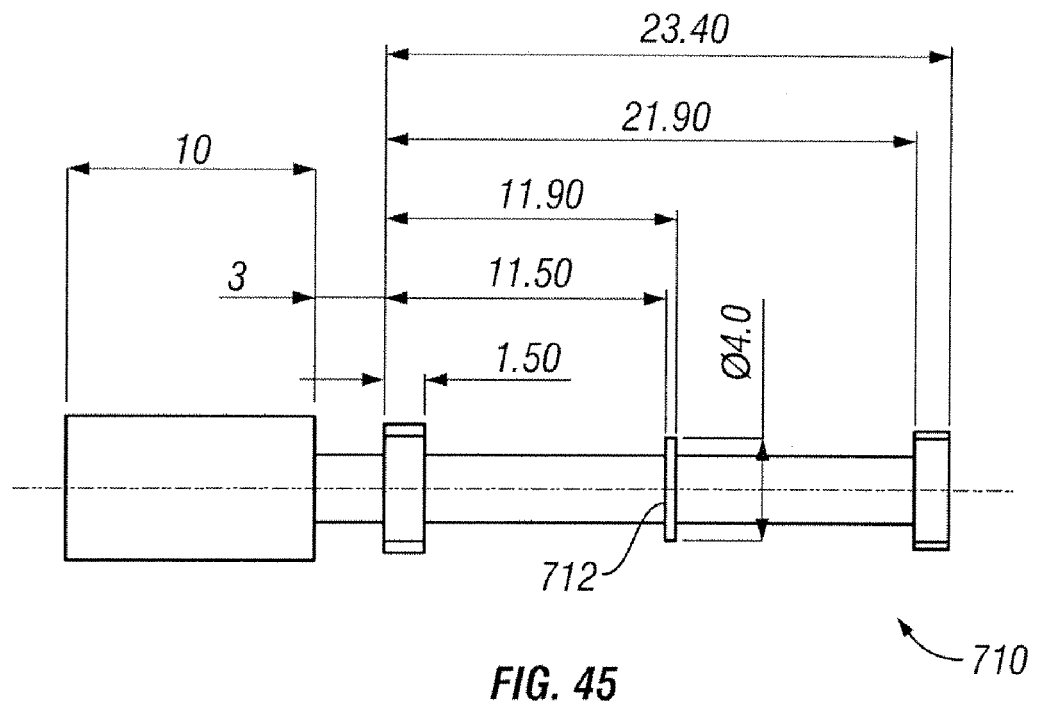
FIG. 45-46 shows one embodiment of a electroic drive mechanism.
Figure 46:
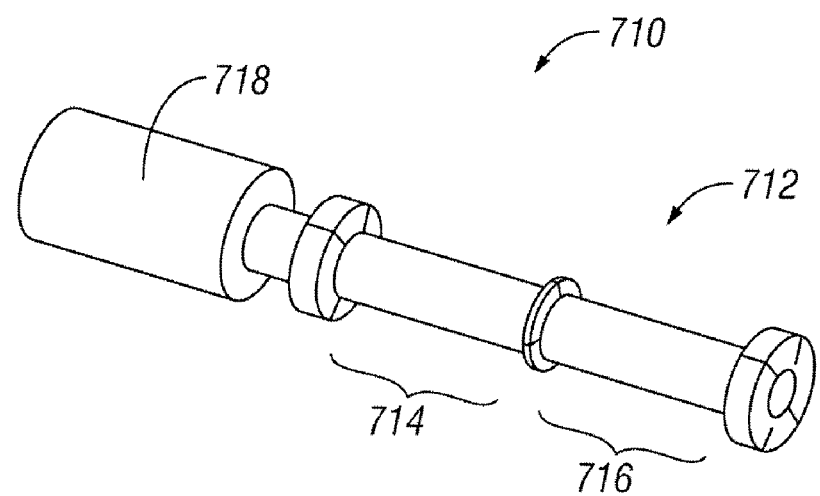
Figure 47:
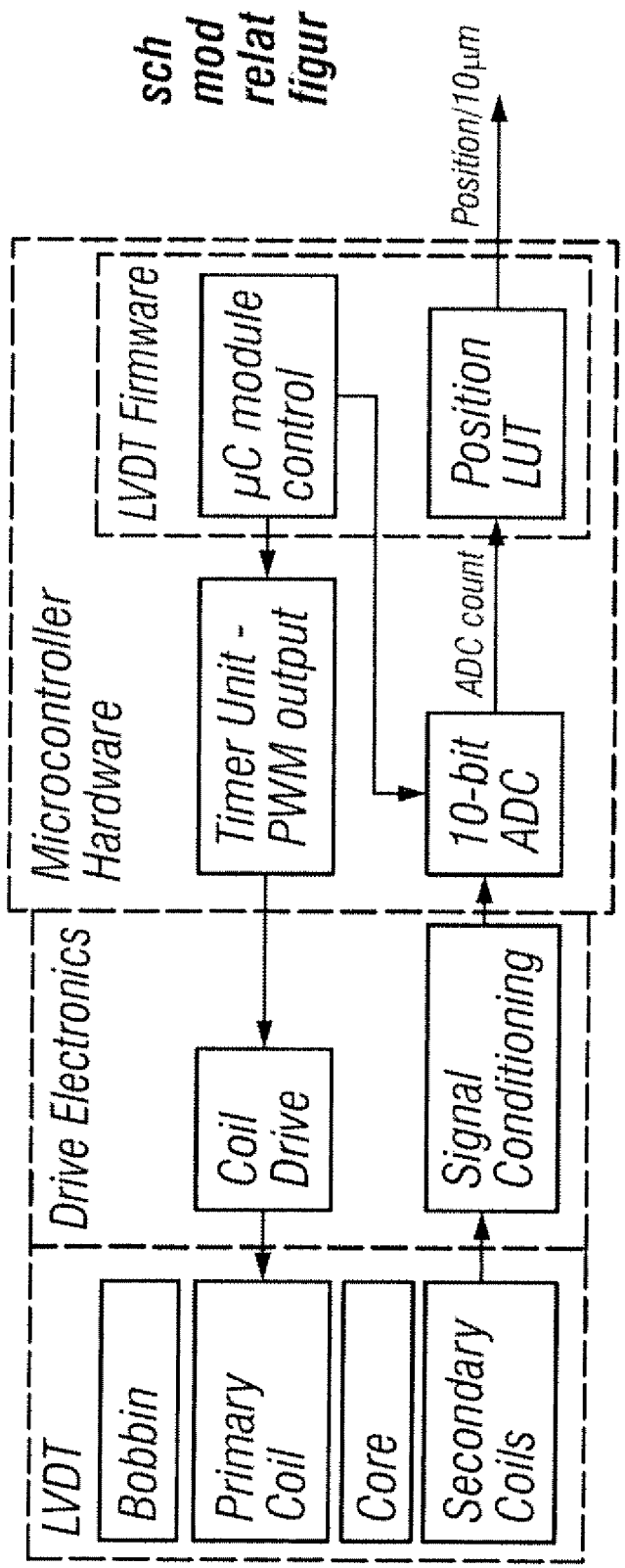
FIGS. 47-53 show various graphs of penetrating member performance and control schematics.

In one embodiment of the present invention, an LVDT position sensor module will now be described. As a nonlimiting example, the LVDT, incorporating the bobbin 710, primary coil, core and secondary coils. FIGS. 45 and 46 show one embodiment of a bobbin 710 according to the present invention. The bobbin 710 may include a coil separator 712. Secondary coils may be wound over regions 714 and 716. The hub portion 718 may be removed after manufacturing to further decrease the size of the bobbin 710. The diameter of the bobbin 710 may be varied. The length is determined by the through distance and a slight variance for magnetic effects. In one embodiment, the coils are 0.6 mm wire. The layers determines the number of coils. The fewer turns used, the less field you get. The present embodiment may have four layers for the secondary and two for the primary coil. It should be understood that other combinations of layers such as two and one may also be used. It is seen that a physical wall 712 is used to separate the coils (not shown). This provides for simplified manufacturing. The coils may be wound in a uniform manner, in one embodiment. A processor may be used to interpolate the nonlinear output from the coils. Each processor may be calibrated to the output to linearize it. In further embodiments, a wall 712 may be removable after the coils are wound. In still further embodiments, a clamp may be placed on the bobbin during winding and may be removed after the coils are wound.

The entire system may also include coil drive electronics, signal conditioning and microcontroller hardware, and firmware to control the microcontroller modules and process the incoming signal.

One reason for considering the LVDT as a position sensor is because of its advantages over an optical encoder. These break down into advantages for the product (the potential for lower cost manufacture and improved packaging), as well as functional advantages for the control system: (high speed, high accuracy on-demand position measurement).

Desired Features

To replace a linear encoder as a position and speed sensor, the LVDT module desire to have at least one of the following: Size—as small as possible; stability—the encoder module is stable with temperature, so the LVDT should be too; range/resolution—20 m across the measurement range of 8 mm; response time/update frequency—5 s/200 kHz; and/or moving mass—as low as possible, to limit the effect on carriage ballistics.

Referring now to FIG. 46, a generic system schematic showing the modules and their relationships is shown. In one embodiment, for its operation, the module relies in part on the timing relationship between the signal which is used to drive the LVDT primary coil, sourced in this embodiment from a PWM module, and the sampling time of a 10-bit ADC. As a nonlimiting example, these may both be integral blocks on board a 16-bit microcontroller. These blocks operate in synchronism, which reduces the need for external componentry. The phase delay is set by internal microcontroller settings and by parameters of the external circuit. ADC sampling time is synchronized with the input signal in the present embodiment.

Figure 48:
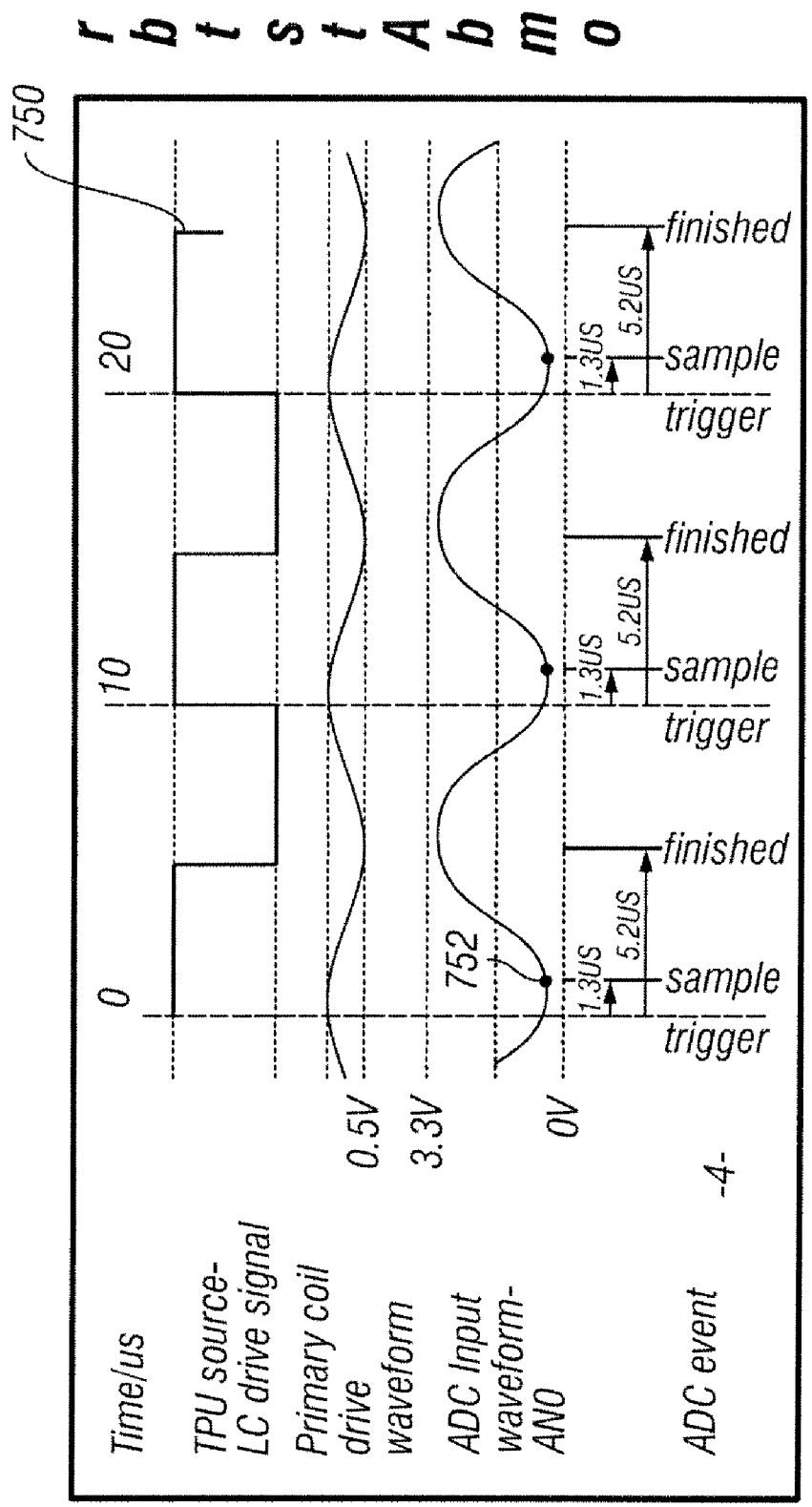
Figure 49:
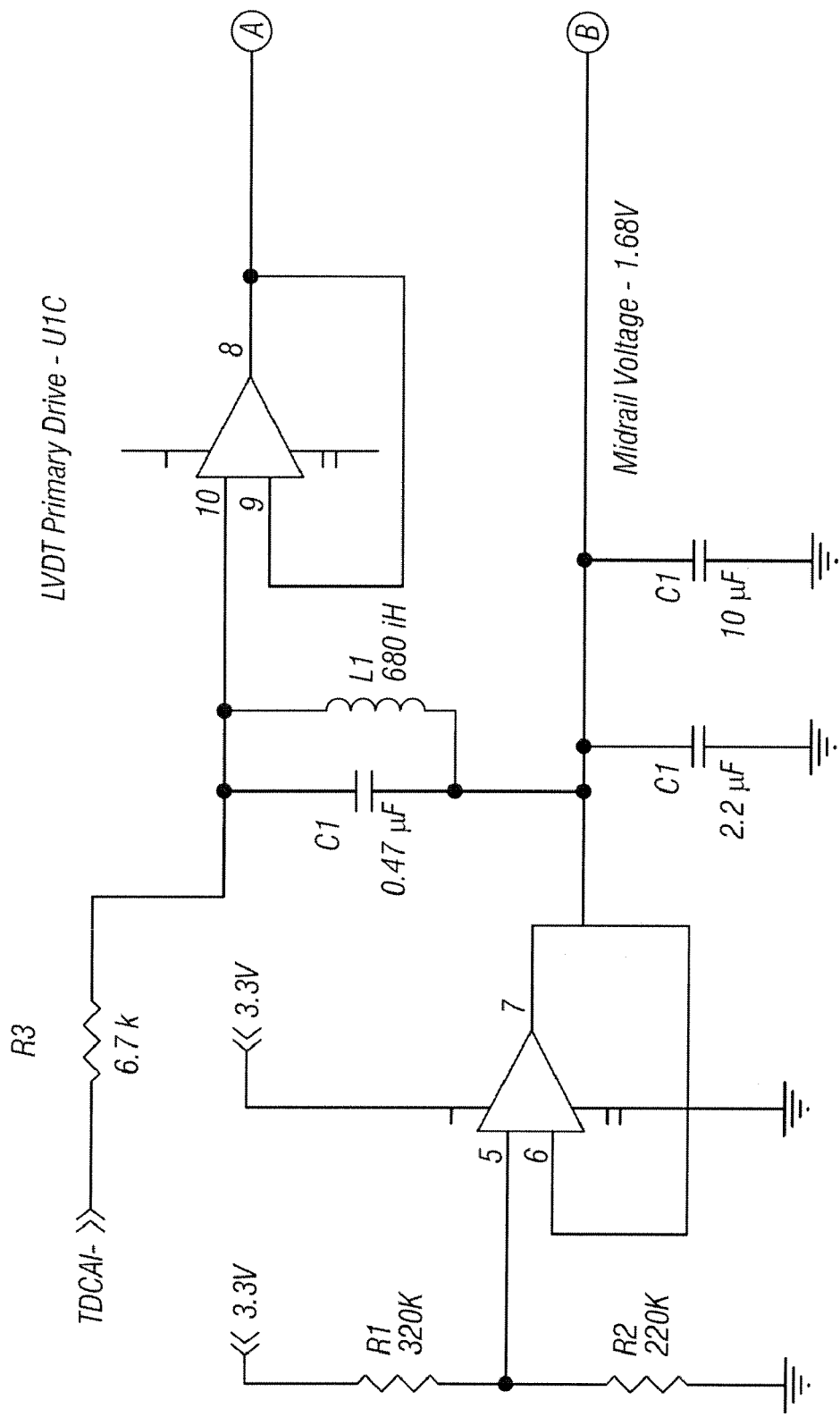
Figure 49:
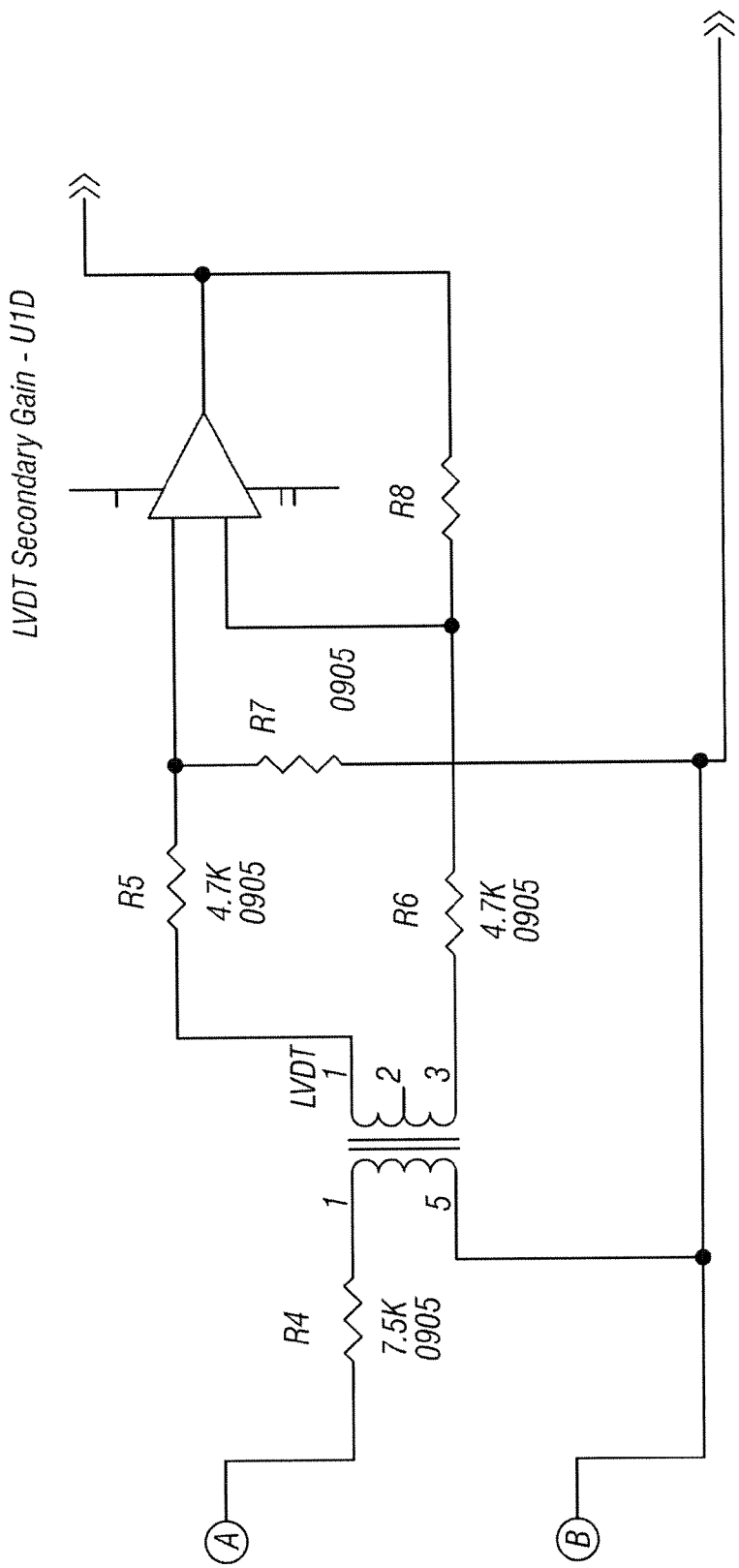

FIG. 48 shows the timing of the signals of interest. FIG. 49 shows one embodiment of the drive electronics which implement the coil drive and signal conditioning. During initial testing, a working frequency for the primary drive circuit was chosen in one embodiment which enables the ADC to make one sample for every cycle of the LVDT drive signal. By the adjustment of the phase delay, the ADC can be made to sample at the peak of the secondary coil cycle, thereby making the best use of the available positional resolution. As seen in FIG. 48, the system may use a square wave input 750. A resonant circuit may be used to convert this square wave into a sinusoidal waveform to drive the primary coil. In this embodiment, sampling by the ADC is related to the square wave input 750. It should be understood that a sine wave generator may also be used in some embodiments. A certain delay may be used so that the sampling occurs a the optimal point 752 (as seen in FIG. 48).

By synchronizing the timing of the ADC samples to the drive signal and by using the internal sample and hold circuit, the design of this embodiment avoids the need to include external rectification or hold circuitry.

LVDT Primary Coil Drive

The LVDT desires a sine wave to drive the primary coil: this is achieved by exciting a parallel resonant LC circuit with a square wave input (TIOCA1-Vdrive signal). This is then amplified (U1C) to create a lower impedance source for the primary coil. The LC circuit is adjusted to resonate at the module operating frequency and R3 is used to limit the output amplitude. R4 compensates for the primary coil DC impedance to prevent output clipping on U1C.

Coupling and Secondary Coil Signal Conditioning

The voltage ratio of the LVDT is a function of the turns ratio and the geometry of the coils. This is chosen, alongside all the gains in the signal path, to preserve SNR. The secondary coil voltage is fed through a standard high gain differential amplifier (U1D) before being fed into the ADC. The choice of resistor values for U1D is driven by the need to obtain maximum gain without loading the LVDT secondary coil or the op-amp excessively. The entire LVDT drive circuit is referenced to a stabilised mid-rail voltage to use the op-amps most effectively.

ADC Conversion and Signal Processing

Figure 50:
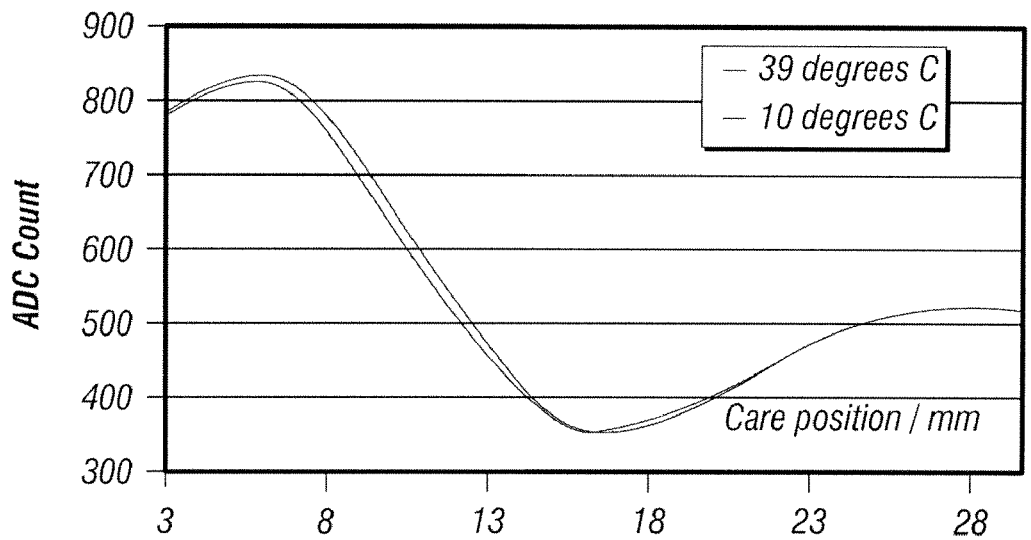

The timing of the ADC sampling and conversion process is shown at the bottom of FIG. 4. The ADC is triggered by the TPU, which also supplies the PWM signal. It samples near the peak of the negative going half-cycle. The ADC voltage reference pin, Vref, is set-up so that the ADC gives its full 10-bit resolution over the anticipated voltage swing of the amplified LVDT secondary signal at the sampling time. With the LVDT optimally set up, this the whole PSU rail voltage. The output from the ADC as the LVDT core was moved over its travel can be seen in FIG. 50. A look-up table of 13 calibration values was used to encode the ADC counts over a range from 7.50 to 14.00 mm. The sampling of the ADC may be increased from 10 ms to 7 ms (40 kHz) depending on the microcontroller used.

Module Components

Drive Electronics—Op-Amp Circuit

In one embodiment, the rail-to-rail op-amp chosen for the prototype circuit was the National LM824. From the table below, it was chosen because it is a low cost device, it has a 3.3V capability, a respectable gin-bandwidth product of 5 MHz acceptable input offset voltage and output drive capability, whilst offering 4 channels of gain.

In the three instances in which it is used, there are differing requirements. In each one current drive capability and gain bandwidth product are the most important

Mid-Rail Supply—U1B, Coil Drive—U1C

In both these instances, the closed loop gain is 1, so the greatest requirement is for output drive capability. When testing the LVDT #0, the 75R resistor was necessary to prevent output clipping. With Ts #1-#4, this was reduced to 27R.

Secondary Gain—U1D

The op-amp was set-up to give a closed-loop gain of 1 at 100 kHz which is well within its gain—bandwidth capability. This op-amp will cope with 200 kHz testing, and it may be possible to specify an op-amp with a lower GBW product, and reduce cost further.

Microcontroller Hardware—ADC/TPU

The LVDT circuit was prototyped on a Hitachi H8S2318, running at 20 MHz. The operating frequency of the circuit was 100 kHz. One of the limiting factors on this is the ADC conversion time, which was measured at 5.8 s. This conversion rate is slower than the Adc on the proposed H8S3694 microcontroller, which is specified at 3.5 s.

Module Performance

In one embodiment, two designs of LVDT were tested. LVDT #0 was a simple design with three similar coils adjacent to each other. LVDTs #1 to #4 were made to the design shown in FIGS. 45 and 46, with a primary coil running the whole length of the coil and 2 secondary coils overwound on each half-section.

Repeatability

Between Calibrations

In this embodiment, the calibration curve of LVDT #0 was measured on three occasions. Across the whole calibration range of 27 mm, the maximum deviation from the mean reading was +/−3 counts (0.79%) and the standard deviation of 1.12 counts (0.29%).

Between Coils

Three identical examples of the same design, LVDTs #1, #2, #3 were constructed and calibrated. The results of the calibration curves are shown in FIGS. 8 and 9 below. Across the whole calibration range, the overall standard deviation between readings of the three coils was 5.82 counts (1.10% of range). This equates to a maximum positional error of 0.30 mm when the reading is calibrated in mm.

Since the mechanical system provides a known starting reference, all measurements are relative to the zero point. This error should not affect the penetrating member positional accuracy.

Temperature Stability

The sensitivity of the LVDT and its drive electronics to temperature variation was measured across the usable temperature range, by both heating and cooling the prototype assembly and performing a calibration. The results are displayed in FIGS. 50 and 51. FIGS. 48 and 49: LVDT #2 Combined calibration chart—hot and cold readings, positional errors in across temperature range across usable position range In one embodiment, the maximum error in ADC count measured over the temperature range would equate to an error of 0.9 mm in the worst case. The maximum positional error within the usable range was 0.48 mm. This level of error requires further attention to reduce it because this error will be evident in the course of the normal use of the product. It is thought that this is caused by changes in the resistance of the LVDT coil; temperature-resistance changes within the op-amps and the ancillary resistors, and especially the primary drive circuit.

Resolution

The resolution of the LVDT module depends on two factors:

The ADC Resolution

The rate of change of output amplitude of the secondary coil with respect to the core position: the higher the better.

Figure 51:
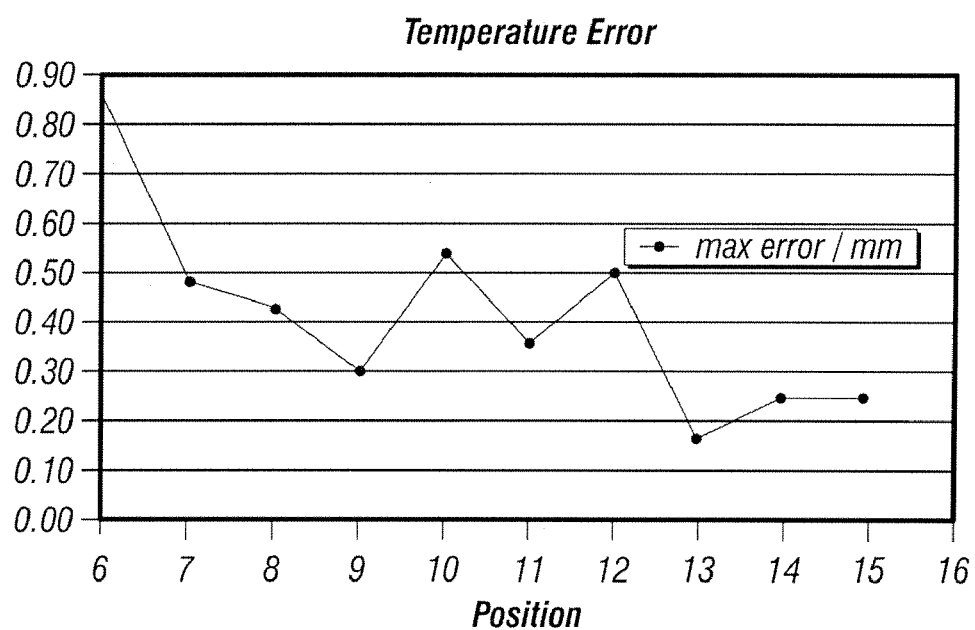
Figure 52:
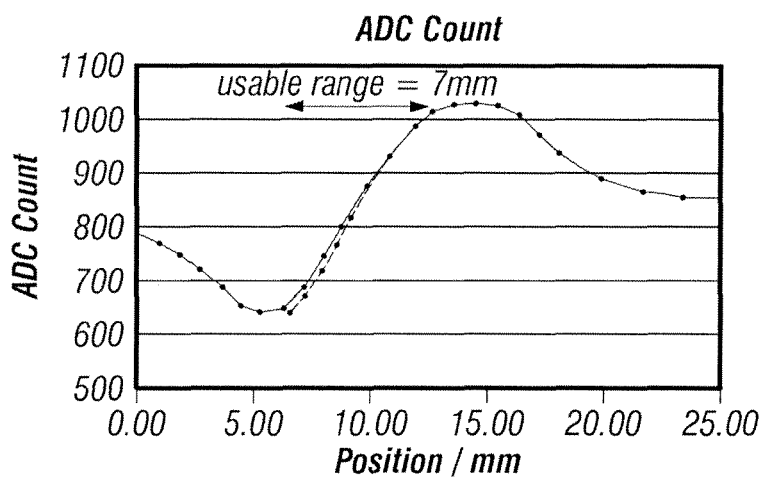
Figure 53:
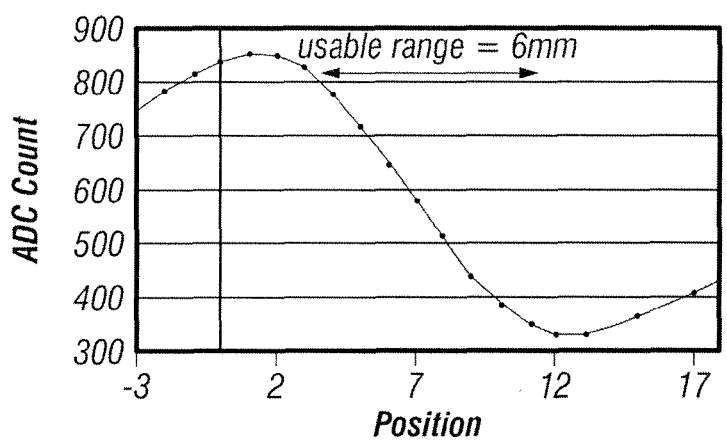

For this embodiment, the ADC resolution was fixed at 10-bits. Within the range provided by this, the resolution was limited by the maximum signal amplitude which could be achieved from the secondary coil amplifier. Calibration curves for the first prototype LVDT, #0, and for #1-#3 are shown in FIGS. 51 and 52 below. The usable range of the LVDT is highlighted on each figure. For LVDT 0, FIG. 7 shows that the raw ADC count changes rapidly with position between 7 and 14 mm offset and this is the region where the resolution was highest on this LVDT prototype. Over this range, the resolution varied between 0.025 mm and 0.014 mm. FIGS. 52 and 53: Calibration charts—LVDT #0, and LVDTs #1-#3 (combined)

To check the effect of counterwinding, one of the secondary coils was wound in the opposite sense to all the other coils. As expected, the effect was the same as that of switching coil polarity, with no change in the amplitude/position relationship.

Physical Dimensions

Figure 54:
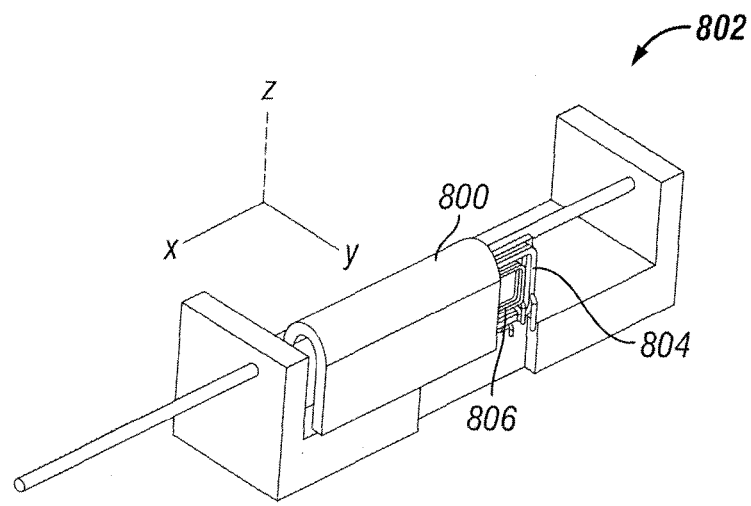
FIGS. 54-56 shows various embodiments of penetrating member drivers.
Figure 55:
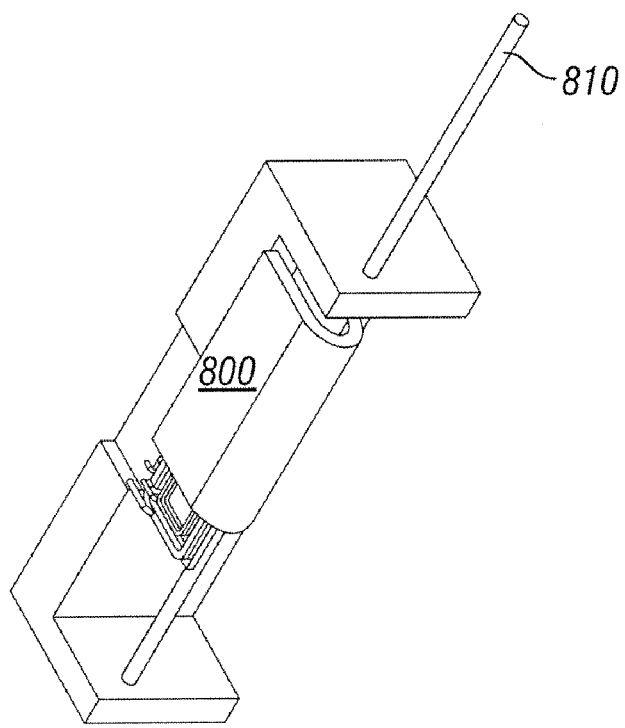

For one embodiment, Some 2D sketches of the LVDT bobbin are shown in FIGS. 54 and 55. The overall length is governed by the throw distance and the diameter is governed by the minimum achievable wall thicknesses and the number of turns wound. The representative outer dimensions OD for this iteration were OD 3.65 mm, length 23 mm. This would create a packaged volume of approximately 340 mm3. For the encoder, the volume to be packaged is approximately 1100 mm3. In a future design iteration, the number of turns wound could be reduced by approximately 25% before any detrimental effects were noticed which would further benefit packaging.

Effect of Core Size

In one embodiment, a calibration was attempted using an 8 mm core, and the result was that the level of coupling was decreased but the overall range between secondary peaks was unaffected. This suggests that reducing the core length will have no beneficial effect in increasing the usable throw distance. It is estimated that this can be reduced by at least 50% in further trials. In one embodiment, the following

| Parameter | LVDT module |
| --- | --- |
| Stability | Coil-to-coil repeatability: 0.30 mm<br>Temperature: 0.50 mm over operating temp range and usable calibration range |
| Range/Resolution | 8 mm/20 μm |
| Response time | On-demand. 200 kHz/5 μs with 3694 microcontroller. Tested at 100 kHz/10 μs |
| Moving mass | 0.163 g |
| Size | 340 mm$^3$ |

| Coils | Parameter | Value |
| --- | --- | --- |
| #0 | Turns ratio - (primary/secondary A, secondary B) | 1:1:1 |
| | Primary resistance | 1.1 ohm |
| | Resolution | 20 μm |
| | Secondary resistance | 2.1 ohm |
| | Repeatability | 0.29% |
| | Range | 7 mm |
| #1-#3 | Turns ratio - (primary/secondary A, secondary B) | 1:1:1 |
| | Primary resistance | 32 ohm |
| | Secondary resistance | 34.5/34.5 ohm |
| | Repeatability between coils | 1.10% |
| | Resolution | 20 μm |
| | Range at this resolution | 7 mm |

In yet another embodiment, a solenoid-based actuator has been developed to move penetrating members into skin for the purpose of collecting blood for the analysis of blood glucose. To reduce pain and improve blood yield, the speed, acceleration, and position of the actuating solenoid is controlled. In this embodiment, control is provided by a processor that monitors the actuation cycle and modulates the electrical power to the solenoid. Commercially available position transducers (such as Hewlett Packard HEDS9731) are being used to provide actuator position information.

In one embodiment, the present invention consists of a Linear Variable Differential Position Transducer (LVDT) that has been modified to provide a low profile design. LVDT's are commonly available such as from Solartron (704) 868-4661 and consist of adjacent cylindrically wound coils with a soft iron coupling slug that moves inside the coils. Energy from an excitation coil is coupled into two secondary coils in proportion to the slug position within the coils. Available LVDT's are cylindrical so the height and width are equal.

Referring now to FIG. 10, to create a more compact LVDT, in one embodiment, the excitation and driven coils could be wound as flat coils and placed next to each other in a plane. The moving slug 100 would then take the form of a flat plate of soft iron that moves in a plane parallel to the coil plane, and close to it. The resulting transducer 102 would be thin relative to its width and would make more efficient use of space. The price for a more compact design would be efficiency of coupling, and possibly accuracy.

Figure 56:
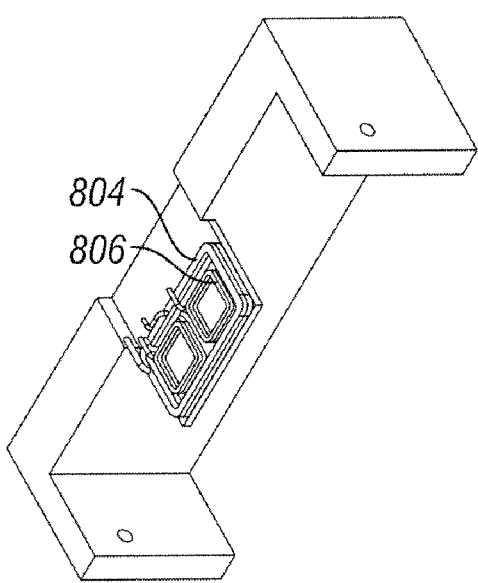

One arrangement of coils, as illustrated in FIG. 54, would consist of a large rectangular driving coil wound in a flat open shape. Inside the driver coil 104, two smaller rectangular or square coils 106 would be mounted side-by-side. The slug would move along the long axis of the driving coil. FIGS. 55 and 56 provide views of the coil. Specifically, FIG. 56 shows the slug removed and the coils 104 and 106 exposed.

Another arrangement of coils would be similar, with sensing coils inside a driving coil, but the coils may be traces etched onto a thin PCB or flex circuit. Multiple PCB's and/or flex circuits could be stacked to provide more coil turns.

An alternate arrangement of the slug would consist of a soft iron plate of sheet metal, formed into a "U" so as to enclose the coils on three sides. This wrap-around slug would provide better coupling between the coils at the cost of more moving mass.

Figure 57:
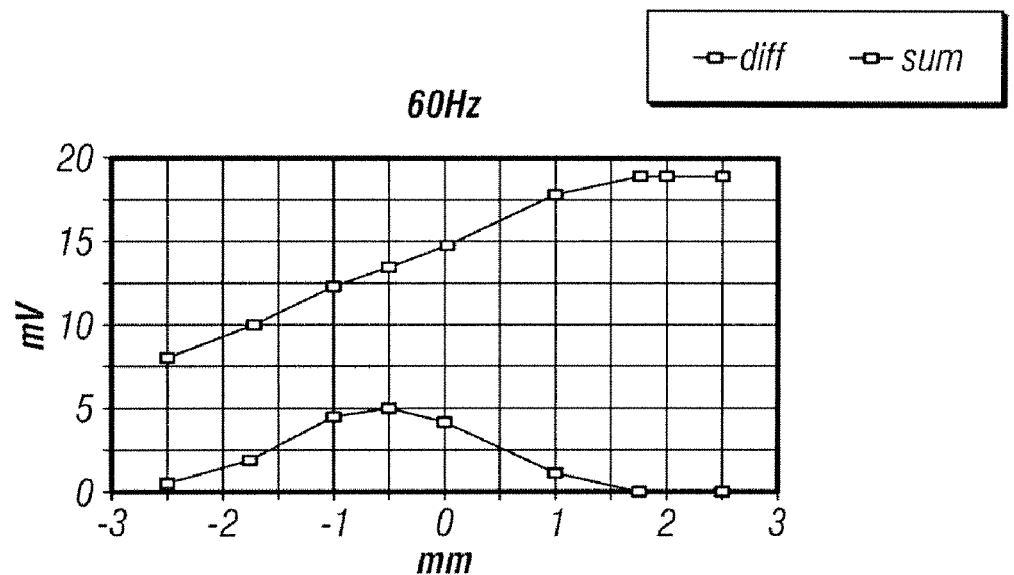
FIGS. 57 and 58 show graph of performance.

In this embodiment, the primary coil was supplied with 13 Amp turns. The secondary coils have 640 turns each. The emf induced in each secondary coil was determined at various positions of the c-slug, from fully covering the 2 coils to fully uncovering them. FIG. 57 below shows the differential between the 2 coils emf and their sum also. The values were obtained at 60 Hz in the primary coil. The sensitivity appears to be about 3 mV/mm, in the linear section of the sum curve.

Figure 58:
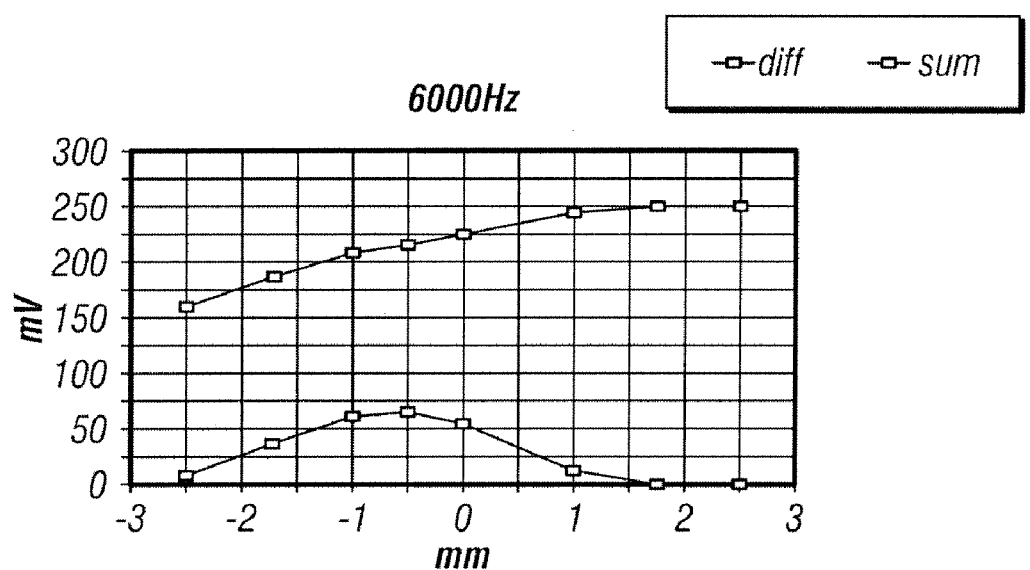

FIG. 58 below is similar to the one above but the values were obtained at 6,000 Hz in the primary coil. The sensitivity appears to have increased to 22 mV/mm, in the linear section.

In one embodiment, the linear section of the travel appears to be about 3.5 mm. This can be increased to 8 mm by doubling the width of the secondary coils to 4 mm each. The number of turns of these secondary coils is determined by the packing factor and the fineness of the wire used. The number of turns and current in the primary coil can be chosen for the most appropriate match with the available supply to produce the necessary amp-turns.

In one embodiment, the C-slug was assigned mild steel for material. The thickness can be reduced significantly since the levels of flux density in the present cross-section are very low. It is probably sufficient to have a steel sheet on one side of the coils only to produce the required linear emf curves. The material of the frame can be either magnetic or non-magnetic, since no effect was seen on the emf values.

In one embodiment, a position transducer for detecting mechanism component position is provided. The transducer functions by winding flat coils and placing driver and driven coils inside each other; coupling coils with a moving flat soft iron plate or forming the moving soft iron plate so it encloses the coils on three or more sides. The coils may be created by etching a PCB or flex circuit. A position transducer is described that works on the LVDT principle and is very compact. The low-profile form of the transducer is achieved by using flat, coplanar coils and a flat coupling slug.

In one embodiment, the shaft 110 may be covered with a magnetic layer. Plating of magnetic material on the carbon fiber rod would reduce the mass of the slug. Moving mass reduction will allow for improved acceleration.

Figure 59:
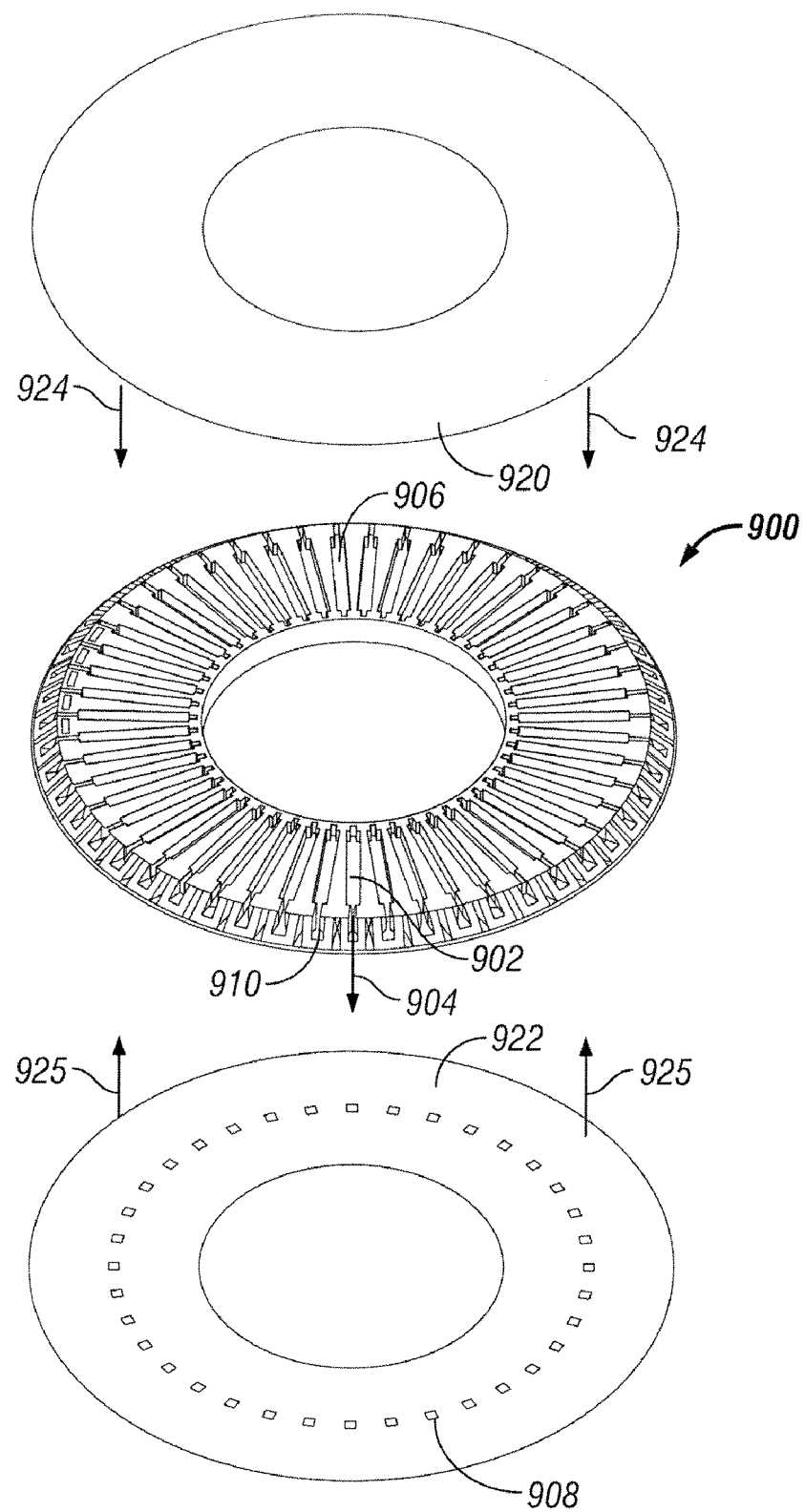
FIG. 59 shows one embodiment of disc for use with the present invention.

Referring now to FIG. 59, a still further embodiment of a cartridge according to the present invention will be described. FIG. 59 shows one embodiment of a cartridge 900 which may be removably inserted into an apparatus for driving penetrating members to pierce skin or tissue. The cartridge 900 has a plurality of penetrating members 902 that may be individually or otherwise selectively actuated so that the penetrating members 902 may extend outward from the cartridge, as indicated by arrow 904, to penetrate tissue. In the present embodiment, the cartridge 900 may be based on a flat disc with a number of penetrating members such as, but in no way limited to, (25, 50, 75, 100, . . . ) arranged radially on the disc or cartridge 800. It should be understood that although the cartridge 900 is shown as a disc or a disc-shaped housing, other shapes or configurations of the cartridge may also work without departing from the spirit of the present invention of placing a plurality of penetrating members to be engaged, singly or in some combination, by a penetrating member driver.

Each penetrating member 902 may be contained in a cavity 906 in the cartridge 900 with the penetrating member's sharpened end facing radially outward and may be in the same plane as that of the cartridge. The cavity 906 may be molded, pressed, forged, or otherwise formed in the cartridge. Although not limited in this manner, the ends of the cavities 906 may be divided into individual fingers (such as one for each cavity) on the outer periphery of the disc. The particular shape of each cavity 906 may be designed to suit the size or shape of the penetrating member therein or the amount of space desired for placement of the analyte detecting members 808. For example and not limitation, the cavity 906 may have a V-shaped cross-section, a U-shaped cross-section, C-shaped cross-section, a multi-level cross section or the other cross-sections. The opening 810 through which a penetrating member 902 may exit to penetrate tissue may also have a variety of shapes, such as but not limited to, a circular opening, a square or rectangular opening, a U-shaped opening, a narrow opening that only allows the penetrating member to pass, an opening with more clearance on the sides, a slit, a configuration as shown in FIG. 75, or the other shapes.

In this embodiment, after actuation, the penetrating member 902 is returned into the cartridge and may be held within the cartridge 900 in a manner so that it is not able to be used again. By way of example and not limitation, a used penetrating member may be returned into the cartridge and held by the launcher in position until the next lancing event. At the time of the next lancing, the launcher may disengage the used penetrating member with the cartridge 900 turned or indexed to the next clean penetrating member such that the cavity holding the used penetrating member is position so that it is not accessible to the user (i.e. turn away from a penetrating member exit opening). In some embodiments, the tip of a used penetrating member may be driven into a protective stop that hold the penetrating member in place after use. The cartridge 900 is replaceable with a new cartridge 900 once all the penetrating members have been used or at such other time or condition as deemed desirable by the user.

Referring still to the embodiment in FIG. 59, the cartridge 900 may provide sterile environments for penetrating members via seals, foils, covers, polymeric, or similar materials used to seal the cavities and provide enclosed areas for the penetrating members to rest in. In the present embodiment, a foil or seal layer 920 is applied to one surface of the cartridge 900. The seal layer 920 may be made of a variety of materials such as a metallic foil or other seal materials and may be of a tensile strength and other quality that may provide a sealed, sterile environment until the seal layer 920 is penetrate by a suitable or penetrating device providing a preselected or selected amount of force to open the sealed, sterile environment. Each cavity 906 may be individually sealed with a layer 920 in a manner such that the opening of one cavity does not interfere with the sterility in an adjacent or other cavity in the cartridge 800. As seen in the embodiment of FIG. 59, the seal layer 920 may be a planar material that is adhered to a top surface of the cartridge 800.

Depending on the orientation of the cartridge 900 in the penetrating member driver apparatus, the seal layer 920 may be on the top surface, side surface, bottom surface, or other positioned surface. For ease of illustration and discussion of the embodiment of FIG. 59, the layer 920 is placed on a top surface of the cartridge 800. The cavities 906 holding the penetrating members 902 are sealed on by the foil layer 920 and thus create the sterile environments for the penetrating members. The foil layer 920 may seal a plurality of cavities 906 or only a select number of cavities as desired.

In a still further feature of FIG. 59, the cartridge 900 may optionally include a plurality of analyte detecting members 908 on a substrate 922 which may be attached to a bottom surface of the cartridge 900. The substrate may be made of a material such as, but not limited to, a polymer, a foil, or other material suitable for attaching to a cartridge and holding the analyte detecting members 908. As seen in FIG. 59, the substrate 922 may hold a plurality of analyte detecting members, such as but not limited to, about 10-50, 50-100, or other combinations of analyte detecting members. This facilitates the assembly and integration of analyte detecting members 908 with cartridge 900. These analyte detecting members 908 may enable an integrated body fluid sampling system where the penetrating members 902 create a wound tract in a target tissue, which expresses body fluid that flows into the cartridge for analyte detection by at least one of the analyte detecting members 908. The substrate 922 may contain any number of analyte detecting members 908 suitable for detecting analytes in cartridge having a plurality of cavities 906. In one embodiment, many analyte detecting members 908 may be printed onto a single substrate 922 which is then adhered to the cartridge to facilitate manufacturing and simplify assembly. The analyte detecting members 908 may be electrochemical in nature. The analyte detecting members 908 may further contain enzymes, dyes, or other detectors which react when exposed to the desired analyte. Additionally, the analyte detecting members 908 may comprise of clear optical windows that allow light to pass into the body fluid for analyte analysis. The number, location, and type of analyte detecting member 908 may be varied as desired, based in part on the design of the cartridge, number of analytes to be measured, the need for analyte detecting member calibration, and the sensitivity of the analyte detecting members. If the cartridge 900 uses an analyte detecting member arrangement where the analyte detecting members are on a substrate attached to the bottom of the cartridge, there may be through holes (as shown in FIG. 76), wicking elements, capillary tube or other devices on the cartridge 900 to allow body fluid to flow from the cartridge to the analyte detecting members 908 for analysis. In other configurations, the analyte detecting members 908 may be printed, formed, or otherwise located directly in the cavities housing the penetrating members 902 or areas on the cartridge surface that receive blood after lancing.

The use of the seal layer 920 and substrate or analyte detecting member layer 822 may facilitate the manufacture of these cartridges 10. For example, a single seal layer 920 may be adhered, attached, or otherwise coupled to the cartridge 900 as indicated by arrows 924 to seal many of the cavities 906 at one time. A sheet 922 of analyte detecting members may also be adhered, attached, or otherwise coupled to the cartridge 900 as indicated by arrows 925 to provide many analyte detecting members on the cartridge at one time. During manufacturing of one embodiment of the present invention, the Cartridge 900 may be loaded with penetrating members 902, sealed with layer 920 and a temporary layer (not shown) on the bottom where substrate 922 would later go, to provide a sealed environment for the penetrating members. This assembly with the temporary bottom layer is then taken to be sterilized. After sterilization, the assembly is taken to a clean room (or it may already be in a clear room or equivalent environment) where the temporary bottom layer is removed and the substrate 922 with analyte detecting members is coupled to the cartridge as shown in FIG. 59. This process allows for the sterile assembly of the cartridge with the penetrating members 902 using processes and/or temperatures that may degrade the accuracy or functionality of the analyte detecting members on substrate 922. As a nonlimiting example, the entire cartridge 900 may then be placed in a further sealed container such as a pouch, bag, plastic molded container, etc. . . . to facilitate contact, improve ruggedness, and/or allow for easier handling.

In some embodiments, more than one seal layer 920 may be used to seal the cavities 906. As examples of some embodiments, multiple layers may be placed over each cavity 906, half or some selected portion of the cavities may be sealed with one layer with the other half or selected portion of the cavities sealed with another sheet or layer, different shaped cavities may use different seal layer, or the like. The seal layer 920 may have different physical properties, such as those covering the penetrating members 902 near the end of the cartridge may have a different color such as red to indicate to the user (if visually inspectable) that the user is down to say 10, 5, or other number of penetrating members before the cartridge should be changed out.

Figure 60:
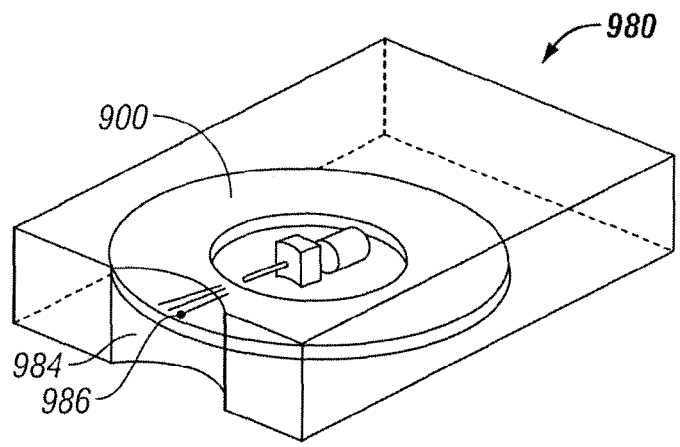
FIG. 60 shows one view of the disc in a penetrating member device.

Referring now to FIG. 60, one embodiment of an apparatus 980 using a radial cartridge 900 with a penetrating member driver 982 is shown. A contoured surface 884 is located near a penetrating member exit port 986, allowing for a patient to place their finger in position for lancing. Although not shown, the apparatus 980 may include a human readable or other type of visual display to relay status to the user. The display may also show measured analyte levels or other measurement or feedback to the user without the need to plug apparatus 980 or a separate test strip into a separate analyte reader device. The apparatus 980 may include a processor or other logic for actuating the penetrating member or for measuring the analyte levels. The cartridge 900 may be loaded into the apparatus 980 by opening a top housing of the apparatus which may be hinged or removably coupled to a bottom housing. The cartridge 900 may also drawn into the apparatus 980 using a loading mechanism similar in spirit to that found on a compact disc player or the like. In such an embodiment, the apparatus may have a slot (similar to a CD player in an automobile) that allows for the insertion of the cartridge 900 into the apparatus 980 which is then automatically loaded into position or otherwise seated in the apparatus for operation therein. The loading mechanism may be mechanically powered or electrically powered. In some embodiments, the loading mechanism may use a loading tray in addition to the slot. The slot may be placed higher on the housing so that the cartridge 900 will have enough clearance to be loaded into the device and then dropped down over the penetrating member driver 982. The cartridge 900 may have an indicator mark or indexing device that allows the cartridge to be properly aligned by the loading mechanism or an aligning mechanism once the cartridge 900 is placed into the apparatus 980. The cartridge 900 may rest on a radial platform that rotates about the penetrating member driver 982, thus providing a method for advancing the cartridge to bring unused penetrating members to engagement with the penetrating member driver. The cartridge 800 on its underside or other surface, may shaped or contoured such as with notches, grooves, tractor holes, optical markers, or the like to facilitate handling and/or indexing of the cartridge. These shapes or surfaces may also be varied so as to indicate that the cartridge is almost out of unused penetrating members, that there are only five penetrating members left, or some other cartridge status indicator as desired.

A suitable method and apparatus for loading penetrating members has been described previously in commonly assigned, copending U.S. patent application Ser. Nos. 10/237,261 & 10/237,262, and are included here by reference for all purposes. Suitable devices for engaging the penetrating members and for removing protective materials associated with the penetrating member cavity are described in commonly assigned, copending U.S. patent application Ser. Nos. 60/422,988 and 60/424,429, and are included here by reference for all purposes. For example in the embodiment of FIG. 59, the foil or seal layer 920 may cover the cavity by extending across the cavity along a top surface 990 and down along the angled surface 892 to provide a sealed, sterile environment for the penetrating member and sensors therein. A piercing element described in U.S. patent application Ser. No. 60/424,429 has a piercing element and then a shaped portion behind the element which pushes the foil to the sides of the cavity or other position so that the penetrating member 902 may be actuated and body fluid may flow into the cavity.

Figure 61:
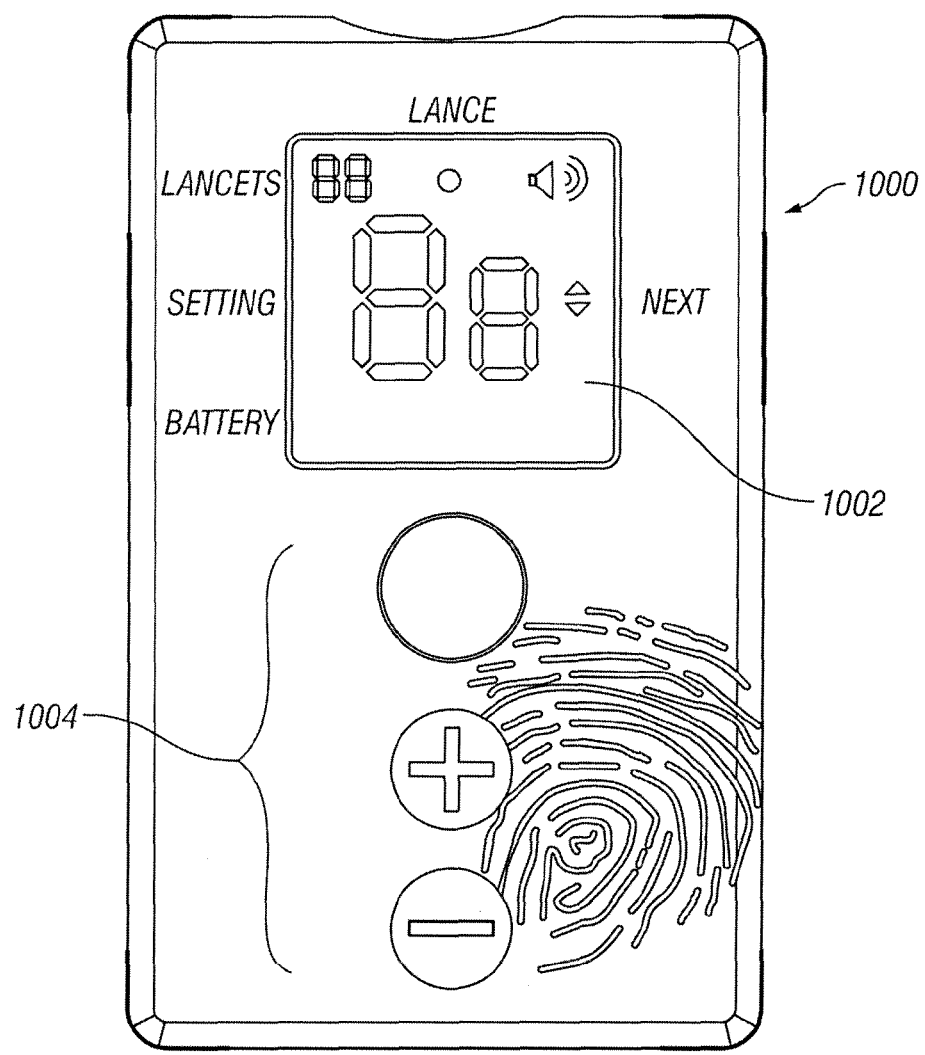
FIG. 61 shows another embodiment of a device that may use a disc as described in FIG. 59.

Referring now to FIG. 61, one embodiment of a device that may use a disc 900 is shown. This embodiment of device 1000 include a display 1002 that shows lancing performance and setting such as penetration depth setting the like. Various buttons 1004 may also be placed on the housing to adjust settings and/or to activate lancing.

It should be understood that device 1000 may include a processor for implementing any of the control methodologies set forth herein. The processor may control the penetrating member driver and/or active braking device such a pads, stops, dampers, dashpots and other mechanism to control penetrating member speed. The characteristic phases of penetrating member advancement and retraction can be plotted on a graph of force versus time illustrating the force exerted by the penetrating member driver on the penetrating member to achieve the desired displacement and velocity profile. The characteristic phases are the penetrating member introduction phase A-C where the penetrating member is longitudinally advanced into the skin, the penetrating member rest phase D where the penetrating member terminates its longitudinal movement reaching its maximum depth and becoming relatively stationary, and the penetrating member retraction phase E-G where the penetrating member is longitudinally retracted out of the skin. The duration of the penetrating member retraction phase E-G is longer than the duration of the penetrating member introduction phase A-C, which in turn is longer than the duration of the penetrating member rest phase D.

The introduction phase further comprises a penetrating member launch phase prior to A when the penetrating member is longitudinally moving through air toward the skin, a tissue contact phase at the beginning of A when the distal end of the penetrating member makes initial contact with the skin, a tissue deformation phase A when the skin bends depending on its elastic properties which are related to hydration and thickness, a tissue lancing phase which comprises when the penetrating member hits the inflection point on the skin and begins to cut the skin B and the penetrating member continues cutting the skin C. The penetrating member rest phase D is the limit of the penetration of the penetrating member into the skin. Pain is reduced by minimizing the duration of the penetrating member introduction phase A-C so that there is a fast incision to a certain penetration depth regardless of the duration of the deformation phase A and inflection point cutting B which will vary from user to user. Success rate is increased by measuring the exact depth of penetration from inflection point B to the limit of penetration in the penetrating member rest phase D. This measurement allows the penetrating member to always, or at least reliably, hit the capillary beds which are a known distance underneath the surface of the skin.

The penetrating member retraction phase further comprises a primary retraction phase E when the skin pushes the penetrating member out of the wound tract, a secondary retraction phase F when the penetrating member starts to become dislodged and pulls in the opposite direction of the skin, and penetrating member exit phase G when the penetrating member becomes free of the skin. Primary retraction is the result of exerting a decreasing force to pull the penetrating member out of the skin as the penetrating member pulls away from the finger. Secondary retraction is the result of exerting a force in the opposite direction to dislodge the penetrating member. Control is necessary to keep the wound tract open as blood flows up the wound tract. Blood volume is increased by using a uniform velocity to retract the penetrating member during the penetrating member retraction phase E-G regardless of the force required for the primary retraction phase E or secondary retraction phase F, either of which may vary from user to user depending on the properties of the user's skin.

Displacement versus time profile of a penetrating member for a controlled penetrating member retraction can be plotted. Velocity vs. time profile of the penetrating member for the controlled retraction can also be plotted. The penetrating member driver controls penetrating member displacement and velocity at several steps in the lancing cycle, including when the penetrating member cuts the blood vessels to allow blood to pool 2130, and as the penetrating member retracts, regulating the retraction rate to allow the blood to flood the wound tract while keeping the wound flap from sealing the channel 2132 to permit blood to exit the wound.

The tenting process and retrograde motion of the penetrating member during the lancing cycle can be illustrated graphically which shows both a velocity versus time graph and a position versus time graph of a penetrating member tip during a lancing cycle that includes elastic and inelastic tenting. From point 0 to point A, the penetrating member is being accelerated from the initialization position or zero position. From point A to point B, the penetrating member is in ballistic or coasting mode, with no additional power being delivered. At point B, the penetrating member tip contacts the tissue and begins to tent the skin until it reaches a displacement C. As the penetrating member tip approaches maximum displacement, braking force is applied to the penetrating member until the penetrating member comes to a stop at point D. The penetrating member then recoils in a retrograde direction during the settling phase of the lancing cycle indicated between D and E. Note that the magnitude of inelastic tenting indicated in FIG. 61 is exaggerated for purposes of illustration.

The amount of inelastic tenting indicated by Z tends to be fairly consistent and small compared to the magnitude of the elastic tenting. Generally, the amount of inelastic tenting Z can be about 120 to about 140 microns. As the magnitude of the inelastic tenting has a fairly constant value and is small compared to the magnitude of the elastic tenting for most patients and skin types, the value for the total amount of tenting for the penetration stroke of the penetrating member is effectively equal to the rearward displacement of the penetrating member during the settling phase as measured by the processor 193 plus a predetermined value for the inelastic recoil, such as 130 microns. Inelastic recoil for some embodiments can be about 100 to about 200 microns. The ability to measure the magnitude of skin tenting for a patient is important to controlling the depth of penetration of the penetrating member tip as the skin is generally known to vary in elasticity and other parameters due to age, time of day, level of hydration, gender and pathological state.

This value for total tenting for the lancing cycle can then be used to determine the various characteristics of the patient's skin. Once a body of tenting data is obtained for a given patient, this data can be analyzed in order to predict the total penetrating member displacement, from the point of skin contact, necessary for a successful lancing procedure. This enables the tissue penetration device to achieve a high success rate and minimize pain for the user. A rolling average table can be used to collect and store the tenting data for a patient with a pointer to the last entry in the table. When a new entry is input, it can replace the entry at the pointer and the pointer advances to the next value. When an average is desired, all the values are added and the sum divided by the total number of entries by the processor 193. Similar techniques involving exponential decay (multiply by 0.95, add 0.05 times current value, etc.) are also possible.

With regard to tenting of skin generally, some typical values relating to penetration depth are now discussed. A cross sectional view of the layers of the skin can be shown. In order to reliably obtain a useable sample of blood from the skin, it is desirable to have the penetrating member tip reach the venuolar plexus of the skin. The stratum corneum is typically about 0.1 to about 0.6 mm thick and the distance from the top of the dermis to the venuole plexus can be from about 0.3 to about 1.4 mm. Elastic tenting can have a magnitude of up to about 2 mm or so, specifically, about 0.2 to about 2.0 mm, with an average magnitude of about 1 mm. This means that the amount of penetrating member displacement necessary to overcome the tenting can have a magnitude greater than the thickness of skin necessary to penetrate in order to reach the venuolar plexus. The total penetrating member displacement from point of initial skin contact may have an average value of about 1.7 to about 2.1 mm. In some embodiments, penetration depth and maximum penetration depth may be about 0.5 mm to about 5 mm, specifically, about 1 mm to about 3 mm. In some embodiments, a maximum penetration depth of about 0.5 to about 3 mm is useful.

In some embodiments, the penetrating member is withdrawn with less force and a lower speed than the force and speed during the penetration portion of the operation cycle. Withdrawal speed of the penetrating member in some embodiments can be about 0.004 to about 0.5 m/s, specifically, about 0.006 to about 0.01 m/s. In other embodiments, useful withdrawal velocities can be about 0.001 to about 0.02 meters per second, specifically, about 0.001 to about 0.01 meters per second. For embodiments that use a relatively slow withdrawal velocity compared to the penetration velocity, the withdrawal velocity may up to about 0.02 meters per second. For such embodiments, a ratio of the average penetration velocity relative to the average withdrawal velocity can be about 100 to about 1000. In embodiments where a relatively slow withdrawal velocity is not important, a withdrawal velocity of about 2 to about 10 meters per second may be used.

Another example of an embodiment of a velocity profile for a penetrating member can be seen shown, which illustrates a penetrating member profile with a fast entry velocity and a slow withdrawal velocity. A lancing profile showing velocity of the penetrating member versus position. The lancing profile starts at zero time and position and shows acceleration of the penetrating member towards the tissue from the electromagnetic force generated from the electromagnetic driver. At point A, the power is shut off and the penetrating member begins to coast until it reaches the skin indicated by B at which point, the velocity begins to decrease. At point C, the penetrating member has reached maximum displacement and settles momentarily, typically for a time of about 8 milliseconds.

A retrograde withdrawal force is then imposed on the penetrating member by the controllable driver, which is controlled by the processor to maintain a withdrawal velocity of no more than about 0.006 to about 0.01 meters/second. The same cycle is illustrated in the velocity versus time plot of FIG. 151 where the penetrating member is accelerated from the start point to point A. The penetrating member coasts from A to B where the penetrating member tip contacts tissue 233. The penetrating member tip then penetrates the tissue and slows with braking force eventually applied as the maximum penetration depth is approached. The penetrating member is stopped and settling between C and D. At D, the withdrawal phase begins and the penetrating member is slowly withdrawn until it returns to the initialization point shown by E. Note that retrograde recoil from elastic and inelastic tenting was not shown in the lancing profiles for purpose of illustration and clarity.

In another embodiment, the withdrawal phase may use a dual speed profile, with the slow 0.006 to 0.01 meter per second speed used until the penetrating member is withdrawn past the contact point with the tissue, then a faster speed of 0.01 to 1 meters per second may be used to shorten the complete cycle.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. An analyte detecting member to detect the presence of foil may also be included in the lancing apparatus. For example, if a cavity has been used before, the foil or sterility barrier will be punched. The analyte detecting member can detect if the cavity is fresh or not based on the status of the barrier. It should be understood that in optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a lancet becomes unnecessary; manufacturing of multiple penetrating member devices is simplified through the use of cartridges; handling is possible of bare rods metal wires, without any additional structural features, to actuate them into tissue; maintaining extreme (better than 50 micron-lateral- and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. In some embodiments, the penetrating member may be a patent needle. The same driver may be used for advancing and retraction of the penetrating member. Different analyte detecting members detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In some embodiments, the analyte detecting members may formed to flush with the cartridge so that a "well" is not formed. In some other embodiments, the analyte detecting members may formed to be substantially flush (within 200 microns or 100 microns) with the cartridge surfaces. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. Additionally, for some embodiments, any of the cartridge shown above may be configured without any of the penetrating members, so that the cartridge is simply an analyte detecting device. Still further, the indexing of the cartridge may be such that adjacent cavities may not necessarily be used serially or sequentially. As a nonlimiting example, every second cavity may be used sequentially, which means that the cartridge will go through two rotations before every or substantially all of the cavities are used. As another nonlimiting example, a cavity that is 3 cavities away, 4 cavities away, or N cavities away may be the next one used. This may allow for greater separation between cavities containing penetrating members that were just used and a fresh penetrating member to be used next. For any of the embodiments herein, they may be configured to provide the various velocity profiles described.

This application cross-references commonly assigned copending U.S. patent application Ser. No. 10/323,622 filed Dec. 18, 2002; commonly assigned copending U.S. patent application Ser. No. 10/323,623 filed Dec. 18, 2002; and commonly assigned copending U.S. patent application Ser. No. 10/323,624 filed Dec. 18, 2002. This application is also related to commonly assigned copending U.S. patent application Ser. Nos. 10/335,142, 10/335,215, 10/335,258, 10/335,099, 10/335,219, 10/335,052, 10/335,073, 10/335,220, 10/335,252, 10/335,218, 10/335,211, 10/335,257, 10/335,217, 10/335,212, and 10/335,241, 10/335,183, filed Dec. 31, 2002. This application is also a continuation-in-part of commonly assigned, copending U.S. patent application Ser. No. 10/425,815 filed May 30, 2003. This application is a continuation-in-part of commonly assigned, copending U.S. patent application Ser. No. 10/323,622 filed on Dec. 18, 2002, which is a continuation-in-part of commonly assigned, copending U.S. patent application Ser. No. 10/127,395 filed Apr. 19, 2002. This application is also a continuation-in-part of commonly assigned, copending U.S. patent application Ser. No. 10/237,261 filed Sep. 5, 2002. This application is further a continuation-in-part of commonly assigned, copending U.S. patent application Ser. No. 10/420,535 filed Apr. 21, 2003. This application is further a continuation-in-part of commonly assigned, copending U.S. patent application Ser. No. 10/335,142 filed Dec. 31, 2002. This application is further a continuation-in-part of commonly assigned, copending U.S. patent application Ser. No. 10/423,851 filed Apr. 24, 2003. This application also claims the benefit of priority from commonly assigned, copending U.S. Provisional Patent Application Ser. No. 60/422,988 filed Nov. 1, 2002; commonly assigned, copending U.S. Provisional Patent Application Ser. No. 60/424,429 filed Nov. 6, 2002; and commonly assigned, copending U.S. Provisional Patent Application Ser. No. 60/424,429 filed Nov. 20, 2002. All applications listed above are incorporated herein by reference for all purposes.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. For ease of reference, U.S. Provisional Application Ser. Nos. 60/476,584, 60/478,040, 60/478,704, 60/478,657, 60/478,682, and 60/507,689 are hereby fully incorporated herein by reference for all purposes.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of controlling a penetrating member at a tissue site for receiving a body fluid from a wound created at the tissue site, the method comprising:
 (a) providing a lancing device that includes a penetrating member driver coupled to a position sensor and a processor, the position sensor and processor determining a relative position and velocity of the penetrating member based on measuring relative position of the penetrating member with respect to time;
 (b) launching the penetrating member from the lancing device;
 (c) measuring relative position of the penetrating member with respect to time with the processor and position sensor;
 (d) accelerating the penetrating member towards a target tissue;
 (e) in response to measuring relative position of the penetrating with respect to time using an adaptive control algorithm coupled to the penetrating driver to decelerate the penetrating member to follow a desired trajectory, wherein the penetrating member is not decelerated in a sudden manner where the target tissue bounds away from the penetrating member.

2. The method of claim 1 further comprising:
using a planned velocity profile to reach a desired depth of penetration in the tissue site.

3. The method of claim 1 wherein a magnitude of a known value of deceleration is determined with the processor by the deceleration of the penetrating member due to intrinsic frictional forces of the lancing device alone.

4. The method of claim 1 further comprising using a lookup table to determine penetrating member settings based on a desired penetration depth.

5. The method of claim 1 wherein a magnitude of a known value of deceleration is determined by the processor by deceleration of the penetrating member due to intrinsic frictional forces of the lancing device alone.

6. The method of claim 5 wherein a magnitude of a known value of deceleration is determined empirically and implemented by the processor by observing a magnitude of deceleration of the penetrating member when the penetrating member is known to be making contact with the target tissue.

* * * * *